United States Patent
Golz et al.

(10) Patent No.: US 8,343,745 B2
(45) Date of Patent: Jan. 1, 2013

(54) ACYLGLYCEROL ACYLTRANSFERASE-LIKE PROTEIN MGAT-X1 AND USES THEREOF

(75) Inventors: Stefan Golz, Essen (DE); Ulf Brüggemeier, Leichlingen (DE); Bernhard Weingartner, Wülfrath (DE); Andreas Geerts, Wuppertal (DE)

(73) Assignee: Bayer Pharma AG, Berlin (DE)

(*) Notice: Subject to any disclaimer, the term of this patent is extended or adjusted under 35 U.S.C. 154(b) by 208 days.

(21) Appl. No.: 12/854,524

(22) Filed: Aug. 31, 2010

(65) Prior Publication Data

US 2011/0086013 A1    Apr. 14, 2011

Related U.S. Application Data

(62) Division of application No. 10/573,500, filed as application No. PCT/EP2004/010386 on Sep. 16, 2004, now Pat. No. 7,803,593.

(30) Foreign Application Priority Data

Sep. 26, 2003    (EP) .................................... 03021637

(51) Int. Cl.
*C12N 9/10* (2006.01)
*A61K 38/00* (2006.01)
*C07H 21/04* (2006.01)
*C07K 1/00* (2006.01)

(52) U.S. Cl. ........ 435/193; 424/94.5; 536/23.2; 530/350
(58) Field of Classification Search .................. 435/193; 424/94.5; 536/23.2; 530/350
See application file for complete search history.

(56) References Cited

U.S. PATENT DOCUMENTS

2003/0170691 A1* 9/2003 Gimeno et al. .................. 435/6

FOREIGN PATENT DOCUMENTS

WO    03/053363    7/2003
WO    02/068595    9/2006

OTHER PUBLICATIONS

Broun et al., Catalytic plasticity of fatty acid modification enzymes underlying chemical diversity of plant lipids. Science, 1998, vol. 282: 1315-1317.*

Chica et al., Semi-rational approaches to engineering enzyme activity: combining the benefits of directed evolution and rational design. Curr. Opi. Biotechnol., 2005, vol. 16: 378-384.*
Devos et al., Practical limits of function prediction. Proteins: Structure, Function, and Genetics. 2000, vol. 41: 98-107.*
Seffernick et al., Melamine deaminase and Atrazine chlorohydrolase: 98 percent identical but functionally different. J. Bacteriol., 2001, vol. 183 (8): 2405-2410.*
Sen et al., Developments in directed evolution for improving enzyme functions. Appl. Biochem. Biotechnol., 2007, vol. 143: 212-223.*
Whisstock et al., Prediction of protein function from protein sequence. Q. Rev. Biophysics., 2003, vol. 36 (3): 307-340.*
Winter et al., Genomic organization of the DGAT/MOGAT gene family in cattle (*Bos taurus*) and other mammals. Cytogenet. Genome Res., 2003, vol. 102: 1-4.*
Witkowski et al., Conversion of b-ketoacyl synthase to a Malonyl Decarboxylase by replacement of the active cysteine with glutamine. Biochemistry, 1999, vol. 38: 11643-11650.*
Database EMBL 'Online!, Nov. 30, 2002, "Homo spiens diacylglycerol 0-acyltransferase 2-like 3, mRNA (cDNA clone IMAGE: 4746146), partial cds.", XP002310451, retrieved from EBI accession No. EM_HUM:BC039181, Database accession No. BC039181.
Lockwood, et al: "Human intestinal monoacylglycerol acyltransferase: differential features in tissue expression and activity.", American Journal of Physiology, Endocrinology and Metaolism, Nov. 2003, Onlline!, vol. 285, No. 5, Nov. 2003, pp. E927-E937, XP002310529.
Cao et al:, "Properties of the Mouse Intestinal Acyl-CoA: Monoacylglycerol Acyltransferase, MGAT2", Journal of Biological Chemistry, vol. 278, No. 28, May 1, 2003, pp. 25657-25663, XP002979763.

* cited by examiner

*Primary Examiner* — Ganapathirama Raghu
(74) *Attorney, Agent, or Firm* — Banner & Witcoff, Ltd.

(57) ABSTRACT

The present invention is directed to a polynucleotide sequence of a novel acylglycerol acyltransferase-like protein MGAT-X1. The invention also provides the human MGAT-X1 associated with the dermatological diseases, urological diseases, muscle-skeleton disorders, hematological diseases, cancer, reproduction disorders, neurological diseases, metabolic diseases, cardiovascular diseases or gastroenterological diseases. The invention also provides assays for the identification of compounds useful for the modulation of dermatological diseases, urological diseases, muscle-skeleton disorders, hematological diseases, cancer, reproduction disorders, neurological diseases, metabolic diseases, cardiovascular diseases or gastroenterological diseases for treating of such diseases associated with expression of the MGAT-X1. The invention also features compounds which bind to and/or activate or inhibit the activity of MGAT-X1 as well as pharmaceutical compositions comprising such compounds.

2 Claims, 2 Drawing Sheets

Fig. 1

SEQ ID NO:1

5`- ACTGTTCTGAGATCTTTGCCTCCCTCAGGCTCCCGAGAATCATGGCTCAT
TCCAAGCAGCCTAGTCACTTCCAGAGTCTGATGCTTCTGCAGTGGCCTTT
GAGCTACCTTGCCATCTTTTGGATCTTGCAGCCATTGTTCGTCTACCTGC
TGTTTACATCCTTGTGGCCGCTACCAGTGCTTTACTTTGCCTGGTTGTTC
CTGGACTGGAAGACCCCAGAGCGAGGTGGCAGGCGTTCGGCCTGGGTAAG
GAACTGGTGTGTCTGGACCCACATCAGGGACTATTTCCCCATTACGATCC
TGAAGACAAAGGACCTATCACCTGAGCACAACTACCTCATGGGGGTTCAC
CCCCATGGCCTCCTGACCTTTGGCGCCTTCTGCAACTTCTGCACTGAGGC
CACAGGCTTCTCGAAGACCTTCCCAGGCATCACTCCTCACTTGGCCACGC
TGTCCTGGTTCTTCAAGATCCCCTTTGTTAGGGAGTACCTCATGGCCAAA
GGTGTGTGCTCTGTGAGCCAGCCAGCCATCAACTATCTGCTGAGCCATGG
CACTGGCAACCTCGTGGGCATTGTAGTGGGAGGTGTGGGTGAGGCCCTGC
AAAGTGTGCCCAACACCACCACCCTCATCCTCCAGAAGCGCAAGGGGTTC
GTGCGCACAGCCCTCCAGCATGGGGCTCATCTGGTCCCCACCTTCACTTT
TGGGGAAACTGAGGTGTATGATCAGGTGCTGTTCCATAAGGATAGCAGGA
TGTACAAGTTCCAGAGCTGCTTCCGCCGTATCTTTGGTTTCTACTGTTGT
GTCTTCTATGGACAAAGCTTCTGTCAAGGCTCCACTGGGCTCCTGCCATA
CTCCAGGCCTATTGTCACTGTGGTTGGGGAGCCTCTGCCACTGCCCAAA
TTGAAAAGCCAAGCCAGGAGATGGTGGACAAATACCATGCACTTTATATG
GATGCTCTGCACAAACTGTTCGACCAGCATAAGACCCACTATGGCTGCTC
AGAGACCCAAAAGCTGTTTTTCCTGTGAATGAAGGTACTGCATGCCCAGG
AGCACAGGAGTGCCTGCCTTGAAGAAGAGACTCATCTGCCACTAACCAAA
GACAGGCAGGAGATGAGGGAGGTTATATGTG
3`

Fig. 2:

SEQ ID NO:2

MAHSKQPSHFQSLMLLQWPLSYLAIFWILQPLFVYLLFTSLWPLPVLYFA
WLFLDWKTPERGGRRSAWVRNWCVWTHIRDYFPITILKTKDLSPEHNYLM
GVHPHGLLTFGAFCNFCTEATGFSKTFPGITPHLATLSWFFKIPFVREYL
MAKGVCSVSQPAINYLLSHGTGNLVGIVVGGVGEALQSVPNTTTLILQKR
KGFVRTALQHGAHLVPTFTFGETEVYDQVLFHKDSRMYKFQSCFRRIFGF
YCCVFYGQSFCQGSTGLLPYSRPIVTVVGEPLPLPQIEKPSQEMVDKYHA
LYMDALHKLFDQHKTHYGCSETQKLFFL

Fig. 3:

SEQ ID NO:3

5'-CCAGGCCTATTGTCACTGTG-3'

Fig. 4:

SEQ ID NO:4

5'-CTGGCTTGGCTTTTCAATTT-3'

Fig. 5:

SEQ ID NO:5

5'-TTGGGGAGCCTCTGCCACTGC-3'

SEQUENCE LISTING

```
<160> NUMBER OF SEQ ID NOS: 5

<210> SEQ ID NO 1
<211> LENGTH: 1131
<212> TYPE: DNA
<213> ORGANISM: Homo sapiens

<400> SEQUENCE: 1
actgttctga gatctttgcc tccctcaggc tcccgagaat catggctcat tccaagcagc    60
ctagtcactt ccagagtctg atgcttctgc agtggccttt gagctacctt gccatctttt   120
ggatcttgca gccattgttc gtctacctgc tgtttacatc cttgtggccg ctaccagtgc   180
```

```
tttactttgc ctggttgttc ctggactgga agacccccaga gcgaggtggc aggcgttcgg      240
cctgggtaag gaactggtgt gtctggaccc acatcaggga ctatttcccc attacgatcc      300
tgaagacaaa ggacctatca cctgagcaca actacctcat gggggttcac ccccatggcc      360
tcctgacctt tggcgccttc tgcaacttct gcactgaggc cacaggcttc tcgaagacct      420
tcccaggcat cactcctcac ttggccacgc tgtcctggtt cttcaagatc ccctttgtta      480
gggagtacct catggccaaa ggtgtgtgct ctgtgagcca gccagccatc aactatctgc      540
tgagccatgg cactggcaac ctcgtgggca ttgtagtggg aggtgtgggt gaggccctgc      600
aaagtgtgcc caacaccacc accctcatcc tccagaagcg caagggggttc gtgcgcacag      660 ccctccagca tggggctcat ctggtcccca ccttcacttt tggggaaact gaggtgtatg      720
atcaggtgct gttccataag gatagcagga tgtacaagtt ccagagctgc ttccgccgta      780
tctttggttt ctactgttgt gtcttctatg gacaaagctt ctgtcaaggc tccactgggc      840
tcctgccata ctccaggcct attgtcactg tggttgggga gcctctgcca ctgccccaaa      900
ttgaaaagcc aagccaggag atggtggaca ataccatgc actttatatg gatgctctgc       960
acaaactgtt cgaccagcat aagacccact atggctgctc agagacccaa aagctgtttt     1020
tcctgtgaat gaaggtactg catgcccagg agcacaggag tgcctgcctt gaagaagaga     1080
ctcatctgcc actaaccaaa gacaggcagg agatgaggga ggttatatgt g              1131
```

<210> SEQ ID NO 2
<211> LENGTH: 328
<212> TYPE: PRT
<213> ORGANISM: Homo sapiens

<400> SEQUENCE: 2

```
Met Ala His Ser Lys Gln Pro Ser His Phe Gln Ser Leu Met Leu Leu
1               5                   10                  15

Gln Trp Pro Leu Ser Tyr Leu Ala Ile Phe Trp Ile Leu Gln Pro Leu
            20                  25                  30

Phe Val Tyr Leu Leu Phe Thr Ser Leu Trp Pro Leu Pro Val Leu Tyr
        35                  40                  45

Phe Ala Trp Leu Phe Leu Asp Trp Lys Thr Pro Glu Arg Gly Gly Arg
    50                  55                  60

Arg Ser Ala Trp Val Arg Asn Trp Cys Val Trp Thr His Ile Arg Asp
65                  70                  75                  80

Tyr Phe Pro Ile Thr Ile Leu Lys Thr Lys Asp Leu Ser Pro Glu His
                85                  90                  95

Asn Tyr Leu Met Gly Val His Pro His Gly Leu Leu Thr Phe Gly Ala
            100                 105                 110

Phe Cys Asn Phe Cys Thr Glu Ala Thr Gly Phe Ser Lys Thr Phe Pro
        115                 120                 125

Gly Ile Thr Pro His Leu Ala Thr Leu Ser Trp Phe Phe Lys Ile Pro
    130                 135                 140

Phe Val Arg Glu Tyr Leu Met Ala Lys Gly Val Cys Ser Val Ser Gln
145                 150                 155                 160

Pro Ala Ile Asn Tyr Leu Leu Ser His Gly Thr Gly Asn Leu Val Gly
                165                 170                 175

Ile Val Val Gly Gly Val Gly Glu Ala Leu Gln Ser Val Pro Asn Thr
            180                 185                 190

Thr Thr Leu Ile Leu Gln Lys Arg Lys Gly Phe Val Arg Thr Ala Leu
        195                 200                 205
```

```
Gln His Gly Ala His Leu Val Pro Thr Phe Thr Phe Gly Glu Thr Glu
    210                 215                 220

Val Tyr Asp Gln Val Leu Phe His Lys Asp Ser Arg Met Tyr Lys Phe
225                 230                 235                 240

Gln Ser Cys Phe Arg Arg Ile Phe Gly Phe Tyr Cys Cys Val Phe Tyr
                245                 250                 255

Gly Gln Ser Phe Cys Gln Gly Ser Thr Gly Leu Leu Pro Tyr Ser Arg
                260                 265                 270

Pro Ile Val Thr Val Val Gly Glu Pro Leu Pro Leu Pro Gln Ile Glu
            275                 280                 285

Lys Pro Ser Gln Glu Met Val Asp Lys Tyr His Ala Leu Tyr Met Asp
    290                 295                 300

Ala Leu His Lys Leu Phe Asp Gln His Lys Thr His Tyr Gly Cys Ser
305                 310                 315                 320

Glu Thr Gln Lys Leu Phe Phe Leu
                325

<210> SEQ ID NO 3
<211> LENGTH: 20
<212> TYPE: DNA
<213> ORGANISM: artificial sequence
<220> FEATURE:
<223> OTHER INFORMATION: forward primer

<400> SEQUENCE: 3
ccaggcctat tgtcactgtg                                               20

<210> SEQ ID NO 4
<211> LENGTH: 20
<212> TYPE: DNA
<213> ORGANISM: artificial sequence
<220> FEATURE:
<223> OTHER INFORMATION: reverse primer

<400> SEQUENCE: 4
ctggcttggc ttttcaattt                                               20

<210> SEQ ID NO 5
<211> LENGTH: 21
<212> TYPE: DNA
<213> ORGANISM: artificial sequence
<220> FEATURE:
<223> OTHER INFORMATION: probe

<400> SEQUENCE: 5
ttggggagcc tctgccactg c                                             21
```

ACYLGLYCEROL ACYLTRANSFERASE-LIKE PROTEIN MGAT-X1 AND USES THEREOF

This application is a division of Ser. No. 10/573,500, now issued as U.S. Pat. No. 7,803,593, which is a national phase of PCT/EP2004/010386 filed Sep. 16, 2004 and published in English on Apr. 7, 2005. PCT/EP2004/010386 claims the benefit of EP 03021637.8 filed Sep. 26, 2003. Each of these applications is incorporated by reference in its entirety herein.

This application incorporates by reference a 5.07 kb text file created on Aug. 11, 2010 and named "sequencelisting.txt," which is the sequence listing for this application.

TECHNICAL FIELD OF THE INVENTION

Acyl-CoA:diacylglycerol acyltransferase (DGAT; EC 2.3.1.20) is a microsomal enzyme that plays a central role in the metabolism of cellular diacylglycerol lipids. It catalyzes the terminal and only committed step in triacylglycerol synthesis by using diacylglycerol (DAG) and fatty acyl CoA as substrates. MGAT uses mono-acylglycerol (MAG) and fatty acyl CoA as substrates. DGAT had been considered necessary for adipose tissue formation and essential for survival [Cases et al. (1998)].

Oelkers et al. [Oelkers et al. (1998)] identified 2 novel and distinct partial human cDNAs by using the sequence of human acyl-CoA:cholesterol acyltransferase-1 (ACAT1) to screen EST databases: They isolated two "ACAT-related gene products" from a hepatocyte cDNA library which they named ARGP1 and ARGP2. ARGP1 was found to be expressed in numerous human adult tissues and tissue culture cell lines, whereas the expression of ARGP2 was more restricted. The ARGP1 cDNA encodes a protein of 488 amino acids with 9 predicted transmembrane domains, a potential N-linked glycosylation site, and a putative tyrosine phosphorylation motif. Comparison to ACAT1 revealed 22% amino acid identity over the entire molecule. Northern blot analysis of ARGP1 indicated ubiquitous expression with a great variability in level of expression. There was high expression in the adrenal cortex, adrenal medulla, testes, and small intestine, with moderate expression in thyroid, stomach, heart, skeletal muscle, and liver. A 2.0-kb transcript was invariable in all tissues examined, while a 2.4-kb transcript was observed in about half the tissues.

Later, Cheng et al. [Cheng et al. (2001)] cloned DGAT1 from an adipose tissue cDNA library and identified a splice variant, which they designated DGATsv. This DGATsv contains a 77-nucleotide insert of unspliced intron with an in-frame stop codon. It is a truncated form of DGAT1 that terminates at Arg387. Thereby 101 residues from the C-terminus are deleted, including the putative active site. By gel filtration, coimmunoprecipitation, and SDS-PAGE of cross-linked recombinant proteins, the authors determined that both DGAT1 and DGATsv form dimers and tetramers. When coexpressed, the 2 variants formed heterocomplexes.

Smith and co-workers [Smith et al., (2000)] demonstrated that DGAT-deficient mice which were generated by targeted disruption were viable and still synthesized triglycerides. Moreover they found that these mice were lean and resistant to diet-induced obesity. The obesity resistance involved increased energy expenditure and increased activity. DGATt deficiency also altered triglyceride metabolism in other tissues. This includes the mammary gland, where lactation was defective in DGAT–/– females. Smith et al. [Smith et al., (2000)] concluded that multiple mechanisms exist for triglyceride synthesis and suggested that the selective inhibition of DGAT-mediated triglyceride synthesis may be useful for treating obesity.

Buhman et al. [Buhman et al., (2002)] analyzed the DGAT1-deficient mouse model and found that DGAT1 was not essential for quantitative dietary triacylglycerol absorption, even in mice fed a high-fat diet, or for the synthesis of chylomicrons. However, DGAT1 null mice had reduced post-absorptive chylomicronemia 1 hour after a high-fat challenge. When chronically fed a high-fat diet, they accumulated neutral lipid droplets in the cytoplasm of enterocytes, suggesting reduced triacylglycerol absorption. Analysis of intestine from DGAT1 null mice revealed that the activity of enzymes involved in triacylglycerol synthesis, DGAT2 and diacylglycerol transacylase, may help to compensate for the absence of DGAT1.

Using the positional candidate approach, Grisart et al. [Grisart et al. (2002)] mapped a quantitative trait locus with a major effect on milk composition in dairy cattle to the centromeric end of bovine chromosome 14, where the DGAT1 gene maps. They identified a nonconservative Lys232 to Ala substitution in the DGAT1 gene that had a major effect on milk yield and characteristics, including fat content.

SUMMARY OF THE INVENTION

The invention relates to a nucleotide sequence which encodes a novel human MGAT-X1. In the following MGAT-X1 designates a polypeptide having the sequence of or being homologous to SEQ ID No:2, and having MGAT-X1 activity. MGAT-X1 further contemplates various polypeptides arising from post-translational modifications of the polypeptide including but not limited to acetylation, carboxylation, glycosylation, phosphorylation, lipidation and acylation. The invention relates to nucleic acid molecules encoding MGAT-X1 and polypeptides having MGAT-X1-activity, and to their use in the diagnosis or treatment of diseases associated with expression of MGAT-X1.

It is an object of the invention to provide reagents and methods for regulating the expression and activity of human MGAT-X1 for the treatment of dermatological diseases, urological diseases, muscle-skeleton disorders, hematological diseases, cancer, reproduction disorders, neurological diseases, metabolic diseases, cardiovascular diseases or gastroenterological diseases. This and other objects of the invention are provided by one or more of the embodiments described below.

Another object of the invention is a method of screening for agents which can regulate the activity of MGAT-X1. A test compound is contacted with a polypeptide comprising the amino acid sequence selected of the group consisting of SEQ ID NO:2 or a polypeptide which exhibits MGAT-X1 activity and is encoded by a polynucleotide hybridizing under stringent conditions to polynucleotide shown in SEQ ID NO:1; and binding of the test compound to MGAT-X1 is detected, wherein a test compound which binds to the polypeptide is identified as a potential therapeutic agent for decreasing the activity of MGAT-X1. Another embodiment of the invention is a method of screening for agents which can regulate the activity of MGAT-X1. A test compound contacted with a polypeptide comprising the amino acid sequence selected from a group consisting of SEQ ID NO:2 or a polypeptide which exhibits MGAT-X1 activity and is encoded by a polynucleotide hybridizing under stringent conditions to polynucleotide shown in SEQ ID NO:1; and MGAT-X1 activity of the polypeptide is detected, wherein a test compound which increases MGAT-X1 activity is identified as a potential therapeutic agent for increasing the activity of MGAT-X1, and wherein a test compound which decreases MGAT-X1 activity of the polypeptide is identified as a potential therapeutic agent for decreasing the activity of MGAT-X1.

Another object of the invention is a method of screening for agents which can regulate the activity of MGAT-X1. A test compound is contacted with a polynucleotide comprising the sequence selected of the group consisting of (1) SEQ ID NO:1 or (2) a polynucleotide which encodes a polypeptide exhibiting MGAT-X1 activity and hybridizes under stringent conditions to the polynucleotide shown in SEQ ID NO:1; and binding of the test compound to the polynucleotide is detected, wherein a test compound which binds to the polynucleotide is identified as a potential therapeutic agent for decreasing the activity of MGAT-X1.

Another object of the invention is a method of screening for agents which can regulate the activity of MGAT-X1. A test compound is contacted with a product encoded by a polynucleotide which comprises the nucleotide sequence shown in SEQ ID NO:1; and binding of the test compound to the product is detected, wherein a test compound which binds to the product is identified as a potential agent for regulating the activity of MGAT-X1.

Another object of the invention, is a method of reducing the activity of MGAT-X1. A cell is contacted with a reagent which specifically binds to a polynucleotide encoding MGAT-X1 or the MGAT-X1 polypeptide. MGAT-X1 activity is thereby reduced.

Another object of the invention is a method of increasing the activity of MGAT-X1. A cell is contacted with a reagent which specifically binds to a polynucleotide encoding MGAT-X1 or the MGAT-X1 polypeptide. MGAT-X1 activity is thereby increased.

Another object of the invention is the antisense DNA of DNA encoding MGAT-X1; cloning or expression vectors containing nucleic acid encoding MGAT-X1; host cells or organisms transformed with expression vectors containing nucleic acid encoding MGAT-X1; a method for the production and recovery of purified MGAT-X1 from host cells: purified protein, MGAT-X1, which can be used to identify inhibitors or activators of signal transduction involving MGAT-X1; and methods of screening for ligands of MGAT-X1 using transformed cells.

BRIEF DESCRIPTION OF THE DRAWINGS

FIG. 1 shows the nucleotide sequence of a MGAT-X1 polynucleotide (SEQ ID NO:1).

FIG. 2 shows the amino acid sequence of a MGAT-X1 polypolypeptide (SEQ ID NO:2).

FIG. 3 shows the nucleotide sequence of a primer useful for the invention (SEQ ID NO:3).

FIG. 4 shows the nucleotide sequence of a primer useful for the invention (SEQ ID NO:4).

FIG. 5 shows the nucleotide sequence of a primer useful for the invention (SEQ ID NO:5).

DETAILED DESCRIPTION OF THE INVENTION

Nucleotide Sequence

As used herein and designated by the upper case abbreviation, MGAT-X1, refers to an acylglycerol acyltransferase in either naturally occurring or synthetic form and active fragments thereof which have the amino acid sequence of SEQ. ID NO:2. In one embodiment, the polypeptide MGAT-X1 is encoded by mRNAs transcribed from the cDNA, as designated by the lower case abbreviation, MGAT-X1, of SEQ. ID NO: 1. The sequence of MGAT-X1 was assembled from human ESTs: BG674782, W68831, BG742855, W68738.

An "oligonucleotide" is a stretch of nucleotide residues which has a sufficient number of bases to be used as an oligomer, amplimer or probe in a polymerase chain reaction (PCR). Oligonucleotides are prepared from genomic or cDNA sequence and are used to amplify, reveal, or confirm the presence of a similar DNA or RNA in a particular cell or tissue. Oligonucleotides or oligomers comprise portions of a DNA sequence having at least about 10 nucleotides and as many as about 35 nucleotides, preferably about 25 nucleotides.

"Probes" may be derived from naturally occurring or recombinant single- or double-stranded nucleic acids or may be chemically synthesized. They are useful in detecting the presence of identical or similar sequences. Such probes may be labeled with reporter molecules using nick translation, Klenow fill-in reaction, PCR or other methods well known in the art. Nucleic acid probes may be used in southern, northern or in situ hybridizations to determine whether DNA or RNA encoding a certain protein is present in a cell type, tissue, or organ.

A fragment of a polynucleotide or nucleic acid that comprises all or any part of the nucleotide sequence having fewer nucleotides than about 6 kb, preferably fewer than about 1 kb which can be used as a probe.

"Reporter" molecules are radionuclides, enzymes, fluorescent, chemiluminescent, or chromogenic agents which associate with a particular nucleotide or amino acid sequence, thereby establishing the presence of a certain sequence, or allowing for the quantification of a certain sequence.

"Recombinant nucleotide variants" encoding MGAT-X1 may be synthesized by making use of the "redundancy" in the genetic code. Various codon substitutions, such as the silent changes which produce specific restriction sites or codon usage-specific mutations, may be introduced to optimize cloning into a plasmid or viral vector or expression in a particular prokaryotic or eukaryotic host system, respectively.

"Chimeric" molecules may be constructed by introducing all or part of the nucleotide sequence of this invention into a vector containing additional nucleic acid sequence which might be expected to change any one or several of the following MGAT-X1 characteristics: cellular location, distribution, ligand-binding affinities, interchain affinities, degradation/turnover rate, signaling, etc.

"Active" refers to those forms, fragments, or domains of MGAT-X1 which retain the biological and/or antigenic activities of MGAT-X1.

"Naturally occurring MGAT-X1" refers to a polypeptide produced by cells which have not been genetically engineered and specifically contemplates various polypeptides arising from post-translational modifications of the polypeptide including but not limited to acetylation, carboxylation, glycosylation, phosphorylation, lipidation and acylation.

"Derivative" refers to polypeptides which have been chemically modified by techniques such as ubiquitination, labeling (see above), pegylation (derivatization with polyethylene glycol), and chemical insertion or substitution of amino acids such as ornithine which do not normally occur in human proteins.

"Recombinant polypeptide variant" refers to any polypeptide which differs from naturally occurring MGAT-X1 by amino acid insertions, deletions and/or substitutions, created using recombinant DNA techniques. Guidance in determining which amino acid residues may be replaced, added, or deleted, without abolishing activities of interest may be found by comparing the sequence of the polypeptide of interest with that of related polypeptides and minimizing the number of amino acid sequence changes made in highly conserved regions.

Conservative Amino acid "substitutions" result from replacing one amino acid with another having similar structural and/or chemical properties, such as the replacement of a leucine with an isoleucine or valine, an aspartate with a glutamate, or a threonine with a serine.

"Insertions" or "deletions" are typically in the range of about 1 to 5 amino acids. The variation allowed may be experimentally determined by producing the peptide synthetically while systematically making insertions, deletions, or substitutions of nucleotides in the sequence using recombinant DNA techniques.

A "signal or leader sequence" can be used, when desired, to direct the polypeptide through a membrane of a cell. Such a sequence may be naturally present on the polypeptides of the present invention or provided from heterologous sources by recombinant DNA techniques.

An "oligopeptide" is a short stretch of amino acid residues and may be expressed from an oligonucleotide. Oligopeptides comprise a stretch of amino acid residues of at least 3, 5, 10 amino acids and at most 10, 15, 25 amino acids, typically of at least 9 to 13 amino acids, and of sufficient length to display biological and/or antigenic activity.

"Inhibitor" is any substance which retards or prevents a chemical or physiological reaction or response. Common inhibitors include but are not limited to antisense molecules, antibodies, and antagonists.

"Standard" expression is a quantitative or qualitative measurement for comparison. It is based on a statistically appropriate number of normal samples and is created to use as a basis of comparison when performing diagnostic assays, running clinical trials, or following patient treatment profiles.

"Animal" as used herein may be defined to include human, domestic (cats dogs, etc.), agricultural (cows, horses, sheep, etc.) or test species (mouse, rat, rabbit, etc.).

The nucleotide sequences encoding MGAT-X1 (or their complement) have numerous applications in techniques known to those skilled in the art of molecular biology. These techniques include use as hybridization probes, use in the construction of oligomers for PCR, use for chromosome and gene mapping, use in the recombinant production of MGAT-X1, and use in generation of antisense DNA or RNA, their chemical analogs and the like. Uses of nucleotides encoding MGAT-X1 disclosed herein are exemplary of known techniques and are not intended to limit their use in any technique known to a person of ordinary skill in the art. Furthermore, the nucleotide sequences disclosed herein may be used in molecular biology techniques that have not yet been developed, provided the new techniques rely on properties of nucleotide sequences that are currently known, e.g., the triplet genetic code, specific base pair interactions, etc.

It will be appreciated by those skilled in the art that as a result of the degeneracy of the genetic code, a multitude of MGAT-X1-encoding nucleotide sequences may be produced. Some of these will only bear minimal homology to the nucleotide sequence of the known and naturally occurring MGAT-X1. The invention has specifically contemplated each and every possible variation of nucleotide sequence that could be made by selecting combinations based on possible codon choices. These combinations are made in accordance with the standard triplet genetic code as applied to the nucleotide sequence of naturally occurring MGAT-X1, and all such variations are to be considered as being specifically disclosed.

Although the nucleotide sequences which encode MGAT-X1, its derivatives or its variants are preferably capable of hybridizing to the nucleotide sequence of the naturally occurring MGAT-X1 under stringent conditions, it may be advantageous to produce nucleotide sequences encoding MGAT-X1 or its derivatives possessing a substantially different codon usage. Codons can be selected to increase the rate at which expression of the peptide occurs in a particular prokaryotic or eukaryotic expression host in accordance with the frequency with which particular codons are utilized by the host. Other reasons for substantially altering the nucleotide sequence encoding MGAT-X1 and/or its derivatives without altering the encoded amino acid sequence include the production of RNA transcripts having more desirable properties, such as a greater half-life, than transcripts produced from the naturally occurring sequence.

Nucleotide sequences encoding MGAT-X1 may be joined to a variety of other nucleotide sequences by means of well established recombinant DNA techniques. Useful nucleotide sequences for joining to MGAT-X1 include an assortment of cloning vectors such as plasmids, cosmids, lambda phage derivatives, phagemids, and the like. Vectors of interest include expression vectors, replication vectors, probe generation vectors, sequencing vectors, etc. In general, vectors of interest may contain an origin of replication functional in at least one organism, convenient restriction endonuclease sensitive sites, and selectable markers for one or more host cell systems.

Another aspect of the subject invention is to provide for MGAT-X1-specific hybridization probes capable of hybridizing with naturally occurring nucleotide sequences encoding MGAT-X1. Such probes may also be used for the detection of similar GPCR encoding sequences and should preferably contain at least 40% nucleotide identity to MGAT-X1 sequence. The hybridization probes of the subject invention may be derived from the nucleotide sequence presented as SEQ. ID NO: 1 or from genomic sequences including promoter, enhancers or introns of the native gene. Hybridization probes may be labeled by a variety of reporter molecules using techniques well known in the art.

It will be recognized that many deletional or mutational analogs of nucleic acid sequences for MGAT-X1 will be effective hybridization probes for MGAT-X1 nucleic acid. Accordingly, the invention relates to nucleic acid sequences that hybridize with such MGAT-X1 encoding nucleic acid sequences under stringent conditions.

"Stringent conditions" refers to conditions that allow for the hybridization of substantially related nucleic acid sequences. For instance, such conditions will generally allow hybridization of sequence with at least about 85% sequence identity, preferably with at least about 90% sequence identity, more preferably with at least about 95% sequence identity. Hybridization conditions and probes can be adjusted in well-characterized ways to achieve selective hybridization of human-derived probes.

Hybridizations under stringent conditions for hybridization of nucleic acids are, for instance, hybridizations performed in waterous solutions, containing 0.2×SSC (1× standard saline-citrate=150 mM NaCl, 15 mM trinatriumcitrat), at 68° C. (Sambrook et al., 1989).

Nucleic acid molecules that will hybridize to MGAT-X1 encoding nucleic acid under stringent conditions can be identified functionally. Without limitation, examples of the uses for hybridization probes include: histochemical uses such as identifying tissues that express MGAT-X1; measuring mRNA levels, for instance to identify a sample's tissue type or to identify cells that express abnormal levels of MGAT-X1; and detecting polymorphisms in MGAT-X1.

PCR as described in U.S. Pat. Nos. 4,683,195; 4,800,195; and 4,965,188 provides additional uses for oligonucleotides based upon the nucleotide sequence which encodes MGAT-X1. Such probes used in PCR may be of recombinant origin, chemically synthesized, or a mixture of both. Oligomers may comprise discrete nucleotide sequences employed under optimized conditions for identification of MGAT-X1 in specific tissues or diagnostic use. The same two oligomers, a nested set of oligomers, or even a degenerate pool of oligomers may be employed under less stringent conditions for identification of closely related DNAs or RNAs.

Rules for designing polymerase chain reaction ("PCR") primers are now established, as reviewed by PCR Protocols [Devlin et al]. Degenerate primers, i.e., preparations of primers that are heterogeneous at given sequence locations, can be designed to amplify nucleic acid sequences that are highly homologous to, but not identical with MGAT-X1. Strategies are now available that allow for only one of the primers to be required to specifically hybridize with a known sequence. For example, appropriate nucleic acid primers can be ligated to the nucleic acid sought to be amplified to provide the hybridization partner for one of the primers. In this way, only one of the primers need be based on the sequence of the nucleic acid sought to be amplified.

PCR methods for amplifying nucleic acid will utilize at least two primers. One of these primers will be capable of hybridizing to a first strand of the nucleic acid to be amplified and of priming enzyme-driven nucleic acid synthesis in a first direction. The other will be capable of hybridizing the reciprocal sequence of the first strand (if the sequence to be amplified is single stranded, this sequence will initially be hypothetical, but will be synthesized in the first amplification cycle) and of priming nucleic acid synthesis from that strand in the direction opposite the first direction and towards the site of hybridization for the first primer. Conditions for conducting such amplifications, particularly under preferred stringent hybridization conditions, are well known.

Other means of producing specific hybridization probes for MGAT-X1 include the cloning of nucleic acid sequences encoding MGAT-X1 or MGAT-X1 derivatives into vectors for the production of mRNA probes. Such vectors are known in the art, are commercially available and may be used to synthesize RNA probes in vitro by means of the addition of the appropriate RNA polymerase as T7 or SP6 RNA polymerase and the appropriate reporter molecules.

It is possible to produce a DNA sequence, or portions thereof, entirely by synthetic chemistry. After synthesis, the nucleic acid sequence can be inserted into any of the many available DNA vectors and their respective host cells using techniques which are well known in the art. Moreover, synthetic chemistry may be used to introduce mutations into the nucleotide sequence. Alternately, a portion of sequence in which a mutation is desired can be synthesized and recombined with longer portion of an existing genomic or recombinant sequence.

Nucleotide sequences encoding MGAT-X1 may be used to produce a purified oligo- or polypeptide using well known methods of recombinant DNA technology. The oligopeptide may be expressed in a variety of host cells, either prokaryotic or eukaryotic. Host cells may be from the same species from which the nucleotide sequence was derived or from a different species. Advantages of producing an oligonucleotide by recombinant DNA technology include obtaining adequate amounts of the protein for purification and the availability of simplified purification procedures.

Quantitative Determinations of Nucleic Acids

An important step in the molecular genetic analysis of human disease is often the enumeration of the copy number of a nucleic acid or the relative expression of a gene in particular tissues.

Several different approaches are currently available to make quantitative determinations of nucleic acids. Chromosome-based techniques, such as comparative genomic hybridization (CGH) and fluorescent in situ hybridization (FISH) facilitate efforts to cytogenetically localize genomic regions that are altered in tumor cells. Regions of genomic alteration can be narrowed further using loss of heterozygosity analysis (LOH), in which disease DNA is analyzed and compared with normal DNA for the loss of a heterozygous polymorphic marker. The first experiments used restriction fragment length polymorphisms (RFLPs) [Johnson et al], or hypervariable minisatellite DNA [Barnes et al]. In recent years LOH has been performed primarily using PCR amplification of microsatellite markers and electrophoresis of the radiolabeled [Jeffreys et al] or fluorescently labeled PCR products [Weber et al] and compared between paired normal and disease DNAs.

A number of other methods have also been developed to quantify nucleic acids [Gergen et al, Southern et al, Sharp et al]. More recently, PCR and RT-PCR methods have been developed which are capable of measuring the amount of a nucleic acid in a sample. One approach, for example, measures PCR product quantity in the log phase of the reaction before the formation of reaction products plateaus [Thomas et al].

A gene sequence contained in all samples at relatively constant quantity is typically utilized for sample amplification efficiency normalization. This approach, however, suffers from several drawbacks. The method requires that each sample has equal input amounts of the nucleic acid and that the amplification efficiency between samples is identical until the time of analysis. Furthermore, it is difficult using the conventional methods of PCR quantitation such as gel electrophoresis or plate capture hybridization to determine that all samples are in fact analyzed during the log phase of the reaction as required by the method.

Another method called quantitative competitive (QC)-PCR, as the name implies, relies on the inclusion of an internal control competitor in each reaction [Maniatis et al, Becker-Andre et al, Piatak et al in BioTechniques (1993)]. The efficiency of each reaction is normalized to the internal competitor. A known amount of internal competitor is typically added to each sample. The unknown target PCR product is compared with the known competitor PCR product to obtain relative quantitation. A difficulty with this general approach lies in developing an internal control that amplifies with the same efficiency than the target molecule.

5' Fluorogenic Nuclease Assays

Fluorogenic nuclease assays are a real time quantitation method that uses a probe to monitor formation of amplification product. The basis for this method of monitoring the formation of amplification product is to measure continuously PCR product accumulation using a dual-labeled fluorogenic oligonucleotide probe, an approach frequently referred to in the literature simply as the "TaqMan method" [Piatak et al in Science (1993), Heid et al, Gibson et al, Holland et al].

The probe used in such assays is typically a short (about 20-25 bases) oligonucleotide that is labeled with two different fluorescent dyes. The 5' terminus of the probe is attached to a reporter dye and the 3' terminus is attached to a quenching dye, although the dyes could be attached at other locations on the probe as well. The probe is designed to have at least substantial sequence complementarily with the probe binding site. Upstream and downstream PCR primers which bind to flanking regions of the locus are added to the reaction mixture. When the probe is intact, energy transfer between the two fluorophors occurs and the quencher quenches emission from the reporter. During the extension phase of PCR, the probe is cleaved by the 5' nuclease activity of a nucleic acid polymerase such as Taq polymerase, thereby releasing the reporter from the oligonucleotide-quencher and resulting in an increase of reporter emission intensity which can be measured by an appropriate detector.

One detector which is specifically adapted for measuring fluorescence emissions such as those created during a fluorogenic assay is the ABI 7700 or 4700 HT manufactured by Applied Biosystems, Inc. in Foster City, Calif. The ABI 7700 uses fiber optics connected with each well in a 96- or 384 well PCR tube arrangement. The instrument includes a laser for exciting the labels and is capable of measuring the fluorescence spectra intensity from each tube with continuous monitoring during PCR amplification. Each tube is reexamined every 8.5 seconds.

Computer software provided with the instrument is capable of recording the fluorescence intensity of reporter and quencher over the course of the amplification. The recorded values will then be used to calculate the increase in normalized reporter emission intensity on a continuous basis. The increase in emission intensity is plotted versus time, i.e., the number of amplification cycles, to produce a continuous measure of amplification. To quantify the locus in each amplification reaction, the amplification plot is examined at a point during the log phase of product accumulation. This is accomplished by assigning a fluorescence threshold intensity above background and determining the point at which each amplification plot crosses the threshold (defined as the threshold cycle number or Ct). Differences in threshold cycle number are used to quantify the relative amount of PCR target contained within each tube. Assuming that each reaction functions at 100% PCR efficiency, a difference of one Ct represents a two-fold difference in the amount of starting template. The fluorescence value can be used in conjunction with a standard curve to determine the amount of amplification product present.

Non-Probe-Based Detection Methods

A variety of options are available for measuring the amplification products as they are formed. One method utilizes labels, such as dyes, which only bind to double stranded DNA. In this type of approach, amplification product (which is double stranded) binds dye molecules in solution to form a complex. With the appropriate dyes, it is possible to distinguish between dye molecules free in solution and dye molecules bound to amplification product. For example, certain dyes fluoresce only when bound to amplification product. Examples of dyes which can be used in methods of this general type include, but are not limited to, Syber Green™ and Pico Green from Molecular Probes, Inc. of Eugene, Oreg., ethidium bromide, propidium iodide, chromomycin, acridine orange, Hoechst 33258, Toto-1, Yoyo-1, DAPI (4',6-diamidino-2-phenylindole hydrochloride).

Another real time detection technique measures alteration in energy fluorescence energy transfer between fluorophors conjugated with PCR primers [Livak et al.].

Probe-Based Detection Methods

These detection methods involve some alteration to the structure or conformation of a probe hybridized to the locus between the amplification primer pair. In some instances, the alteration is caused by the template-dependent extension catalyzed by a nucleic acid polymerase during the amplification process. The alteration generates a detectable signal which is an indirect measure of the amount of amplification product formed.

For example, some methods involve the degradation or digestion of the probe during the extension reaction. These methods are a consequence of the 5'-3' nuclease activity associated with some nucleic acid polymerases. Polymerases having this activity cleave mononucleotides or small oligonucleotides from an oligonucleotide probe annealed to its complementary sequence located within the locus.

The 3' end of the upstream primer provides the initial binding site for the nucleic acid polymerase. As the polymerase catalyzes extension of the upstream primer and encounters the bound probe, the nucleic acid polymerase displaces a portion of the 5' end of the probe and through its nuclease activity cleaves mononucleotides or oligonucleotides from the probe.

The upstream primer and the probe can be designed such that they anneal to the complementary strand in close proximity to one another. In fact, the 3' end of the upstream primer and the 5' end of the probe may abut one another. In this situation, extension of the upstream primer is not necessary in order for the nucleic acid polymerase to begin cleaving the probe. In the case in which intervening nucleotides separate the upstream primer and the probe, extension of the primer is necessary before the nucleic acid polymerase encounters the 5' end of the probe. Once contact occurs and polymerization continues, the 5'-3' exonuclease activity of the nucleic acid polymerase begins cleaving mononucleotides or oligonucleotides from the 5' end of the probe. Digestion of the probe continues until the remaining portion of the probe dissociates from the complementary strand.

In solution, the two end sections can hybridize with each other to form a hairpin loop. In this conformation, the reporter and quencher dye are in sufficiently close proximity that fluorescence from the reporter dye is effectively quenched by the quencher dye. Hybridized probe, in contrast, results in a linearized conformation in which the extent of quenching is decreased. Thus, by monitoring emission changes for the two dyes, it is possible to indirectly monitor the formation of amplification product.

Probes

The labeled probe is selected so that its sequence is substantially complementary to a segment of the test locus or a reference locus. As indicated above, the nucleic acid site to which the probe binds should be located between the primer binding sites for the upstream and downstream amplification primers.

Primers

The primers used in the amplification are selected so as to be capable of hybridizing to sequences at flanking regions of the locus being amplified. The primers are chosen to have at least substantial complementarity with the different strands of the nucleic acid being amplified. When a probe is utilized to detect the formation of amplification products, the primers are selected in such that they flank the probe, i.e. are located upstream and downstream of the probe.

The primer must have sufficient length so that it is capable of priming the synthesis of extension products in the presence of an agent for polymerization. The length and composition of the primer depends on many parameters, including, for example, the temperature at which the annealing reaction is conducted, proximity of the probe binding site to that of the primer, relative concentrations of the primer and probe and the particular nucleic acid composition of the probe. Typically the primer includes 15-30 nucleotides. However, the length of the primer may be more or less depending on the complexity of the primer binding site and the factors listed above.

Labels for Probes and Primers

The labels used for labeling the probes or primers of the current invention and which can provide the signal corresponding to the quantity of amplification product can take a variety of forms. As indicated above with regard to the 5' fluorogenic nuclease method, a fluorescent signal is one signal which can be measured. However, measurements may also be made, for example, by monitoring radioactivity, colorimetry, absorption, magnetic parameters, or enzymatic activity. Thus, labels which can be employed include, but are not limited to, fluorophors, chromophores, radioactive isotopes, electron dense reagents, enzymes, and ligands having specific binding partners (e.g., biotin-avidin).

Monitoring changes in fluorescence is a particularly useful way to monitor the accumulation of amplification products. A number of labels useful for attachment to probes or primers are commercially available including fluorescein and various fluorescein derivatives such as FAM, HEX, TET and JOE (all which are available from Applied Biosystems, Foster City, Calif.); lucifer yellow, and coumarin derivatives.

Labels may be attached to the probe or primer using a variety of techniques and can be attached at the 5' end, and/or the 3' end and/or at an internal nucleotide. The label can also be attached to spacer arms of various sizes which are attached to the probe or primer. These spacer arms are useful for obtaining a desired distance between multiple labels attached to the probe or primer.

In some instances, a single label may be utilized; whereas, in other instances, such as with the 5' fluorogenic nuclease assays for example, two or more labels are attached to the probe. In cases wherein the probe includes multiple labels, it is generally advisable to maintain spacing between the labels which is sufficient to permit separation of the labels during digestion of the probe through the 5'-3' nuclease activity of the nucleic acid polymerase.

Patients Exhibiting Symptoms of Disease

A number of diseases are associated with changes in the copy number of a certain gene. For patients having symptoms of a disease, the real-time PCR method can be used to determine if the patient has copy number alterations which are known to be linked with diseases that are associated with the symptoms the patient has.

MGAT-X1 Expression

MGAT-X1 Fusion Proteins

Fusion proteins are useful for generating antibodies against MGAT-X1 amino acid sequences and for use in various assay systems. For example, fusion proteins can be used to identify proteins which interact with portions of MGAT-X1 peptide. Protein affinity chromatography or library-based assays for protein-protein interactions, such as the yeast two-hybrid or phage display systems, can be used for this purpose. Such methods are well known in the art and also can be used as drug screens.

A MGAT-X1 fusion protein comprises two polypeptide segments fused together by means of a peptide bond. The first polypeptide segment can comprise at least 54, 75, 100, 125, 139, 150, 175, 200, 225, 250, or 275 contiguous amino acids of SEQ ID NO:2 or of a biologically active variant, such as those described above. The first polypeptide segment also can comprise full-length MGAT-X1.

The second polypeptide segment can be a full-length protein or a protein fragment. Proteins commonly used in fusion protein construction include, but are not limited to β-galactosidase, β-glucuronidase, green fluorescent protein (GFP), autofluorescent proteins, including blue fluorescent protein (BFP), glutathione-S-transferase (GST), luciferase, horseradish peroxidase (HRP), and chloramphenicol acetyltransferase (CAT). Additionally, epitope tags are used in fusion protein constructions, including histidine (His) tags, FLAG tags, influenza hemagglutinin (HA) tags, Myc tags, VSV-G tags, and thioredoxin (Trx) tags. Other fusion constructions can include maltose binding protein (MBP), S-tag, Lex a DNA binding domain (DBD) fusions, GAL4 DNA binding domain fusions, herpes simplex virus (HSV) BP16 protein fusions and G-protein fusions (for example G(alpha)16, Gs, Gi). A fusion protein also can be engineered to contain a cleavage site located adjacent to the MGAT-X1.

Preparation of Polynucleotides

A naturally occurring MGAT-X1 polynucleotide can be isolated free of other cellular components such as membrane components, proteins, and lipids. Polynucleotides can be made by a cell and isolated using standard nucleic acid purification techniques, or synthesized using an amplification technique, such as the polymerase chain reaction (PCR), or by using an automatic synthesizer. Methods for isolating polynucleotides are routine and are known in the art. Any such technique for obtaining a poly-nucleotide can be used to obtain isolated MGAT-X1 polynucleotides. For example, restriction enzymes and probes can be used to isolate polynucleotide fragments which comprises MGAT-X1 nucleotide sequences. Isolated polynucleotides are in preparations which are free or at least 70, 80, or 90% free of other molecules.

MGAT-X1 cDNA molecules can be made with standard molecular biology techniques, using MGAT-X1 mRNA as a template. MGAT-X1 cDNA molecules can thereafter be replicated using molecular biology techniques known in the art. An amplification technique, such as PCR, can be used to obtain additional copies of polynucleotides of the invention, using either human genomic DNA or cDNA as a template.

Alternatively, synthetic chemistry techniques can be used to synthesizes MGAT-X1 polynucleotides. The degeneracy of the genetic code allows alternate nucleotide sequences to be synthesized which will encode MGAT-X1 having, for example, an amino acid sequence shown in SEQ ID NO:2 or a biologically active variant thereof.

Extending Polynucleotides

Various PCR-based methods can be used to extend nucleic acid sequences encoding human MGAT-X1, for example to detect upstream sequences of the MGAT-X1 gene such as promoters and regulatory elements. For example, restriction-site PCR uses universal primers to retrieve unknown sequence adjacent to a known locus. Genomic DNA is first amplified in the presence of a primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR also can be used to amplify or extend sequences using divergent primers based on a known region. Primers can be designed using commercially available software, such as OLIGO 4.06 Primer Analysis software (National Biosciences Inc., Plymouth, Minn.), to be 22-30 nucleotides in length, to have a GC content of 50% or more, and to anneal to the target sequence at temperatures about 68-72° C. The method uses several restriction enzymes to generate a suitable fragment in the known region of a gene. The fragment is then circularized by intramolecular ligation and used as a PCR template.

Another method which can be used is capture PCR, which involves PCR amplification of DNA fragments adjacent to a known sequence in human and yeast artificial chromosome DNA. In this method, multiple restriction enzyme digestions and ligations also can be used to place an engineered double-stranded sequence into an unknown fragment of the DNA molecule before performing PCR.

When screening for full-length cDNAs, it is preferable to use libraries that have been size-selected to include larger cDNAs. Randomly-primed libraries are preferable, in that they will contain more sequences which contain the 5' regions of genes. Use of a randomly primed library may be especially preferable for situations in which an oligo d(T) library does not yield a full-length cDNA. Genomic libraries can be useful for extension of sequence into 5' non-transcribed regulatory regions.

Commercially available capillary electrophoresis systems can be used to analyze the size or confirm the nucleotide sequence of PCR or sequencing products. For example, capillary sequencing can employ flowable polymers for electrophoretic separation, four different fluorescent dyes (one for each nucleotide) which are laser activated, and detection of the emitted wavelengths by a charge coupled device camera. Output/light intensity can be converted to electrical signal using appropriate equipment and software (e.g. GENOTYPER and Sequence NAVIGATOR, Perkin Elmer), and the entire process from loading of samples to computer analysis and electronic data display can be computer controlled. Capillary electrophoresis is especially preferable for the sequencing of small pieces of DNA which might be present in limited amounts in a particular sample.

Obtaining Polypeptides

MGAT-X1 can be obtained, for example, by purification from human cells, by expression of MGAT-X1 polynucleotides, or by direct chemical synthesis.

Protein Purification

MGAT-X1 can be purified from any human cell which expresses the transferase, including those which have been transfected with expression constructs which express MGAT-X1. A purified MGAT-X1 is separated from other compounds which normally associate with MGAT-X1 in the cell, such as certain proteins, carbohydrates, or lipids, using methods well-known in the art. Such methods include, but are not limited to, size exclusion chromatography, ammonium sulfate fractionation, ion exchange chromatography, affinity chromatography, and preparative gel electrophoresis.

Expression of MGAT-X1 Polynucleotides

To express MGAT-X1, MGAT-X1 polynucleotide can be inserted into an expression vector which contains the necessary elements for the transcription and translation of the inserted coding sequence. Methods which are well known to those skilled in the art can be used to construct expression vectors containing sequences encoding MGAT-X1 and appropriate transcriptional and translational control elements. These methods include in vitro recombinant DNA techniques, synthetic techniques, and in vivo genetic recombination [Devlin et al., Science, (1990)].

A variety of expression vector/host systems can be utilized to contain and express sequences encoding MGAT-X1. These include, but are not limited to, microorganisms, such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids), or animal cell systems.

The control elements or regulatory sequences are those non-translated regions of the vector—enhancers, promoters, 5' and 3' untranslated regions—which interact with host cellular proteins to carry out transcription and translation. Such elements can vary in their strength and specificity. Depending on the vector system and host utilized, any number of suitable transcription and translation elements, including constitutive and inducible promoters, can be used. For example, when cloning in bacterial systems, inducible promoters such as the hybrid lacZ promoter of the BLUESCRIPT phagemid (Stratagene, LaJolla, Calif.) or pSPORT1 plasmid (Life Technologies) and the like can be used. The baculovirus polyhedrin promoter can be used in insect cells. Promoters or enhancers derived from the genomes of plant cells (e.g., heat shock, RUBISCO, and storage protein genes) or from plant viruses (e.g., viral promoters or leader sequences) can be cloned into the vector. In mammalian cell systems, promoters from mammalian genes or from mammalian viruses are preferable. If it is necessary to generate a cell line that contains multiple copies of a nucleotide sequence encoding MGAT-X1, vectors based on SV40 or EBV can be used with an appropriate selectable marker.

Bacterial and Yeast Expression Systems

In bacterial systems, a number of expression vectors can be selected. For example, when a large quantity of MGAT-X1 is needed for the induction of antibodies, vectors which direct high level expression of fusion proteins that are readily purified can be used. Such vectors include, but are not limited to, multifunctional *E. coli* cloning and expression vectors such as BLUESCRIPT (Stratagene). In a BLUESCRIPT vector, a sequence encoding MGAT-X1 can be ligated into the vector in frame with sequences for the amino-terminal Met and the subsequent 7 residues of β-galactosidase so that a hybrid protein is produced. pIN vectors or pGEX vectors (Promega, Madison, Wis.) also can be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems can be designed to include heparin, thrombin, or factor Xa protease cleavage sites so that the cloned polypeptide of interest can be released from the GST moiety at will.

Plant and Insect Expression Systems

If plant expression vectors are used, the expression of sequences encoding MGAT-X1 can be driven by any of a number of promoters. For example, viral promoters such as the 35S and 19S promoters of CaMV can be used alone or in combination with the omega leader sequence from TMV [Scott et al. (1990)]. Alternatively, plant promoters such as the small subunit of RUBISCO or heat shock promoters can be used [Takamatsu et al. (1987)]. These constructs can be introduced into plant cells by direct DNA transformation or by pathogen-mediated transfection.

An insect system also can be used to express MGAT-X1. For example, in one such system *Autographa californica* nuclear polyhedrosis virus (AcNPV) is used as a vector to express foreign genes in *Spodoptera frugiperda* cells or in *Trichoplusia* larvae. Sequences encoding MGAT-X1 can be Cloned into a non-essential region of the virus, such as the polyhedrin gene, and placed under control of the polyhedrin promoter. Successful insertion of MGAT-X1 will render the polyhedrin gene inactive and produce recombinant virus lacking coat protein. The recombinant viruses can then be used to infect *S. frugiperda* cells or *Trichoplusia* larvae in which MGAT-X1 can be expressed [Fodor et al., (1993)].

Mammalian Expression Systems

A number of viral-based expression systems can be used to express MGAT-X1 in mammalian host cells. For example, if an adenovirus is used as an expression vector, sequences encoding MGAT-X1 can be ligated into an adenovirus transcription/translation complex comprising the late promoter and tripartite leader sequence. Insertion in a non-essential E1 or E3 region of the viral genome can be used to obtain a viable virus which is capable of expressing MGAT-X1 in infected host cells [Engelhard et al. (1994)]. If desired, transcription enhancers, such as the Rous sarcoma virus (RSV) enhancer, can be used to increase expression in mammalian host cells.

Human artificial chromosomes (HACs) also can be used to deliver larger fragments of DNA than can be contained and expressed in a plasmid. HACs of 6M to 10M are constructed and delivered to cells via conventional delivery methods (e.g., liposomes, polycationic amino polymers, or vesicles). Specific initiation signals also can be used to achieve more efficient translation of sequences encoding MGAT-X1. Such signals include the ATG initiation codon and adjacent sequences. In cases where sequences encoding MGAT-X1, its initiation codon, and upstream sequences are inserted into the appropriate expression vector, no additional transcriptional or translational control signals may be needed. However, in cases where only coding sequence, or a fragment thereof, is inserted, exogenous translational control signals (including the ATG initiation codon) should be provided. The initiation codon should be in the correct reading frame to ensure translation of the entire insert. Exogenous translational elements and initiation codons can be of various origins, both natural and synthetic.

Host Cells

A host cell strain can be chosen for its ability to modulate the expression of the inserted sequences or to process the expressed MGAT-X1 in the desired fashion. Such modifications of the polypeptide include, but are not limited to, acetylation, carboxylation, glycosylation, phosphorylation, lipidation, and acylation. Post-translational processing which cleaves a "prepro" form of the polypeptide also can be used to facilitate correct insertion, folding and/or function. Different host cells which have specific cellular machinery and characteristic mechanisms for post-translational activities (e.g., CHO, HeLa, MDCK, HEK293, and WI38), are available from the American Type Culture Collection (ATCC; 10801 University Boulevard, Manassas, Va. 20110-2209) and can be chosen to ensure the correct modification and processing of the foreign protein.

Stable expression is preferred for long-term, high-yield production of recombinant proteins. For example, cell lines which stably express MGAT-X1 can be transformed using expression vectors which can contain viral origins of replication and/or endogenous expression elements and a selectable marker gene on the same or on a separate vector. Following the introduction of the vector, cells can be allowed to grow for 1-2 days in an enriched medium before they are switched to a selective medium. The purpose of the selectable marker is to confer resistance to selection, and its presence allows growth and recovery of cells which successfully express the introduced MGAT-X1 sequences. Resistant clones of stably transformed cells can be proliferated using tissue culture techniques appropriate to the cell type. Any number of selection systems can be used to recover transformed cell lines. These include, but are not limited to, the herpes simplex virus thymidine kinase [Logan & Shenck, (1984)] and adenine phosphoribosyltransferase [Wigler et al., (1977)] genes which can be employed in $tk^-$ or $aprt^-$ cells, respectively. Also, antimetabolite, antibiotic, or herbicide resistance can be used as the basis for selection. For example, dhfr confers resistance to methotrexate [Lowy et al., (1980)], npt confers resistance to the aminoglycosides, neomycin and G-418 [Wigler et al., Proc. Natl. Acad. Sci. (1980)], and als and pat confer resistance to chlorsulfuron and phosphinotricin acetyltransferase, respectively [Colbere-Garapin et al., (1981)]. Additional selectable genes have been described. For example, trpB allows cells to utilize indole in place of tryptophan, or hisD, which allows cells to utilize histinol in place of histidine [Murray et al., (1992)]. Visible markers such as anthocyanins, β-glucuronidase and its substrate GUS, and luciferase and its substrate luciferin, can be used to identify transformants and to quantify the amount of transient or stable protein expression attributable to a specific vector system Detecting Polypeptide Expression Although the presence of marker gene expression suggests that a MGAT-X1 polynucleotide is also present, its presence and expression may need to be confirmed. For example, if a sequence encoding MGAT-X1 is inserted within a marker gene sequence, transformed cells containing sequences which encode MGAT-X1 can be identified by the absence of marker gene function. Alternatively, a marker gene can be placed in tandem with a sequence encoding MGAT-X1 under the control of a single promoter. Expression of the marker gene in response to induction or selection usually indicates expression of MGAT-X1 polynucleotide.

Alternatively, host cells which contain a MGAT-X1 polynucleotide and which express MGAT-X1 can be identified by a variety of procedures known to those of skill in the art. These procedures include, but are not limited to, DNA-DNA or DNA-RNA hybridizations and protein bioassay or immunoassay techniques which include membrane, solution, or chip-based technologies for the detection and/or quantification of nucleic acid or protein. For example, the presence of a polynucleotide sequence encoding MGAT-X1 can be detected by DNA-DNA or DNA-RNA hybridization or amplification using probes or fragments or fragments of polynucleotides encoding MGAT-X1. Nucleic acid amplification-based assays involve the use of oligonucleotides selected from sequences encoding MGAT-X1 to detect transformants which contain a MGAT-X1 polynucleotide.

A variety of protocols for detecting and measuring the expression of MGAT-X1, using either polyclonal or monoclonal antibodies specific for the polypeptide, are known in the art. Examples include enzyme-linked immunosorbent assay (ELISA), radioimmunoassay (RIA), and fluorescence activated cell sorting (FACS). A two-site, monoclonal-based immunoassay using monoclonal antibodies reactive to two non-interfering epitopes on MGAT-X1 can be used, or a competitive binding assay can be employed [Hartman & Mulligan, (1988), Hampton et al., (1990)].

A wide variety of labels and conjugation techniques are known by those skilled in the art and can be used in various nucleic acid and amino acid assays. Means for producing labeled hybridization or PCR probes for detecting sequences related to polynucleotides encoding MGAT-X1 include oligolabeling, nick translation, end-labeling, or PCR amplification using a labeled nucleotide. Alternatively, sequences encoding MGAT-X1 can be cloned into a vector for the production of an mRNA probe. Such vectors are known in the art, are commercially available, and can be used to synthesize RNA probes in vitro by addition of labeled nucleotides and an appropriate RNA polymerase such as T7, T3, or SP6. These procedures can be conducted using a variety of commercially available kits (Amersham Pharmacia Biotech, Promega, and US Biochemical). Suitable reporter molecules or labels which can be used for ease of detection include radionuclides, enzymes, and fluorescent, chemiluminescent, or chromogenic agents, as well as substrates, cofactors, inhibitors, magnetic particles, and the like.

Expression and Purification of Polypeptides

Host cells transformed with nucleotide sequences encoding MGAT-X1 can be cultured under conditions suitable for the expression and recovery of the protein from cell culture. The polypeptide produced by a transformed cell can be secreted or contained intracellularly depending on the sequence and/or the vector used. As will be understood by those of skill in the art, expression vectors containing polynucleotides which encode MGAT-X1 can be designed to contain signal sequences which direct secretion of soluble MGAT-X1 through a prokaryotic or eukaryotic cell membrane or which direct the membrane insertion of membrane-bound MGAT-X1.

As discussed above, other constructions can be used to join a sequence encoding MGAT-X1 to a nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). Inclusion of cleavable linker sequences such as those specific for Factor XA or enterokinase (Invitrogen, San Diego, Calif.) between the purification domain and MGAT-X1 also can be used to facilitate purification. One such expression vector provides for expression of a fusion protein containing MGAT-X1 and 6 histidine residues preceding a thioredoxin or an enterokinase cleavage site. The histidine residues facilitate purification by IMAC (immobilized metal ion affinity chromatography) Maddox et al., (1983)], while the enterokinase cleavage site provides a means for purifying MGAT-X1 from the fusion protein [Porath et al., (1992)].

Chemical Synthesis

Sequences encoding MGAT-X1 can be synthesized, in whole or in part, using chemical methods well known in the art [Kroll et al. (1993), Caruthers et al., (1980)]. Alternatively, MGAT-X1 itself can be produced using chemical methods to synthesize its amino acid sequence, such as by direct peptide synthesis using solid-phase techniques [Horn et al., (1980); Merrifield et al., (1963)]. Protein synthesis can either be performed using manual techniques or by automation. Automated synthesis can be achieved, for example, using Applied Biosystems 431A Peptide Synthesizer (Perkin Elmer). Optionally, fragments of MGAT-X1 can be separately synthesized and combined using chemical methods to produce a full-length molecule.

The newly synthesized peptide can be substantially purified by preparative high performance liquid chromatography. The composition of a synthetic MGAT-X1 can be confirmed by amino acid analysis or sequencing. Additionally, any portion of the amino acid sequence of MGAT-X1 can be altered during direct synthesis and/or combined using chemical methods with sequences from other proteins to produce a variant polypeptide or a fusion protein.

Production of Altered Polypeptides

As will be understood by those of skill in the art, it may be advantageous to produce MGAT-X1-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences referred to herein can be engineered using methods generally known in the art to alter MGAT-X1-encoding sequences for a variety of reasons, including but not limited to, alterations which modify the cloning, processing, and/or expression of the polypeptide or mRNA product. DNA shuffling by random fragmentation and PCR reassembly of gene fragments and synthetic oligonucleotides can be used to engineer the nucleotide sequences. For example, site-directed mutagenesis can be used to insert new restriction sites, alter glycosylation patterns, change codon preference, produce splice variants, introduce mutations, and so forth.

Antibodies

Any type of antibody known in the art can be generated to bind specifically to an epitope of MGAT-X1. "Antibody" as used herein includes intact immunoglobulin molecules, as well as fragments thereof, such as Fab, $F(ab')_2$, and Fv, which are capable of binding an epitope of MGAT-X1. Typically, at least 6, 8, 10, or 12 contiguous amino acids are required to form an epitope. However, epitopes which involve non-contiguous amino acids may require more, e.g., at least 15, 25, or 50 amino acid. An antibody which specifically binds to an epitope of MGAT-X1 can be used therapeutically, as well as in immunochemical assays, such as Western blots, ELISAs, radioimmunoassays, immunohistochemical assays, immunoprecipitation, or other immunochemical assays known in the art. Various immunoassays can be used to identify antibodies having the desired specificity. Numerous protocols for competitive binding or immunoradiometric assays are well known in the art. Such immunoassays typically involve the measurement of complex formation between an immunogen and an antibody which specifically binds to the immunogen.

Typically, an antibody which specifically binds to MGAT-X1 provides a detection signal at least 5-, 10-, or 20-fold higher than a detection signal provided with other proteins when used in an immunochemical assay. Preferably, antibodies which specifically bind to MGAT-X1 do not detect other proteins in immunochemical assays and can immunoprecipitate MGAT-X1 from solution.

MGAT-X1 can be used to immunize a mammal, such as a mouse, rat, rabbit, guinea pig, monkey, or human, to produce polyclonal antibodies. If desired, MGAT-X1 can be conjugated to a carrier protein, such as bovine serum albumin, thyroglobulin, and keyhole limpet hemocyanin. Depending on the host species, various adjuvants can be used to increase the immunological response. Such adjuvants include, but are not limited to, Freund's adjuvant, mineral gels (e.g., aluminum hydroxide), and surface active substances (e.g. lysolecithin, pluronic polyols, polyanions, peptides, oil emulsions, keyhole limpet hemocyanin, and dinitrophenol). Among adjuvants used in humans, BCG (bacilli Calmette-Guerin) and *Corynebacterium parvum* are especially useful.

Monoclonal antibodies which specifically bind to MGAT-X1 can be prepared using any technique which provides for the production of antibody molecules by continuous cell lines in culture. These techniques include, but are not limited to, the hybridoma technique, the human B-cell hybridoma technique, and the EBV-hybridoma technique [Roberge et at, (1995); Kohler et al., (1985); Kozbor et al., (1985); Cote et al., (1983)].

In addition, techniques developed for the production of "chimeric antibodies," the splicing of mouse antibody genes to human antibody genes to obtain a molecule with appropriate antigen specificity and biological activity, can be used

[Cole et al. (1984); Morrison et al. (1984); Neuberger et al. (1984)]. Monoclonal and other antibodies also can be "humanized" to prevent a patient from mounting an immune response against the antibody when it is used therapeutically. Such antibodies may be sufficiently similar in sequence to human antibodies to be used directly in therapy or may require alteration of a few key residues. Sequence differences between rodent antibodies and human sequences can be minimized by replacing residues which differ from those in the human sequences by site directed mutagenesis of individual residues or by grating of entire complementarity determining regions. Antibodies which specifically bind to MGAT-X1 can contain antigen binding sites which are either partially or fully humanized, as disclosed in U.S. Pat. No. 5,565,332.

Alternatively, techniques described for the production of single chain antibodies can be adapted using methods known in the art to produce single chain antibodies which specifically bind to MGAT-X1. Antibodies with related specificity, but of distinct idiotypic composition, can be generated by chain shuffling from random combinatorial immunoglobin libraries [Takeda et al., (1985)]. Single-chain antibodies also can be constructed using a DNA amplification method, such as PCR, using hybridoma cDNA as a template. Single-chain antibodies can be mono- or bispecific, and can be bivalent or tetravalent. Construction of tetravalent, bispecific single-chain antibodies is taught. A nucleotide sequence encoding a single-chain antibody can be constructed using manual or automated nucleotide synthesis, cloned into an expression construct using standard recombinant DNA methods, and introduced into a cell to express the coding sequence, as described below. Alternatively, single-chain antibodies can be produced directly using, for example, filamentous phage technology [Burton et al. (1991); Verhaar et al. (1995)].

Antibodies which specifically bind to MGAT-X1 also can be produced by inducing in vivo production in the lymphocyte population or by screening immunoglobulin libraries or panels of highly specific binding reagents. Other types of antibodies can be constructed and used therapeutically in methods of the invention. For example, chimeric antibodies can be constructed as disclosed in WO 93/03151. Binding proteins which are derived from immunoglobulins and which are multivalent and multispecific, such as the "diabodies" described in WO 94/13804, also can be prepared.

Antibodies according to the invention can be purified by methods well known in the art. For example, antibodies can be affinity purified by passage over a column to which MGAT-X1 is bound. The bound antibodies can then be eluted from the column using a buffer with a high salt concentration.

Antisense Oligonucleotides

Antisense oligonucleotides are nucleotide sequences which are complementary to a specific DNA or RNA sequence. Once introduced into a cell, the complementary nucleotides combine with natural sequences produced by the cell to form complexes and block either transcription or translation. Preferably, an antisense oligonucleotide is at least 11 nucleotides in length, but can be at least 12, 15, 20, 25, 30, 35, 40, 45, or 50 or more nucleotides long. Longer sequences also can be used. Antisense oligonucleotide molecules can be provided in a DNA construct and introduced into a cell as described above to decrease the level of MGAT-X1 gene products in the cell.

Antisense oligonucleotides can be deoxyribonucleotides, ribonucleotides, or a combination of both. Oligonucleotides can be synthesized manually or by an automated synthesizer, by covalently linking the 5' end of one nucleotide with the 3' end of another nucleotide with non-phosphodiester internucleotide linkages such alkylphosphonates, phosphorothioates, phosphorodithioates, alkylphosphonothioates, alkylphosphonates, phosphoramidates, phosphate esters, carbamates, acetamidate, carboxymethyl esters, carbonates, and phosphate triesters.

Modifications of MGAT-X1 gene expression can be obtained by designing antisense oligonucleotides which will form duplexes to the control, 5', or regulatory regions of the MGAT-X1 gene. Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or chaperons. Therapeutic advances using triplex DNA have been described in the literature [Nicholls et al. (1993)]. An antisense oligonucleotide also can be designed to block translation of mRNA by preventing the transcript from binding to ribosomes.

Precise complementarity is not required for successful complex formation between an antisense oligonucleotide and the complementary sequence of a MGAT-X1 polynucleotide. Antisense oligonucleotides which comprise, for example, 2, 3, 4, or 5 or more stretches of contiguous nucleotides which are precisely complementary to a MGAT-X1 polynucleotide, each separated by a stretch of contiguous nucleotides which are not complementary to adjacent MGAT-X1 nucleotides, can provide sufficient targeting specificity for MGAT-X1 mRNA. Preferably, each stretch of complementary contiguous nucleotides is at least 4, 5, 6, 7, or 8 or more nucleotides in length. Non-complementary intervening sequences are preferably 1, 2, 3, or 4 nucleotides in length. One skilled in the art can easily use the calculated melting point of an antisense-sense pair to determine the degree of mismatching which will be tolerated between a particular antisense oligonucleotide and a particular MGAT-X1 polynucleotide sequence. Antisense oligonucleotides can be modified without affecting their ability to hybridize to a MGAT-X1 polynucleotide. These modifications can be internal or at one or both ends of the antisense molecule. For example, internucleoside phosphate linkages can be modified by adding cholesteryl or diamine moieties with varying numbers of carbon residues between the amino groups and terminal ribose. Modified bases and/or sugars, such as arabinose instead of ribose, or a 3',5'-substituted oligonucleotide in which the 3' hydroxyl group or the 5' phosphate group are substituted, also can be employed in a modified antisense oligonucleotide. These modified oligonucleotides can be prepared by methods well known in the art [Gee et al. (1994); Agrawal et al. (1992); Uhlmann et al. (1990)].

Ribozymes

Ribozymes are RNA molecules with catalytic activity Uhlmann et al. (1987); Cech et al. (1987), (1990), (1992)]. Ribozymes can be used to inhibit gene function by cleaving an RNA sequence, as is known in the art (U.S. Pat. No. 5,641,673). The mechanism of ribozyme action involves sequence-specific hybridization of the ribozyme molecule to complementary target RNA, followed by endonucleolytic cleavage. Examples include engineered hammerhead motif ribozyme molecules that can specifically and efficiently catalyze endonucleolytic cleavage of specific nucleotide sequences. The coding sequence of a MGAT-X1 polynucleotide can be used to generate ribozymes which will specifically bind to mRNA transcribed from a MGAT-X1 polynucleotide. Methods of designing and constructing ribozymes which can cleave other RNA molecules in trans in a highly sequence specific manner have been developed and described in the art [Couture & Stinchcomb (1996)]. For example, the cleavage activity of ribozymes can be targeted to specific RNAs by engineering a discrete "hybridization" region into the ribozyme. The hybridization region contains a sequence complementary to the target RNA and thus specifically hybridizes with the.

Specific ribozyme cleavage sites within a MGAT-X1 RNA target can be identified by scanning the target molecule for ribozyme cleavage sites which include the following sequences: GUA, GUU, and GUC. Once identified, short RNA sequences of between 15 and 20 ribonucleotides corresponding to the region of the target RNA containing the cleavage site can be evaluated for secondary structural features which may render the target inoperable. Suitability of candidate MGAT-X1 RNA targets also can be evaluated by testing accessibility to hybridization with complementary oligonucleotides using ribonuclease protection assays. The nucleotide sequences shown in SEQ ID NO:1 and its complement provide sources of suitable hybridization region sequences. Longer complementary sequences can be used to increase the affinity of the hybridization sequence for the target. The hybridizing and cleavage regions of the ribozyme can be integrally related such that upon hybridizing to the target RNA through the complementary regions, the catalytic region of the ribozyme can cleave the target.

Ribozymes can be introduced into cells as part of a DNA construct. Mechanical methods, such as microinjection, liposome-mediated transfection, electroporation, or calcium phosphate precipitation, can be used to introduce a ribozyme-containing DNA construct into cells in which it is desired to decrease MGAT-X1 expression. Alternatively, if it is desired that the cells stably retain the DNA construct, the construct can be supplied on a plasmid and maintained as a separate element or integrated into the genome of the cells, as is known in the art. A ribozyme-encoding DNA construct can include transcriptional regulatory elements, such as a promoter element, an enhancer or UAS element, and a transcriptional terminator signal, for controlling transcription of ribozymes in the cells (U.S. Pat. No. 5,641,673). Ribozymes also can be engineered to provide an additional level of regulation, so that destruction of mRNA occurs only when both a ribozyme and a target gene are induced in the cells.

Screening/Screening Assays
Regulators

Regulators as used herein, refers to MGAT-X1 agonists and MGAT-X1 antagonists. Agonists of MGAT-X1 are molecules which, when bound to MGAT-X1, increase or prolong the activity of MGAT-X1. Agonists of MGAT-X1 include proteins, nucleic acids, carbohydrates, small molecules, or any other molecule which activate MGAT-X1. Antagonists of MGAT-X1 are molecules which, when bound to MGAT-X1, decrease the amount or the duration of the activity of MGAT-X1. Antagonists include proteins, nucleic acids, carbohydrates, antibodies, small molecules, or any other molecule which decrease the activity of MGAT-X1.

The term "modulate," as it appears herein, refers to a change in the activity of MGAT-X1. For example, modulation may cause an increase or a decrease in protein activity, binding characteristics, or any other biological, functional, or immunological properties of MGAT-X1.

As used herein, the terms "specific binding" or "specifically binding" refer to that interaction between a protein or peptide and an agonist, an antibody, or an antagonist. The interaction is dependent upon the presence of a particular structure of the protein recognized by the binding molecule (i.e., the antigenic determinant or epitope). For example, if an antibody is specific for epitope "A," the presence of a polypeptide containing the epitope A, or the presence of free unlabeled A, in a reaction containing free labeled A and the antibody will reduce the amount of labeled A that binds to the antibody.

The invention provides methods (also referred to herein as "screening assays") for identifying compounds which can be used for the treatment of dermatological diseases, urological diseases, muscle-skeleton disorders, hematological diseases, cancer, reproduction disorders, neurological diseases, metabolic diseases, cardiovascular diseases or gastroenterological diseases. The methods entail the identification of candidate or test compounds or agents (e.g., peptides, peptidomimetics, small molecules or other molecules) which bind to MGAT-X1 and/or have a stimulatory or inhibitory effect on the biological activity of MGAT-X1 or its expression and then determining which of these compounds have an effect on symptoms or diseases regarding the dermatological diseases, urological diseases, muscle-skeleton disorders, hematological diseases, cancer, reproduction disorders, neurological diseases, metabolic diseases, cardiovascular diseases or gastroenterological diseases in an in vivo assay.

Candidate or test compounds or agents which bind to MGAT-X1 and/or have a stimulatory or inhibitory effect on the activity or the expression of MGAT-X1 are identified either in assays that employ cells which express MGAT-X1 on the cell surface (cell-based assays) or in assays with isolated MGAT-X1 (cell-free assays). The various assays can employ a variety of variants of MGAT-X1 (e.g., full-length MGAT-X1, a biologically active fragment of MGAT-X1, or a fusion protein which includes all or a portion of MGAT-X1). Moreover, MGAT-X1 can be derived from any suitable mammalian species (e.g., human MGAT-X1, rat MGAT-X1 or murine MGAT-X1). The assay can be a binding assay entailing direct or indirect measurement of the binding of a test compound or a known MGAT-X1 ligand to MGAT-X1. The assay can also be an activity assay entailing direct or indirect measurement of the activity of MGAT-X1. The assay can also be an expression assay entailing direct or indirect measurement of the expression of MGAT-X1 mRNA or MGAT-X1 protein. The various screening assays are combined with an in vivo assay entailing measuring the effect of the test compound on the symtoms of a dermatological diseases, urological diseases, muscle-skeleton disorders, hematological diseases, cancer, reproduction disorders, neurological diseases, metabolic diseases, cardiovascular diseases or gastroenterological diseases.

In one embodiment, the invention provides assays for screening candidate or test compounds which bind to or modulate the activity of a membrane-bound (cell surface expressed) form of MGAT-X1. Such assays can employ full-length MGAT-X1, a biologically active fragment of MGAT-X1, or a fusion protein which includes all or a portion of MGAT-X1. As described in greater detail below, the test compound can be obtained by any suitable means, e.g., from conventional compound libraries. Determining the ability of the test compound to bind to a membrane-bound form of MGAT-X1 can be accomplished, for example, by coupling the test compound with a radioisotope or enzymatic label such that binding of the test compound to the MGAT-X1-expressing cell can be measured by detecting the labeled compound in a complex. For example, the test compound can be labeled with . . . $^{125}$I, . . . $^{35}$S, . . . $^{14}$C, or . . . $^{3}$H, either directly or indirectly, and the radioisotope detected by direct counting of radioemmission or by scintillation counting. Alternatively, the test compound can be enzymatically labeled with, for example, horseradish peroxidase, alkaline phosphatase, or luciferase, and the enzymatic label detected by determination of conversion of an appropriate substrate to product.

In a competitive binding format, the assay comprises contacting MGAT-X1-expressing cell with a known compound which binds to MGAT-X1 to form an assay mixture, contacting the assay mixture with a test compound, and determining the ability of the test compound to interact with the MGAT-X1-expressing cell, wherein determining the ability of the test compound to interact with the MGAT-X1-expressing cell comprises determining the ability of the test compound to preferentially bind the MGAT-X1-expressing cell as compared to the known compound.

In another embodiment, the assay is a cell-based assay comprising contacting a cell expressing a membrane-bound form of MGAT-X1 (e.g., full-length MGAT-X1, a biologically active fragment of MGAT-X1, or a fusion protein which includes all or a portion of MGAT-X1) expressed on the cell surface with a test compound and determining the ability of the test compound to modulate (e.g., stimulate or inhibit) the activity of the membrane-bound form of MGAT-X1. Determining the ability of the test compound to modulate the activity of the membrane-bound form of MGAT-X1 can be accomplished by any method suitable for measuring the activity of MGAT-X1. The activity of a transporter can be measured in a number of ways, not all of which are suitable for any given transferase.

Determining the ability of the test compound to modulate the activity of MGAT-X1 can be accomplished, for example, by determining the ability of MGAT-X1 to bind to or interact with a target molecule. The target molecule can be a molecule with which MGAT-X1 binds or interacts with in nature, for example, a molecule on the surface of a cell which expresses MGAT-X1, a molecule on the surface of a second cell, a molecule in the extracellular milieu, a molecule associated with the internal surface of a cell membrane or a cytoplasmic molecule. The target molecule can be a component of a signal transduction pathway which facilitates transduction of an extracellular signal (e.g., a signal generated by binding of a MGAT-X1 ligand, through the cell membrane and into the cell. The target molecule can be, for example, a second intracellular protein which has catalytic activity or a protein which facilitates the association of downstream signaling molecules with MGAT-X1.

Determining the ability of MGAT-X1 to bind to or interact with a target molecule can be accomplished by one of the methods described above for determining direct binding. In one embodiment, determining the ability of a polypeptide of the invention to bind to or interact with a target molecule can be accomplished by determining the activity of the target molecule. For example, the activity of the target molecule can be determined by detecting induction of a cellular second messenger of the target (e.g., intracellular $Ca^{2+}$, diacylglycerol, IP3, etc.), detecting catalytic/enzymatic activity of the target on an appropriate substrate, detecting the induction of a reporter gene (e.g., a regulatory element that is responsive to a polypeptide of the invention operably linked to a nucleic acid encoding a detectable marker, e.g., luciferase), or detecting a cellular response.

The present invention also includes cell-free assays. Such assays involve contacting a form of MGAT-X1 (e.g., full-length MGAT-X1, a biologically active fragment of MGAT-X1, or a fusion protein comprising all or a portion of MGAT-X1) with a test compound and determining the ability of the test compound to bind to MGAT-X1. Binding of the test compound to MGAT-X1 can be determined either directly or indirectly as described above. In one embodiment, the assay includes contacting MGAT-X1 with a known compound which binds MGAT-X1 to form an assay mixture, contacting the assay mixture with a test compound, and determining the ability of the test compound to interact with MGAT-X1, wherein determining the ability of the test compound to interact with MGAT-X1 comprises determining the ability of the test compound to preferentially bind to MGAT-X1 as compared to the known compound.

The cell-free assays of the present invention are amenable to use of either a membrane-bound form of MGAT-X1 or a soluble fragment thereof. In the case of cell-free assays comprising the membrane-bound form of the polypeptide, it may be desirable to utilize a solubilizing agent such that the membrane-bound form of the polypeptide is maintained in solution. Examples of such solubilizing agents include but are not limited to non-ionic detergents such as n-octylglucoside, n-dodecyl-glucoside, n-dodecylmaltoside, octanoyl-N-methylglucamide, decanoyl-N-methyl-glucamide, Triton X-100, Triton X-114, Thesit, Isotridecypoly(ethylene glycol ether)n, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

In various embodiments of the above assay methods of the present invention, it may be desirable to immobilize MGAT-X1 (or a MGAT-X1 target molecule) to facilitate separation of complexed from uncomplexed forms of one or both of the proteins, as well as to accommodate automation of the assay. Binding of a test compound to MGAT-X1, or interaction of MGAT-X1 with a target molecule in the presence and absence of a candidate compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the proteins to be bound to a matrix. For example, glutathione-S-transferase (GST) fusion proteins or glutathione-S-transferase fusion proteins can be adsorbed onto glutathione sepharose beads (Sigma Chemical; St. Louis, Mo.) or glutathione derivatized microtitre plates, which are then combined with the test compound or the test compound and either the non-adsorbed target protein or MGAT-X1, and the mixture incubated under conditions conducive to complex formation (e.g., at physiological conditions for salt and pH). Following incubation, the beads or microtitre plate wells are washed to remove any unbound components and complex formation is measured either directly or indirectly, for example, as described above. Alternatively, the complexes can be dissociated from the matrix, and the level of binding or activity of MGAT-X1 can be determined using standard techniques.

Other techniques for immobilizing proteins on matrices can also be used in the screening assays of the invention. For example, either MGAT-X1 or its target molecule can be immobilized utilizing conjugation of biotin and streptavidin. Biotinylated polypeptide of the invention or target molecules can be prepared from biotin-NHS (N-hydroxy-succinimide) using techniques well known in the art (e.g., biotinylation kit, Pierce Chemicals; Rockford, and immobilized in the wells of streptavidin-coated plates (Pierce Chemical). Alternatively, antibodies reactive with MGAT-X1 or target molecules but which do not interfere with binding of the polypeptide of the invention to its target molecule can be derivatized to the wells of the plate, and unbound target or polypeptide of the invention trapped in the wells by antibody conjugation. Methods for detecting such complexes, in addition to those described above for the GST-immobilized complexes, include immunodetection of complexes using antibodies reactive with MGAT-X1 or target molecule, as well as enzyme-linked assays which rely on detecting an enzymatic activity associated with MGAT-X1 or target molecule.

The screening assay can also involve monitoring the expression of MGAT-X1. For example, regulators of expression of MGAT-X1 can be identified in a method in which a cell is contacted with a candidate compound and the expression of MGAT-X1 protein or mRNA in the cell is determined. The level of expression of MGAT-X1 protein or mRNA the presence of the candidate compound is compared to the level of expression of MGAT-X1 protein or mRNA in the absence of the candidate Compound. The candidate compound can then be identified as a regulator of expression of MGAT-X1 based on this comparison. For example, when expression of MGAT-X1 protein or mRNA protein is greater (statistically significantly greater) in the presence of the candidate compound than in its absence, the candidate compound is identified as a stimulator of MGAT-X1 protein or mRNA expression. Alternatively, when expression of MGAT-X1 protein or mRNA is less (statistically significantly less) in the presence of the candidate compound than in its absence, the candidate compound is identified as an inhibitor of MGAT-X1 protein or mRNA expression. The level of MGAT-X1 protein or mRNA expression in the cells can be determined by methods described below.

Binding Assays

For binding assays, the test compound is preferably a small molecule which binds to and occupies the active site of MGAT-X1 transferase polypeptide, thereby making the ligand binding site inaccessible to substrate such that normal biological activity is prevented. Examples of such small molecules include, but are not limited to, small peptides or peptide-like molecules. Potential ligands which bind to a polypeptide of the invention include, but are not limited to, the natural ligands of known MGAT-X1 transferase and analogues or derivatives thereof.

In binding assays, either the test compound or the MGAT-X1 transferase polypeptide can comprise a detectable label, such as a fluorescent, radioisotopic, chemiluminescent, or enzymatic label, such as horseradish peroxidase, alkaline phosphatase, or luciferase. Detection of a test compound which is bound to MGAT-X1 transferase polypeptide can then be accomplished, for example, by direct counting of radioemmission, by scintillation counting, or by determining conversion of an appropriate substrate to a detectable product. Alternatively, binding of a test compound to a MGAT-X1 transferase polypeptide can be determined without labeling either of the interactants. For example, a microphysiometer can be used to detect binding of a test compound with a MGAT-X1 transferase polypeptide. A microphysiometer (e.g., Cytosensor™) is an analytical instrument that measures the rate at which a cell acidifies its environment using a light-addressable potentiometric sensor (LAPS). Changes in this acidification rate can be used as an indicator of the interaction between a test compound and MGAT-X1 [Haseloff et al. (1988)].

Determining the ability of a test compound to bind to MGAT-X1 also can be accomplished using a technology such as real-time Bimolecular Interaction Analysis (BIA) [McConnell et al. (1992), Sjolander & Urbaniczky (1991)]. BIA is a technology for studying biospecific interactions in real time, without labeling any of the interactants (e.g., BIAcore™). Changes in the optical phenomenon surface plasmon resonance (SPR) can be used as an indication of real-time reactions between biological molecules.

In yet another aspect of the invention, a MGAT-X1-like polypeptide can be used as a "bait protein" in a two-hybrid assay or three-hybrid assay [Szabo et al., (1995); Zervos et al. (1993); Madura et al. (1993); Bartel et al. (1993)]; U.S. Pat. No. 5,283,317), to identify other proteins which bind to or interact with MGAT-X1 and modulate its activity.

The two-hybrid system is based on the modular nature of most transcription factors, which consist of separable DNA-binding and activation domains. Briefly, the assay utilizes two different DNA constructs. For example, in one construct, polynucleotide encoding MGAT-X1 can be fused to a polynucleotide encoding the DNA binding domain of a known transcription factor (e.g., GAL-4). In the other construct a DNA sequence that encodes an unidentified protein ("prey" or "sample") can be fused to a polynucleotide that codes for the activation domain of the known transcription factor. If the "bait" and the "prey" proteins are able to interact in vivo to form an protein-dependent complex, the DNA-binding and activation domains of the transcription factor are brought into close proximity. This proximity allows transcription of a reporter gene (e.g., LacZ), which is operably linked to a transcriptional regulatory site responsive to the transcription factor. Expression of the reporter gene can be detected, and cell colonies containing the functional transcription factor can be isolated and used to obtain the DNA sequence encoding the protein which interacts with MGAT-X1.

It may be desirable to immobilize either the MGAT-X1 (or polynucleotide) or the test compound to facilitate separation of the bound form from unbound forms of one or both of the interactants, as well as to accommodate automation of the assay. Thus, either the MGAT-X1-like polypeptide (or polynucleotide) or the test compound can be bound to a solid support. Suitable solid supports include, but are not limited to, glass or plastic slides, tissue culture plates, microtiter wells, tubes, silicon chips, or particles such as beads (including, but not limited to, latex, polystyrene, or glass beads). Any method known in the art can be used to attach MGAT-X1-like polypeptide (or polynucleotide) or test compound to a solid support, including use of covalent and non-covalent linkages, passive absorption, or pairs of binding moieties attached respectively to the polypeptide (or polynucleotide) or test compound and the solid support. Test compounds are preferably bound to the solid support in an array, so that the location of individual test compounds can be tracked. Binding of a test compound to MGAT-X1 (or a polynucleotide encoding for MGAT-X1) can be accomplished in any vessel suitable for containing the reactants. Examples of such vessels include microtiter plates, test tubes, and microcentrifuge tubes.

In one embodiment, MGAT-X1 is a fusion protein comprising a domain that allows binding of MGAT-X1 to a solid support. For example, glutathione-S-transferase fusion proteins can be adsorbed onto glutathione sepharose beads (Sigma Chemical, St. Louis, Mo.) or glutathione derivatized microtiter plates, which are then combined with the test compound or the test compound and the non-adsorbed MGAT-X1; the mixture is then incubated under conditions conducive to complex formation (e.g., at physiological conditions for salt and pH). Following incubation, the beads or microtiter plate wells are washed to remove any unbound components. Binding of the interactants can be determined either directly or indirectly, as described above. Alternatively, the complexes can be dissociated from the solid support before binding is determined.

Other techniques for immobilizing proteins or polynucleotides on a solid support also can be used in the screening assays of the invention. For example, either MGAT-X1 (or a polynucleotide encoding MGAT-X1) or a test compound can be immobilized utilizing conjugation of biotin and streptavidin. Biotinylated MGAT-X1 (or a polynucleotide encoding biotinylated MGAT-X1) or test compounds can be prepared from biotin-NHS (N-hydroxysuccinimide) using techniques well known in the art (e.g., biotinylation kit, Pierce Chemicals, Rockford, Ill.) and immobilized in the wells of streptavidin-coated plates (Pierce Chemical). Alternatively, antibodies which specifically bind to MGAT-X1, polynucleotide, or a test compound, but which do not interfere with a desired binding site, such as the active site of MGAT-X1, can be derivatized to the wells of the plate. Unbound target or protein can be trapped in the wells by antibody conjugation.

Methods for detecting such complexes, in addition to those described above for the GST-immobilized complexes, include immunodetection of complexes using anti-bodies which specifically bind to MGAT-X1 transferase polypeptide or test compound, enzyme-linked assays which rely on detecting an activity of MGAT-X1 transferase polypeptide, and SDS gel electrophoresis under non-reducing conditions.

Screening for test compounds which bind to a MGAT-X1 transferase polypeptide or polynucleotide also can be carried out in an intact cell. Any cell which comprises a MGAT-X1 transferase polypeptide or polynucleotide can be used in a cell-based assay system. A MGAT-X1 transferase polynucleotide can be naturally occurring in the cell or can be introduced using techniques such as those described above. Binding of the test compound to MGAT-X1 or a polynucleotide encoding MGAT-X1 is determined as described above.

Functional Assays

Test compounds can be tested for the ability to increase or decrease MGAT-X1 activity of a MGAT-X1 transferase polypeptide. The MGAT-X1 activity can be measured, for example, using methods described in the specific examples, below. MGAT-X1 activity can be measured after contacting either a purified MGAT-X1, a cell membrane preparation, or an intact cell with a test compound. A test compound which decreases MGAT-X1 activity by at least about 10, preferably about 50, more preferably about 75, 90, or 100% is identified as a potential agent for decreasing MGAT-X1 activity. A test compound which increases MGAT-X1 activity by at least about 10, preferably about 50, more preferably about 75, 90, or 100% is identified as a potential agent for increasing MGAT-X1 activity.

One such screening procedure involves the use of melanophores which are transfected to express MGAT-X1. Such a screening technique is described in PCT WO 92/01810 published Feb. 6, 1992. Thus, for example, such an assay may be employed for screening for a compound which inhibits activation of the transferase polypeptide of the present invention by contacting the melanophore cells which encode the transferase with both the transferase ligand and a compound to be screened. Inhibition of the signal generated by the ligand indicates that a compound is a potential antagonist for the transferase, i.e., inhibits activation of the transferase. The screen may be employed for identifying a compound which activates the transferase by contacting such cells with compounds to be screened and determining whether each compound generates a signal, i.e., activates the transferase.

Other screening techniques include the use of cells which express MGAT-X1 (for example, transfected CHO cells) in a system which measures extracellular pH changes caused by transferase activation [Iwabuchi et al. (1993)]. For example, compounds may be contacted with a cell which expresses the transferase polypeptide of the present invention and a second messenger response, e.g., signal transduction or pH changes, can be measured to determine whether the potential compound activates or inhibits the transferase. Another such screening technique involves introducing RNA encoding MGAT-X1 into *Xenopus* oocytes to transiently express the transferase. The transferase oocytes can then be contacted with the transferase ligand and a compound to be screened, followed by detection of inhibition or activation of a calcium signal in the case of screening for compounds which are thought to inhibit activation of the transferase.

Gene Expression

In another embodiment, test compounds which increase or decrease MGAT-X1 gene expression are identified. As used herein, the term "correlates with expression of a "polynucleotide" indicates that the detection of the presence of nucleic acids, the same or related to a nucleic acid sequence encoding MGAT-X1, by northern analysis or realtime PCR is indicative of the presence of nucleic acids encoding MGAT-X1 in a sample, and thereby correlates with expression of the transcript from the polynucleotide encoding MGAT-X1. The term "microarray," as used herein, refers to an array of distinct polynucleotides or oligonucleotides arrayed on a substrate, such as paper, nylon or any other type of membrane, filter, chip, glass slide, or any other suitable solid support. A MGAT-X1 polynucleotide is contacted with a test compound, and the expression of an RNA or polypeptide product of MGAT-X1 polynucleotide is determined. The level of expression of appropriate mRNA or polypeptide in the presence of the test compound is compared to the level of expression of mRNA or polypeptide in the absence of the test compound. The test compound can then be identified as a regulator of expression based on this comparison. For example, when expression of mRNA or polypeptide is greater in the presence of the test compound than in its absence, the test compound is identified as a stimulator or enhancer of the mRNA or polypeptide expression. Alternatively, when expression of the mRNA or polypeptide is less in the presence of the test compound than in its absence, the test compound is identified as an inhibitor of the mRNA or polypeptide expression.

The level of MGAT-X1 mRNA or polypeptide expression in the cells can be determined by methods well known in the art for detecting mRNA or polypeptide. Either qualitative or quantitative methods can be used. The presence of polypeptide products of MGAT-X1 transferase polynucleotide can be determined, for example, using a variety of techniques known in the art, including immunochemical methods such as radioimmunoassay, Western blotting, and immunohistochemistry. Alternatively, polypeptide synthesis can be determined in vivo, in a cell culture, or in an in vitro translation system by detecting incorporation of labeled amino acids into MGAT-X1.

Such screening can be carried out either in a cell-free assay system or in an intact cell. Any cell which expresses MGAT-X1 polynucleotide can be used in a cell-based assay system. The MGAT-X1 polynucleotide can be naturally occurring in the cell or can be introduced using techniques such as those described above. Either a primary culture or an established cell line can be used.

Test Compounds

Suitable test compounds for use in the screening assays of the invention can be obtained from any suitable source, e.g., conventional compound libraries. The test compounds can also be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds [Lam et al. (1997)].

Examples of methods for the synthesis of molecular libraries can be found in the art [Lam et al. (1997); DeWitt et al. (1993); Erb et al. (1994); Zuckermann et al. (1994); Cho et al. (1993); Carrell et al. (1994) Angew. Chem. Int. Ed. Engl. 33:2059]. Libraries of compounds may be presented in solution. [Carrell et al. (1994), Angew. Chem. Int. Ed. Engl. 33: 2061; Gallop et al. (1994)] or on beads [Houghten et al. (1992)], chips [Cull et al. (1992)], bacteria (U.S. Pat. No. 5,223,409), spores (U.S. Pat. Nos. 5,571,698; 5,403,484; and 5,223,409), plasmids [Coruzzi et al. (1984)] or phage [Nagarenko et al. (1997); Felici et al. [1991]; Cwirla et al. (1990); Devlin et al. (1990); Sambrook et al. (1989)].

Modeling of Regulators

Computer modeling and searching technologies permit identification of compounds, or the improvement of already identified compounds, that can modulate MGAT-X1 expression or activity. Having identified such a compound or composition, the active sites or regions are identified. Such active sites might typically be ligand binding sites, such as the interaction domain of the ligand with MGAT-X1. The active site can be identified using methods known in the art including, for example, from the amino acid sequences of peptides, from the nucleotide sequences of nucleic acids, or from study of complexes of the relevant compound or composition with its natural ligand. In the latter case, chemical or X-ray crystallographic methods can be used to find the active site by finding where on the factor the complexed ligand is found.

Next, the three dimensional geometric structure of the active site is determined. This can be done by known methods, including X-ray crystallography, which can determine a complete molecular structure. On the other hand, solid or liquid phase NMR can be used to determine certain intramolecular distances. Any other experimental method of structure determination can be used to obtain partial or complete geometric structures. The geometric structures may be measured with a complexed ligand, natural or artificial, which may increase the accuracy of the active site structure determined.

If an incomplete or insufficiently accurate structure is determined, the methods of computer based numerical modeling can be used to complete the structure or improve its accuracy. Any recognized modeling method may be used, including parameterized models specific to particular biopolymers such as proteins or nucleic acids, molecular dynamics models based on computing molecular motions, statistical mechanics models based on thermal ensembles, or combined models. For most types of models, standard molecular force fields, representing the forces between constituent atoms and groups, are necessary, and can be selected from force fields known in physical chemistry. The incomplete or less accurate experimental structures can serve as constraints on the complete and more accurate structures computed by these modeling methods.

Finally, having determined the structure of the active site, either experimentally, by modeling, or by a combination, candidate modulating compounds can be identified by searching databases containing compounds along with information on their molecular structure. Such a search seeks compounds having structures that match the determined active site structure and that interact with the groups defining the active site. Such a search can be manual, but is preferably computer assisted. These compounds found from this search are potential MGAT-X1 modulating compounds.

Alternatively, these methods can be used to identify improved modulating compounds from an already known modulating compound or ligand. The composition of the known compound can be modified and the structural effects of modification can be determined using the experimental and computer modeling methods described above applied to the new composition. The altered structure is then compared to the active site structure of the compound to determine if an improved fit or interaction results. In this manner systematic variations in composition, such as by varying side groups, can be quickly evaluated to obtain modified modulating compounds or ligands of improved specificity or activity.

Therapeutic Indications and Methods

It was found by the present applicant that MGAT-X1 is expressed in different human tissues.

Dermatologic Disorders

The human MGAT_X1 is highly expressed in the following dermatological tissues: skin. The expression in the above mentioned tissues demonstrates that the human MGAT_X1 or mRNA can be utilized to diagnose of dermatological diseases. Additionally the activity of the human MGAT_X1 can be modulated to treat those diseases.

The skin serves several functions. It's an multi-layered organ system that builds an effective protective cover and regulates body temperature, senses painful and pleasant stimuli, keeps substances from entering the body, and provides a shield from the sun's harmful effects. Skin color, texture, and folds help mark people as individuals. Thus, skin disorders or diseases often have important consequences for physical and mental health. Skin disorders include, but are not limited to the conditions described in the following.

Itching (pruritus) is a sensation that instinctively demands scratching, which may be caused by a skin condition or a systemic disease.

Superficial Skin Disorders affect the uppermost layer of the skin, the stratum corneum or the keratin layer, and it consists of many layers of flattened, dead cells and acts as a barrier to protect the underlying tissue from injury and infection. Disorders of the superficial skin layers involve the stratum corneum and deeper layers of the epidermis.

Examples of superficial skin disorders are provided in the following.

Dry skin often occurs in people past middle age, severe dry skin (ichthyosis) results from an inherited scaling disease, such as ichthyosis vulgaris or epidermolytic hyperkeratosis. Ichthyosis also results from nonhereditary disorders, such as leprosy, underactive thyroid, lymphoma, AIDS, and sarcoidosis.

Keratosis pilaris is a common disorder in which dead cells shed from the upper layer of skin and form plugs that fill the openings of hair follicles.

A callus is an area on the stratum corneum or keratin layer, that becomes abnormally thick in response to repeated rubbing.

A corn is a pea-sized, thickened area of keratin that occurs on the feet.

Psoriasis is a chronic, recurring disease recognizable by silvery scaling bumps and various-sized plaques (raised patches). An abnormally high rate of growth and turnover of skin cells causes the scaling.

Pityriasis rosea is a mild disease that causes scaly, rose-colored, inflamed skin. Pityriasis rosea is possibly caused by an infectious agent, although none has been identified.

Lichen planus, a recurring itchy disease, starts as a rash of small discrete bumps that then combine and become rough, scaly plaques (raised patches).

Dermatitis (eczema) is an inflammation of the upper layers of the skin, causing blisters, redness, swelling, oozing, scabbing, scaling, and usually itching.

Forms of dermatitis are contact dermatitis, or chronic dermatitis of the hands and feet, e.g. Pompholyx.

Further examples of dermatitic disorders are atopic dermatitis, seborrheic dermatitis, nummular dermatitis, generalized exfoliative dermatitis, stasis dermatitis, or localized scratch dermatitis (lichen simplex chronicus, neurodermatitis).

Other skin disorders are caused by inflammation. The skin can break out in a variety of rashes, sores, and blisters. Some skin eruptions can even be life threatening.

Drug rashes are side effects of medications, mainly allergic reactions to medications.

Toxic epidermal necrolysis is a life-threatening skin disease in which the top layer of the skin peels off in sheets. This condition can be caused by a reaction to a drug, or by some other serious disease.

Erythema multiforme, often caused by herpes simplex is a disorder characterized by patches of red, raised skin that often look like targets and usually are distributed symmetrically over the body.

Erythema nodosum is an inflammatory disorder that produces tender red bumps (nodules) under the skin, most often over the shins but occasionally on the arms and other areas.

Granuloma annulare is a chronic skin condition of unknown cause in which small, firm, raised bumps form a ring with normal or slightly sunken skin in the center.

Some skin disorders are characterized as blistering diseases. Three autoimmune diseases—pemphigus, bullous pemphigoid, and dermatitis herpetiformis—are among the most serious.

Pemphigus is an uncommon, sometimes fatal, disease in which blisters (bullae) of varying sizes break out on the skin, the lining of the mouth, and other mucous membranes.

Bullous pemphigoid is an autoimmune disease that causes blistering.

Dermatitis herpetiformis is an autoimmune disease in which clusters of intensely itchy, small blisters and hive-like swellings break out and persist. In people with the disease, proteins in wheat, rye, barley, and oat products activate the immune system, which attacks parts of the skin and somehow causes the rash and itching.

Sweating disorders also belong to skin disorders.

Prickly heat is an itchy skin rash caused by trapped sweat.

Excessive sweating (hyperhidrosis) may affect the entire surface of the skin, but often it's limited to the palms, soles, armpits, or groin. The affected area is often pink or bluish white, and in severe cases the skin may be cracked, scaly, and soft, especially on the feet.

Skin disorders can affect the sebaceous glands. The sebaceous glands, which secrete oil onto the skin, lie in the dermis, the skin layer just below the surface layer (epidermis). Sebaceous gland disorders include acne, rosacea, perioral dermatitis, and sebaceous cysts.

Acne is a common skin condition in which the skin pores become clogged, leading to pimples and inflamed, infected abscesses (collections of pus). Acne tends to develop in teenagers.

Acne is further subdivided in superficial acne or deep acne.

Rosacea is a persistent skin disorder that produces redness, tiny pimples, and broken blood vessels, usually on the central area of the face.

Perioral dermatitis is a red, often bumpy rash around the mouth and on the chin.

A sebaceous cyst (keratinous cyst) is a slow-growing bump containing dead skin, skin excretions, and other skin particles. These cysts may be small and can appear anywhere.

Hair Disorders also are skin disorders. Hair disorders include excessive hairiness, baldness, and ingrown beard hairs.

The skin can be infected by bacteria. Bacterial skin infections can range in seriousness from minor acne to a life-threatening condition, such as staphylococcal scalded skin syndrome. The most common bacterial skin infections are caused by *Staphylococcus* and *Streptococcus*. Risk factors for skin infections are for example diabetes, AIDS or skin lesions.

Impetigo is a skin infection, caused by *Staphylococcus* or *Streptococcus*, leading to the formation of small pus-filled blisters (pustules).

Folliculitis is an inflammation of the hair follicles caused by infection with *Staphylococcus*. The infection damages the hairs, which can be easily pulled out.

Boils (furuncles) are large, tender, swollen, raised areas caused by staphylococcal infection around hair follicles.

Carbuncles are clusters of boils that result in extensive sloughing of skin and scar formation. Carbuncles develop and heal more slowly than single boils and may lead to fever and fatigue.

Erysipelas is a skin infection caused by *Streptococcus*. A shiny, red, slightly swollen, tender rash develops, often with small blisters. Lymph nodes around the infected area may become enlarged and painful.

Cellulitis is a spreading infection in, and sometimes beneath, the deep layers of the skin. Cellulitis most often results from a streptococcal infection or a staphylococcal infection. However, many other bacteria can also cause cellulitis.

Paronychia is an infection around the edge of a fingernail or toenail. Paronychia can be caused by many different bacteria, including *Pseudomonas* and *Proteus*, and by fungi, such as *Candida*.

Staphylococcal scalded skin syndrome is a widespread skin infection that can lead to toxic shock syndrome, in which the skin peels off as though burned. Certain types of staphylococci produce a toxic substance that causes the top layer of skin (epidermis) to split from the rest of the skin.

Erythrasma is an infection of the top layers of the skin by the bacterium *Corynebacterium minutissimum*.

Skin infections are often caused by fungi. Fungi that infect the skin (dermatophytes) live only in the dead, topmost layer (stratum corneum) and don't penetrate deeper. Some fungal infections cause no symptoms or produce only a small amount of irritation, scaling, and redness. Other fungal infections cause itching, swelling, blisters, and severe scaling.

Ringworm is a fungal skin infection caused by several different fungi and generally classified by its location on the body.

Examples are Athlete's foot (foot ringworm, caused by either *Trichophyton* or *Epidermophyton*), jock itch (groin ringworm, can be caused by a variety of fungi and yeasts), scalp ringworm, caused by *Trichophyton* or *Microsporum*), nail ringworm and body ringworm (caused by *Trichophyton*).

Candidiasis (yeast infection, moniliasis) is an infection by the yeast *Candida*. *Candida* usually infects the skin and mucous membranes, such as the lining of the mouth and vagina. Rarely, it invades deeper tissues as well as the blood, causing life-threatening systemic candidiasis. The following types of candida infections can be distinguished: Infections in skinfolds (intertriginous infections), vaginal and penile candida infections (vulvovaginitis), thrush, Perlèche (candida infection at the corners of the mouth), candidal paronychia (candida growing in the nail beds, produces painful swelling and pus).

Tinea versicolor is a fungal infection that causes white to light brown patches on the skin.

The skin can also be affected by parasites, mainly tiny insects or worms.

Scabies is a mite infestation that produces tiny reddish pimples and severe itching. Scabies is caused by the itch mite *Sarcoptes scabiei*.

Lice infestation (pediculosis) causes intense itching and can affect almost any area of the skin. Head lice and pubic lice are two different species.

Creeping eruption (cutaneous larva migrans) is a hookworm infection transmitted from warm, moist soil to exposed skin. The infection is caused by a hookworm that normally inhabits dogs and cats.

Many types of viruses invade the skin. The medically important once cause warts and cold sores (fever blisters) on the lip. Warts are caused by the papillomavirus, and cold sores are caused by the herpes simplex virus. Another important group of viruses that infect the skin belongs to the poxvirus family. Chickenpox remains a common childhood infection. A poxvirus also causes molluscum contagiosum, which is an infection of the skin by a poxvirus that causes skin-colored, smooth, waxy bumps.

Sunlight can cause severe skin damage. Sunburn results from an overexposure to ultraviolet B (UVB) rays. Some sunburned people develop a fever, chills, and weakness, and those with very bad sunburns even may go into shock—low blood pressure, and fainting.

People who are in the sun a lot have an increased risk of skin cancers, including squamous cell carcinoma, basal cell carcinoma, and to some degree, malignant melanoma.

Drugs, among other causes, can cause skin photosensitivity reactions which can occur after only a few minutes of sun exposure. These reactions include redness, peeling, hives, blisters, and thickened, scaling patches (photosensitivity).

Some skin disorders are characterized as Pigment Disorders.

Albinism is a rare, inherited disorder in which no melanin is formed.

Vitiligo is a condition in which a loss of melanocytes results in smooth, whitish patches of skin, which may occur after unusual physical trauma and tends to occur with certain other diseases, including Addison's disease, diabetes, pernicious anemia, and thyroid disease.

Tinea versicolor is a fungal infection of the skin that sometimes results in hyperpigmentation.

Melasma appears on the face (usually the forehead, cheeks, temples, and jaws) as a roughly symmetric group of dark brown patches of pigmentation that are often clearly delineated.

Skin growths, which are abnormal accumulations of different types of cells, may be present at birth or develop later. Noncancerous (benign) growth and cancerous (malignant) growth types are distinguished.

Moles (nevi) are small, usually dark, skin growths that develop from pigment-producing cells in the skin (melanocytes). Most moles are harmless. However, noncancerous moles can develop into malignant melanoma.

Skin tags are soft, small, flesh-colored or slightly darker skin flaps that appear mostly on the neck, in the armpits, or in the groin.

Lipomas are soft deposits of fatty material that grow under the skin, causing round or oval lumps.

Angiomas are collections of abnormally dense blood or lymph vessels that are usually located in and below the skin and that cause red or purple discolorations.

Examples of angiomas are port-wine stains, strawberry marks, cavernous hemangiomas, spider angiomas, and lymphangiomas.

Pyogenic granulomas are scarlet, brown, or blue-black slightly raised areas caused by increased growth of capillaries (the smallest blood vessels) and swelling of the surrounding tissue.

Seborrheic keratoses (sometimes called seborrheic warts) are flesh-colored, brown, or black growths that can appear anywhere on the skin.

Dermatofibromas are small, red-to-brown bumps (nodules) that result from an accumulation of fibroblasts, the cells that populate the soft tissue under the skin.

Keratoacanthomas are round, firm, usually flesh-colored growths that have an unusual central crater containing a pasty material.

Keloids are smooth, shiny, slightly pink, often dome-shaped, proliferative growths of fibrous tissue that form over areas of injury or over surgical wounds.

Skin cancer is the most common form of cancer, but most types of skin cancers are curable.

Basal cell carcinoma is a cancer that originates in the lowest layer of the epidermis.

Squamous cell carcinoma is cancer that originates in the middle layer of the epidermis.

Bowen's disease is a form of squamous cell carcinoma that's confined to the epidermis and hasn't yet invaded the underlying dermis.

Melanoma is a cancer that originates in the pigment-producing cells of the skin (melanocytes).

Kaposi's sarcoma is a cancer that originates in the blood vessels, usually of the skin.

Paget's disease is a rare type of skin cancer that looks like an inflamed, reddened patch of skin (dermatitis); it originates in glands in or under the skin.

Muscle-Skeleton Disorders

The human MGAT_X1 is highly expressed in the following muscle/skeleton tissues: cartilage, bone connective tissue, adipose. The expression in muscle/skleleton tissues demonstrates that the human MGAT_X1 or mRNA can be utilized to diagnose of diseases of the muscle/skeleton system. Additionally the activity of the human MGAT_X1 can be modulated to treat those diseases.

Components of the musculoskeletal system are skeleton, muscles, tendons, ligaments, and other components of joints. Disorders of the musculoskeletal system often cause chronic pain and physical disability. They range from injures, infsctions, inflammation or other types of disorders. Examples of musculoskeletal disorders are presented in the following.

Examples are osteoporosis, postmenopausal osteoporosis, senile osteoporosis, secondary osteoporosis, idiopathic juvenile osteoporosis, Paget's disease of the bone, osteochondromas (osteocartilaginous exostoses), tumors of the bone (benign chondromas, chondroblastomas, chondromyxoid fibromas, osteoid osteomas, giant cell tumors of the bone, multiple myeloma, osteosarcoma (osteogenic sarcoma), fibrosarcomas and malignant fibrous histiocytomas, chondrosarcomas, Ewing's tumor (Ewing's sarcoma), malignant lymphoma of bone (reticulum cell sarcoma, metastatic tumors of the bone), osteoarthritis, and gout and Pseudogout.

Examples of disorders of joints and connective tissue are rheumatoid arthritis, psoriatic arthritis, discoid lupus erythematosus, systemic lupus erythematosus, scleroderma (systemic sclerosis), Sjögren's syndrome, connective tissue disease, polymyositis and dermatomyositis, relapsing polychondritis, vasculitis, polyarteritis nodosa, polymyalgia rheumatica, temporal arteritis, Wegener's granulomatosis, Reiter's syndrome, Behçet's syndrome, ankylosing spondylitis, or Charcot's joints (neuropathic joint disease).

Eamples for bone and joint infections are osteomyelitis, and infectious arthritis.

Examples of disorders of muscles, bursas, and tendons are spasmodic torticollis, fibromyalgia syndromes (myofascial pain syndromes, fibromyositis), bursitis, tendinitis and tenosynovitis.

Foot problems are, for example ankle sprain, foot fractures, heel spurs, Sever's disease, posterior achilles tendon bursitis, anterior achilles tendon bursitis, posterior tibial neuralgia, pain in the ball of the foot (caused by damage to the nerves between the toes or to the joints between the toes and foot), onychomycosis, or nail discoloration.

Hematological Disorders

The human MGAT_X1 is highly expressed in the following tissues of the hematological system: erythrocytes, thrombocytes, bone marrow CD71+ cells, bone marrow CD33+ cells, bone marrow CD34+ cells, bone marrow CD15+ cells, cord blood CD71+ cells, cord blood CD34+ cells, neutrophils cord blood, T-cells peripheral blood CD4+, T-cells peripheral blood CD8+, monocytes peripheral blood CD14+, B-cells peripheral blood CD19+. The expression in the above mentioned tissues demonstrates that the human MGAT_X1 or mRNA can be utilized to diagnose of hematological diseases. Additionally the activity of the human MGAT_X1 can be modulated to treat hematological disorders.

Hematological disorders comprise diseases of the blood and all its constituents as well as diseases of organs involved in the generation or degradation of the blood. They include but are not limited to 1) Anemias, 2) Myeloproliferative Disorders, 3) Hemorrhagic Disorders, 4) Leukopenia, 5) Eosinophilic Disorders, 6) Leukemias, 7) Lymphomas, 8) Plasma Cell Dyscrasias, 9) Disorders of the Spleen in the course of hematological disorders, Disorders according to 1) include, but are not limited to anemias due to defective or deficient hem synthesis, deficient erythropoiesis. Disorders according to 2) include, but are not limited to polycythemia vera, tumor-associated erythrocytosis, myelofibrosis, thrombocythemia. Disorders according to 3) include, but are not limited to vasculitis, thrombocytopenia, heparin-induced thrombocytopenia, thrombotic thrombocytopenic purpura, hemolytic-uremic syndrome, hereditary and acquired disorders of platelet function, hereditary coagulation disorders. Disorders according to 4) include, but are not limited to neutropenia, lymphocytopenia. Disorders according to 5) include, but are not limited to hypereosinophilia, idiopathic hypereosinophilic syndrome. Disorders according to 6) include, but are not limited to acute myeloic leukemia, acute lymphoblastic leukemia, chronic myelocytic leukemia, chronic lymphocytic leukemia, myelodysplastic syndrome. Disorders according to 7) include, but are not limited to Hodgkin's disease, non-Hodgkin's lymphoma, Burkitt's lymphoma, mycosis fungoides cutaneous T-cell lymphoma. Disorders according to 8) include, but are not limited to multiple myeloma, macroglobulinemia, heavy chain diseases. In extension of the preceding idiopathic thrombocytopenic purpura, iron deficiency anemia, megaloblastic anemia (vitamin B12 deficiency), aplastic anemia, thalassemia, malignant lymphoma bone marrow invasion, malignant lymphoma skin invasion, haemolytic uraemic syndrome, giant platelet disease are considered to be hematological diseases too.

Cancer Disorders

The human MGAT_X1 is highly expressed in the following cancer tissues: colon tumor, ileum tumor, liver tumor, uterus tumor, breast tumor, prostate tumor. The expression in the above mentioned tissues and in particular the differential expression between diseased tissue colon tumor and healthy tissue colon, between diseased tissue ileum tumor and healthy tissue, between diseased tissue liver tumor and healthy tissue liver, between diseased tissue uterus tumor and healthy tissue uterus, between diseased tissue breast tumor and healthy tissue breast, between diseased tissue prostate tumor and healthy tissue prostata demonstrates that the human MGAT_X1 or mRNA can be utilized to diagnose of canter. Additionally the activity of the human MGAT_X1 can be modulated to treat cancer.

Cancer disorders within the scope of the invention comprise any disease of an organ or tissue in mammals characterized by poorly controlled or uncontrolled multiplication of normal or abnormal cells in that tissue and its effect on the body as a whole.

Cancer diseases within the scope of the invention comprise benign neoplasms, dysplasias, hyperplasias as well as neoplasms showing metastatic growth or any other transformations like e.g. leukoplakias which often precede a breakout of cancer. Cells and tissues are cancerous when they grow more rapidly than normal cells, displacing or spreading into the surrounding healthy tissue or any other tissues of the body described as metastatic growth, assume abnormal shapes and sizes, show changes in their nucleocytoplasmatic ratio, nuclear polychromasia, and finally may cease. Cancerous cells and tissues may affect the body as a whole when causing paraneoplastic syndromes or if cancer occurs within a vital organ or tissue, normal function will be impaired or halted, with possible fatal results. The ultimate involvement of a vital organ by cancer, either primary or metastatic, may lead to the death of the mammal affected. Cancer tends to spread, and the extent of its spread is usually related to an individual's chances of surviving the disease. Cancers are generally said to be in one of three stages of growth: early, or localized, when a tumor is still confined to the tissue of origin, or primary site; direct extension, where cancer cells from the tumour have invaded adjacent tissue or have spread only to regional lymph nodes; or metastasis, in which cancer cells have migrated to distant parts of the body from the primary site, via the blood or lymph systems, and have established secondary sites of infection. Cancer is said to be malignant because of its tendency to cause death if not treated. Benign tumors usually do not cause death, although they may if they interfere with a normal body function by virtue of their location, size, or paraneoplastic side effects. Hence benign tumors fall under the definition of cancer within the scope of the invention as well. In general, cancer cells divide at a higher rate than do normal cells, but the distinction between the growth of cancerous and normal tissues is not so much the rapidity of cell division in the former as it is the partial or complete loss of growth restraint in cancer cells and their failure to differentiate into a useful, limited tissue of the type that characterizes the functional equilibrium of growth of normal tissue. Cancer tissues may express certain molecular receptors and probably are influenced by the host's susceptibility and immunity and it is known that certain cancers of the breast and prostate, for example, are considered dependent on specific hormones for their existence. The term "cancer" under the scope of the invention is not limited to simple benign neoplasia but comprises any other benign and malign neoplasia like 1) Carcinoma, 2) Sarcoma, 3) Carcinosarcoma, 4) Cancers of the blood-forming tissues, 5) tumors of nerve tissues including the brain, 6) cancer of skin cells. Cancer according to 1) occurs in epithelial tissues, which cover the outer body (the skin) and line mucous membranes and the inner cavitary structures of organs e.g. such as the breast, lung, the respiratory and gastrointestinal tracts, the endocrine glands, and the genitourinary system. Ductal or glandular elements may persist in epithelial tumors, as in adenocarcinomas like e.g. thyroid adenocarcinoma, gastric adenocarcinoma, uterine adenocarcinoma. Cancers of the pavement-cell epithelium of the skin and of certain mucous membranes, such as e.g. cancers of the tongue, lip, larynx, urinary bladder, uterine cervix, or penis, may be termed epidermoid or squamous-cell carcinomas of the respective tissues and are in the scope of the definition of cancer as well. Cancer according to 2) develops in connective tissues, including fibrous tissues, adipose (fat) tissues, muscle, blood vessels, bone, and cartilage like e.g. osteogenic sarcoma; liposarcoma, fibrosarcoma, synovial sarcoma. Cancer according to 3) is cancer that develops in both epithelial and connective tissue. Cancer disease within the scope of this definition may be primary or secondary, whereby primary indicates that the cancer originated in the tissue where it is found rather than was established as a secondary site through metastasis from another lesion. Cancers and tumor diseases within the scope of this definition may be benign or malign and may affect all anatomical structures of the body of a mammal. By example but not limited to they comprise cancers and tumor diseases of I) the bone marrow and bone marrow derived cells (leukemias), II) the endocrine and exocrine glands like e.g. thyroid, parathyroid, pituitary, adrenal glands, salivary glands, pancreas III) the breast, like e.g. benign or malignant tumors in the mammary glands of either a male or a female, the mammary ducts, adenocarcinoma, medullary carcinoma, comedo carcinoma, Paget's disease of the nipple, inflammatory carcinoma of the young woman, IV) the lung, V) the stomach, VI) the liver and spleen, VII) the small intestine, VIII) the colon, IX) the bone and its supportive and connective tissues like malignant or benign bone tumour, e.g. malignant osteogenic sarcoma, benign osteoma, cartilage tumors; like malignant chondrosarcoma or benign chondroma; bone marrow tumors like malignant myeloma or benign eosinophilic granuloma, as well as metastatic tumors from bone tissues at other locations of the body; X) the mouth, throat, larynx, and the esophagus, XI) the urinary bladder and the internal and external organs and structures of the urogenital system of male and female like ovaries, uterus, cervix of the uterus, testes, and prostate gland, XII) the prostate, XIII) the pancreas, like ductal carcinoma of the pancreas; XIV) the lymphatic tissue like lymphomas and other tumors of lymphoid origin, XV) the skin, XVI) cancers and tumor diseases of all anatomical structures belonging to the respiration and respiratory systems including thoracal muscles and linings, XVII) primary or secondary cancer of the lymph nodes XVIII) the tongue and of the bony structures of the hard palate or sinuses, XVIV) the mouth, cheeks, neck and salivary glands, XX) the blood vessels including the heart and their linings, XXI) the smooth or skeletal muscles and their ligaments and linings, XXII) the peripheral, the autonomous, the central nervous system including the cerebellum, XXIII) the adipose tissue.

Urological Disorders

The human MGAT_X1 is highly expressed in the following urological tissues: spinal cord (ventral horn), spinal cord (dorsal horn), prostate tumor, penis, corpus cavernosum, fetal kidney. The expression in the above mentioned tissues demonstrates that the human MGAT_X1 or mRNA can be utilized to diagnose of urological disorders. Additionally the activity of the human MGAT_X1 can be modulated to treat urological disorders.

The human MGAT_X1 is highly expressed in spinal cord tissues: spinal cord (ventral horn), spinal cord (dorsal horn). Expression in spinal cord tissues demonstrates that the human MGAT_X1 or mRNA can be utilized to diagnose of incontinence as an urological disorder. The spinal cord tissues are involved in the neuronal regulation of the urological system. Additionally the activity of the human MGAT_X1 can be modulated to treat—but not limited to—incontinence.

Genitourological disorders comprise benign and malign disorders of the organs constituting the genitourological system of female and male, renal diseases like acute or chronic renal failure, immunologically mediated renal diseases like renal transplant rejection, lupus nephritis, immune complex renal diseases, glomerulopathies, nephritis, toxic nephropathy, obstructive uropathies like benign prostatic hyperplasia (BPH), neurogenic bladder syndrome, urinary incontinence like urge-, stress-, or overflow incontinence, pelvic pain, and erectile dysfunction.

Reproduction Disorders

The human MGAT_X1 is highly expressed in the following tissues of the reproduction system: uterus, uterus tumor, breast, breast tumor. The expression in the above mentioned tissues and in particular the differential expression between diseased tissue breast tumor and healthy tissue breast demonstrates that the human MGAT_X1 or mRNA can be utilized to diagnose of reproduction disorders. Additionally the activity of the human MGAT_X1 can be modulated to treat reproduction disorders.

Disorders of the male reproductive system include but are not limited to balanoposthitis, balanitis xerotica obliterans, phimosis, paraphimosis, erythroplasia of Queyrat, skin cancer of the penis, Bowen's and Paget's diseases, syphilis, herpes simplex infections, genital warts, molluscum contagiosum, priapism, peyronie's disease, benign prostatic hyperplasia (BPH), prostate cancer, prostatitis, testicular cancer, testicular torsion, inguinal hernia, epididymo-orchitis, mumps, hydroceles, spermatoceles, or varicoceles.

Impotence (erectile dysfunction) may results from vascular impairment, neurologic disorders, drugs, abnormalities of the penis, or psychologic problems.

Examples of disorders of the female reproductive include premature menopause, pelvic pain, vaginitis, vulvitis, vulvovaginitis, pelvic inflammatory disease, fibroids, menstrual disorders (premenstrual syndrome (PMS), dysmenorrhea, amenorrhea, primary amenorrhea, secondary amenorrhea, menorrhagia, hypomenorrhea, polymenorrhea, oligomenorrhea, metrorrhagia, menometrorrhagia, Postmenopausal bleeding), bleeding caused by a physical disorder, dysfunctional uterine bleeding, polycystic ovary syndrome (Stein-Leventhal syndrome), endometriosis, cancer of the uterus, cancer of the cervix, cancer of the ovaries, cancer of the vulva, cancer of the vagina, cancer of the fallopian tubes, hydatidiform mole.

Infertility may be caused by problems with sperm, ovulation, the fallopian tubes, and the cervix as well as unidentified factors.

Complications of pregnancy include miscarriage and stillbirth, ectopic pregnancy, anemia, Rh incompatibility, problems with the placenta, excessive vomiting, preeclampsia, eclampsia, and skin rashes (e.g. herpes gestationis, urticaria of pregnancy) as well as preterm labor and premature rupture of the membranes.

Breast disorders may be noncancerous (benign) or cancerous (malignant). Examples of breast disorders are but are not limited to breast pain, cysts, fibrocystic breast disease, fibrous lumps, nipple discharge, breast infection, breast cancer (ductal carcinoma, lobular carcinoma, medullary carcinoma, tubular carcinoma, and inflammatory breast cancer), Paget's disease of the nipple or Cystosarcoma phyllodes.

Neurological Disorders

The human MGAT_X1 is highly expressed in the following brain tissues: caudatum, posteroventral thalamus, dorsalmedial thalamus, hypothalamus, spinal cord (ventral horn), spinal cord (dorsal horn), neural progenitor cells, retina. The expression in brain tissues demonstrates that the human MGAT_X1 or mRNA can be utilized to diagnose nervous system diseases. Additionally the activity of the human MGAT_X1 can be modulated to treat nervous system diseases.

CNS disorders include disorders of the central nervous system as well as disorders of the peripheral nervous system. CNS disorders include, but are not limited to brain injuries, cerebrovascular diseases and their consequences, Parkinson's disease, corticobasal degeneration, motor neuron disease, dementia, including ALS, multiple sclerosis, traumatic brain injury, stroke, post-stroke, post-traumatic brain injury, and small-vessel cerebrovascular disease. Dementias, such as Alzheimer's disease, vascular dementia, dementia with Lewy bodies, frontotemporal dementia and Parkinsonism linked to chromosome 17, frontotemporal dementias, including Pick's disease, progressive nuclear palsy, corticobasal degeneration, Huntington's disease, thalamic degeneration, Creutzfeld-Jakob dementia, HIV dementia, schizophrenia with dementia, and Korsakoff's psychosis, within the meaning of the invention are also considered to be CNS disorders.

Similarly, cognitive-related disorders, such as mild cognitive impairment, age-associated memory impairment, age-related cognitive decline, vascular cognitive impairment, attention deficit disorders, attention deficit hyperactivity disorders, and memory disturbances in children with learning disabilities are also considered to be CNS disorders.

Pain, within the meaning of the invention, is also considered to be a CNS disorder. Pain can be associated with CNS disorders, such as multiple sclerosis, spinal cord injury, sciatica, failed back surgery syndrome, traumatic brain injury, epilepsy, Parkinson's disease, post-stroke, and vascular lesions in the brain and spinal cord (e.g., infarct, hemorrhage, vascular malformation). Non-central neuropathic pain includes that associated with post mastectomy pain, phantom feeling, reflex sympathetic dystrophy (RSD), trigeminal neuralgiaradioculopathy, post-surgical pain, HIV/AIDS related pain, cancer pain, metabolic neuropathies (e.g., diabetic neuropathy, vasculitic neuropathy secondary to connective tissue disease), paraneoplastic polyneuropathy associated, for example, with carcinoma of lung, or leukemia, or lymphoma, or carcinoma of prostate, colon or stomach, trigeminal neuralgia, cranial neuralgias, and post-herpetic neuralgia. Pain associated with peripheral nerve damage, central pain (i.e. due to cerebral ischemia) and various chronic pain i.e., lumbago, back pain (low back pain), inflammatory and/or rheumatic pain. Headache pain (for example, migraine with aura, migraine without aura, and other migraine disorders), episodic and chronic tension-type headache, tension-type like headache, cluster headache, and chronic paroxysmal hemicrania are also CNS disorders Visceral pain such as pancreatits, intestinal cystitis, dysmenorrhea, irritable Bowel syndrome, Crohn's disease, biliary colic, ureteral colic, myocardial infarction and pain syndromes of the pelvic cavity, e.g., vulvodynia, orchialgia, urethral syndrome and protatodynia are also CNS disorders. Also considered to be a disorder of the nervous system are acute pain, for example postoperative pain, and pain after trauma.

Metabolic Diseases

The human MGAT_X1 is highly expressed in the following metabolic disease related tissues: cartilage. The expression in the above mentioned tissues demonstrates that the human MGAT_X1 or mRNA can be utilized to diagnose of metabolic diseases. Additionally the activity of the human MGAT_X1 can be modulated to treat metabolic diseases.

Metabolic diseases are defined as conditions which result from an abnormality in any of the chemical or biochemical transformations and their regulating systems essential to producing energy, to regenerating cellular constituents, to eliminating unneeded products arising from these processes, and to regulate and maintain homeostasis in a mammal regardless of whether acquired or the result of a genetic transformation. Depending on which metabolic pathway is involved, a single defective transformation or disturbance of its regulation may produce consequences that are narrow, involving a single body function, or broad, affecting many organs, organ-systems or the body as a whole. Diseases resulting from abnormalities related to the fine and coarse mechanisms that affect each individual transformation, its rate and direction or the availability of substrates like amino acids, fatty acids, carbohydrates, minerals, cofactors, hormones, regardless whether they are inborn or acquired, are well within the scope of the definition of a metabolic disease according to this application.

Metabolic diseases often are caused by single defects in particular biochemical pathways, defects that are due to the deficient activity of individual enzymes or molecular transferases leading to the regulation of such enzymes. Hence in a broader sense disturbances of the underlying genes, their products and their regulation lie well within the scope of this definition of a metabolic disease. For example, but not limited to, metabolic diseases may affect 1) biochemical processes and tissues ubiquitous all over the body, 2) the bone, 3) the nervous system, 4) the endocrine system, 5) the muscle including the heart, 6) the skin and nervous tissue, 7) the urogenital system, 8) the homeostasis of body systems like water and electrolytes. For example, but not limited to, metabolic diseases according to 1) comprise obesity, amyloidosis, disturbances of the amino acid metabolism like branched chain disease, hyperaminoacidemia, hyperaminoaciduria, disturbances of the metabolism of urea, hyperammonemia, mucopolysaccharidoses e.g. Maroteaux-Lamy syndrome, storage diseases like glycogen storage diseases and lipid storage diseases, glycogenosis diseases like Cori's disease, malabsorption diseases like intestinal carbohydrate malabsorption, oligosaccharidase deficiency like maltase-, lactase-, sucrase-insufficiency, disorders of the metabolism of fructose, disorders of the metabolism of galactose, galactosaemia, disturbances of carbohydrate utilization like diabetes, hypoglycemia, disturbances of pyruvate metabolism, hypolipidemia, hypolipoproteinemia, hyperlipidemia, hyperlipoproteinemia, carnitine or carnitine acyltransferase deficiency, disturbances of the porphyrin metabolism, porphyrias, disturbances of the purine metabolism, lysosomal diseases, metabolic diseases of nerves and nervous systems like gangliosidoses, sphingolipidoses, sulfatidoses, leucodystrophies, Lesch-Nyhan syndrome. For example, but not limited to, metabolic diseases according to 2) comprise osteoporosis, osteomalacia like osteoporosis, osteopenia, osteogenesis imperfecta, osteopetrosis, osteonecrosis, Paget's disease of bone, hypophosphatemia. For example, but not limited to, metabolic diseases according to 3) comprise cerebellar dysfunction, disturbances of brain metabolism like dementia, Alzheimer's disease, Huntington's chorea, Parkinson's disease, Pick's disease, toxic encephalopathy, demyelinating neuropathies like inflammatory neuropathy, Guillain-Barré syndrome. For example, but not limited to, metabolic diseases according to 4) comprise primary and secondary metabolic disorders associated with hormonal defects like any disorder stemming from either an hyperfunction or hypofunction of some hormone-secreting endocrine gland and any combination thereof. They comprise Sipple's syndrome, pituitary gland dysfunction and its effects on other endocrine glands, such as the thyroid, adrenals, ovaries, and testes, acromegaly, hyper- and hypothyroidism, euthyroid goiter, euthyroid sick syndrome, thyroiditis, and thyroid cancer, over- or underproduction of the adrenal steroid hormones, adrenogenital syndrome, Cushing's syndrome, Addison's disease of the adrenal cortex, Addison's pernicious anemia, primary and secondary aldosteronism, diabetes insipidus, carcinoid syndrome, disturbances caused by the dysfunction of the parathyroid glands, pancreatic islet cell dysfunction, diabetes, disturbances of the endocrine system of the female like estrogen deficiency, resistant ovary syndrome. For example, but not limited to, metabolic diseases according to 5) comprise muscle weakness, myotonia, Duchenne's and other muscular dystrophies, dystrophia myotonica of Steinert, mitochondrial myopathies like disturbances of the catabolic metabolism in the muscle, carbohydrate and lipid storage myopathies, glycogenoses, myoglobinuria, malignant hyperthermia, polymyalgia rheumatica, dermatomyositis, primary myocardial disease, cardiomyopathy. For example, but not limited to, metabolic diseases according to 6) comprise disorders of the ectoderm, neurofibromatosis, scleroderma and polyarteritis, Louis-Bar syndrome, von Hippel-Lindau disease, Sturge-Weber syndrome, tuberous sclerosis, amyloidosis, porphyria. For example, but not limited to, metabolic diseases according to 7) comprise sexual dysfunction of the male and female. For example, but not limited to, metabolic diseases according to 8) comprise confused states and seizures due to inappropriate secretion of antidiuretic hormone from the pituitary gland, Liddle's syndrome, Bartter's syndrome, Fanconi's syndrome, renal electrolyte wasting, diabetes insipidus.

Cardiovascular Disorders

The human MGAT_X1 is highly expressed in the following cardiovascular related tissues: heart, pericardium, fetal aorta, aorta valve, artery, vein, pulmonic valve, liver tumor, thrombocytes, adipose, fetal kidney. Expression in the above mentioned tissues demonstrates that the human MGAT_X1 or mRNA can be utilized to diagnose of cardiovascular diseases. Additionally the activity of the human MGAT_X1 can be modulated to treat cardiovascular diseases.

The human MGAT_X1 is highly expressed in liver tissues: liver tumor. Expression in liver tissues demonstrates that the human MGAT_X1 or mRNA can be utilized to diagnose of dyslipidemia disorders as an cardiovascular disorder. Additionally the activity of the human MGAT_X1 can be modulated to treat—but not limited to—dyslipidemia disorders.

The human MGAT_X1 is highly expressed in adipose tissues. Expression in adipose demonstrates that the human MGAT_X1 or mRNA can be utilized to diagnose of dyslipidemia diseases as an cardiovascular disorder. Additionally the activity of the human MGAT_X1 can be modulated to treat—but not limited to—dyslipidemia diseases.

The human MGAT_X1 is highly expressed in kidney tissues: fetal kidney. Expression in kidney tissues demonstrates that the human MGAT_X1 or mRNA can be utilized to diagnose of blood pressure disorders as an cardiovascular disorder. Additionally the activity of the human MGAT_X1 can be modulated to treat—but not limited to—blood pressure disorders as hypertension or hypotension.

Heart failure is defined as a pathophysiological state in which an abnormality of cardiac function is responsible for the failure of the heart to pump blood at a rate commensurate with the requirement of the metabolizing tissue. It includes all forms of pumping failures such as high-output and low-output, acute and chronic, right-sided or left-sided, systolic or diastolic, independent of the underlying cause.

Myocardial infarction (MI) is generally caused by an abrupt decrease in coronary blood flow that follows a thrombotic occlusion of a coronary artery previously narrowed by arteriosclerosis. MI prophylaxis (primary and secondary prevention) is included as well as the acute treatment of MI and the prevention of complications.

Ischemic diseases are conditions in which the coronary flow is restricted resulting in a perfusion which is inadequate to meet the myocardial requirement for oxygen. This group of diseases includes stable angina, unstable angina and asymptomatic ischemia.

Arrhythmias include all forms of atrial and ventricular tachyarrhythmias, atrial tachycardia, atrial flutter, atrial fibrillation, atrio-ventricular reentrant tachycardia, preexitation syndrome, ventricular tachycardia, ventricular flutter, ventricular fibrillation, as well as bradycardic forms of arrhythmias.

Hypertensive vascular diseases include primary as well as all kinds of secondary arterial hypertension, renal, endocrine, neurogenic, others. The genes may be used as drug targets for the treatment of hypertension as well as for the prevention of all complications arising from cardiovascular diseases.

Peripheral vascular diseases are defined as vascular diseases in which arterial and/or venous flow is reduced resulting in an imbalance between blood supply and tissue oxygen demand. It includes chronic peripheral arterial occlusive disease (PAOD), acute arterial thrombosis and embolism, inflammatory vascular disorders, Raynaud's phenomenon and venous disorders.

Atherosclerosis is a cardiovascular disease in which the vessel wall is remodeled, compromising the lumen of the vessel. The atherosclerotic remodeling process involves accumulation of cells, both smooth muscle cells and monocyte/macrophage inflammatory cells, in the intima of the vessel wall. These cells take up lipid, likely from the circulation, to form a mature atherosclerotic lesion. Although the formation of these lesions is a chronic process, occurring over decades of an adult human life, the majority of the morbidity associated with atherosclerosis occurs when a lesion ruptures, releasing thrombogenic debris that rapidly occludes the artery. When such an acute event occurs in the coronary artery, myocardial infarction can ensue, and in the worst case, can result in death.

The formation of the atherosclerotic lesion can be considered to occur in five overlapping stages such as migration, lipid accumulation, recruitment of inflammatory cells, proliferation of vascular smooth muscle cells, and extracellular matrix deposition. Each of these processes can be shown to occur in man and in animal models of atherosclerosis, but the relative contribution of each to the pathology and clinical significance of the lesion is unclear.

Thus, a need exists for therapeutic methods and agents to treat cardiovascular pathologies, such as atherosclerosis and other conditions related to coronary artery disease.

Cardiovascular diseases include but are not limited to disorders of the heart and the vascular system like congestive heart failure, myocardial infarction, ischemic diseases of the heart, all kinds of atrial and ventricular arrhythmias, hypertensive vascular diseases, peripheral vascular diseases, and atherosclerosis.

Too high or too low levels of fats in the bloodstream, especially cholesterol, can cause long-term problems. The risk to develop atherosclerosis and coronary artery or carotid artery disease (and thus the risk of having a heart attack or stroke) increases with the total cholesterol level increasing. Nevertheless, extremely low cholesterol levels may not be healthy. Examples of disorders of lipid metabolism are hyperlipidemia (abnormally high levels of fats (cholesterol, triglycerides, or both) in the blood, may be caused by family history of hyperlipidemia, obesity, a high-fat diet, lack of exercise, moderate to high alcohol consumption, cigarette smoking, poorly controlled diabetes, and an underactive thyroid gland), hereditary hyperlipidemias (type I hyperlipoproteinemia (familial hyperchylomicronemia), type II hyperlipoproteinemia (familial hypercholesterolemia), type III hyperlipoproteinemia, type IV hyperlipoproteinemia, or type V hyperlipoproteinemia), hypolipoproteinemia, dyslipidemia, lipidoses (caused by abnormalities in the enzymes that metabolize fats), Gaucher's disease, Niemann-Pick disease, Fabry's disease, Wolman's disease, cerebrotendinous xanthomatosis, sitosterolemia, Refsum's disease, or Tay-Sachs disease.

Kidney disorders may lead to hyper or hypotension. Examples for kidney problems possibly leading to hypertension are renal artery stenosis, pyelonephritis, glomerulonephritis, kidney tumors, polycistic kidney disease, injury to the kidney, or radiation therapy affecting the kidney. Excessive urination may lead to hypotension.

Gastrointestinal and Liver Diseases

The human MGAT_X1 is highly expressed in the following tissues of the gastroenterological system: colon, colon tumor, ileum, ileum tumor, rectum, liver tumor. The expression in the above mentioned tissues demonstrates that the human MGAT_X1 or mRNA can be utilized to diagnose of gastroenterological disorders. Additionally the activity of the human MGAT_X1 can be modulated to treat gastroenterological disorders.

Gastrointestinal diseases comprise primary or secondary, acute or chronic diseases of the organs of the gastrointestinal tract which may be acquired or inherited, benign or malignant or metaplastic, and which may affect the organs of the gastrointestinal tract or the body as a whole. They comprise but are not limited to 1) disorders of the esophagus like achalasia, vigoruos achalasia, dysphagia, cricopharyngeal incoordination, pre-esophageal dysphagia, diffuse esophageal spasm, globus sensation, Barrett's metaplasia, gastroesophageal reflux, 2) disorders of the stomach and duodenum like functional dyspepsia, inflammation of the gastric mucosa, gastritis, stress gastritis, chronic erosive gastritis, atrophy of gastric glands, metaplasia of gastric tissues, gastric ulcers, duodenal ulcers, neoplasms of the stomach, 3) disorders of the pancreas like acute or chronic pancreatitis, insufficiency of the exocrinic or endocrinic tissues of the pancreas like steatorrhea, diabetes, neoplasms of the exocrine or endocrine pancreas like 3.1) multiple endocrine neoplasia syndrome, ductal adenocarcinoma, cystadenocarcinoma, islet cell tumors, insulinoma, gastrinoma, carcinoid tumors, glucagonoma, Zollinger-Ellison syndrome, Vipoma syndrome, malabsorption syndrome, 4) disorders of the bowel like chronic inflammatory diseases of the bowel, Crohn's disease, ileus, diarrhea and constipation, colonic inertia, megacolon, malabsorption syndrome, ulcerative colitis, 4.1) functional bowel disorders like irritable bowel syndrome, 4.2) neoplasms of the bowel like familial polyposis, adenocarcinoma, primary malignant lymphoma, carcinoid tumors, Kaposi's sarcoma, polyps, cancer of the colon and rectum.

Liver diseases comprise primary or secondary, acute or chronic diseases or injury of the liver which may be acquired or inherited, benign or malignant, and which may affect the liver or the body as a whole. They comprise but are not limited to disorders of the bilirubin metabolism, jaundice, syndroms of Gilbert's, Crigler-Najjar, Dubin-Johnson and Rotor; intrahepatic cholestasis, hepatomegaly, portal hypertension, ascites, Budd-Chiari syndrome, portal-systemic encephalopathy, fatty liver, steatosis, Reye's syndrome, liver diseases due to alcohol, alcoholic hepatitis or cirrhosis, fibrosis and cirrhosis, fibrosis and cirrhosis of the liver due to inborn errors of metabolism or exogenous substances, storage diseases, syndromes of Gaucher's, Zellweger's, Wilson's—disease, acute or chronic hepatitis, viral hepatitis and its variants, inflammatory conditions of the liver due to viruses, bacteria, fungi, protozoa, helminths; drug induced disorders of the liver, chronic liver diseases like primary sclerosing cholangitis, alpha1-antitrypsin-deficiency, primary biliary cirrhosis, postoperative liver disorders like postoperative intrahepatic cholestasis, hepatic granulomas, vascular liver disorders associated with systemic disease, benign or malignant neoplasms of the liver, disturbance of liver metabolism in the new-born or prematurely born.

Applications

The present invention provides for both prophylactic and therapeutic methods for dermatological diseases, urological diseases, muscle-skeleton disorders, hematological diseases, cancer, reproduction disorders, neurological diseases, metabolic diseases, cardiovascular diseases or gastroenterological diseases.

The regulatory method of the invention involves contacting a cell with an agent that modulates one or more of the activities of MGAT-X1. An agent that modulates activity can be an agent as described herein, such as a nucleic acid or a protein, a naturally-occurring cognate ligand of the polypeptide, a peptide, a peptidomimetic, or any small molecule. In one embodiment, the agent stimulates one or more of the biological activities of MGAT-X1. Examples of such stimulatory agents include the active MGAT-X1 and nucleic acid molecules encoding a portion of MGAT-X1. In another embodiment, the agent inhibits one or more of the biological activities of MGAT-X1. Examples of such inhibitory agents include antisense nucleic acid molecules and antibodies. These regulatory methods can be performed in vitro (e.g., by culturing the cell with the agent) or, alternatively, in vivo (e.g, by administering the agent to a subject). As such, the present invention provides methods of treating an individual afflicted with a disease or disorder characterized by unwanted expression or activity of MGAT-X1 or a protein in the MGAT-X1 signaling pathway. In one embodiment, the method involves administering an agent like any agent identified or being identifiable by a screening assay as described herein, or combination of such agents that modulate say upregulate or downregulate the expression or activity of MGAT-X1 or of any protein in the MGAT-X1 signaling pathway. In another embodiment, the method involves administering a regulator of MGAT-X1 as therapy to compensate for reduced or undesirably low expression or activity of MGAT-X1 or a protein in the MGAT-X1 signalling pathway.

Stimulation of activity or expression of MGAT-X1 is desirable in situations in which activity or expression is abnormally low and in which increased activity is likely to have a beneficial effect. Conversely, inhibition of activity or expression of MGAT-X1 is desirable in situations in which activity or expression of MGAT-X1 is abnormally high and in which decreasing its activity is likely to have a beneficial effect.

This invention is further illustrated by the following examples which should not be construed as limiting. The contents of all references, patents and published patent applications cited throughout this application are hereby incorporated by reference.

Pharmaceutical Compositions

This invention further pertains to novel agents identified by the above-described screening assays and uses thereof for treatments as described herein.

The nucleic acid molecules, polypeptides, and antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The invention includes pharmaceutical compositions comprising a regulator of MGAT-X1 expression or activity (and/or a regulator of the activity or expression of a protein in the MGAT-X1 signalling pathway) as well as methods for preparing such compositions by combining one or more such regulators and a pharmaceutically acceptable carrier. Also within the invention are pharmaceutical compositions comprising a regulator identified using the screening assays of the invention packaged with instructions for use. For regulators that are antagonists of MGAT-X1 activity or which reduce MGAT-X1 expression, the instructions would specify use of the pharmaceutical composition for treatment of dermatological diseases, urological diseases, muscle-skeleton disorders, hematological diseases, cancer, reproduction disorders, neurological diseases, metabolic diseases, cardiovascular diseases or gastroenterological diseases. For regulators that are agonists of MGAT-X1 activity or increase MGAT-X1 expression, the instructions would specify use of the pharmaceutical composition for treatment of dermatological diseases, urological diseases, muscle-skeleton disorders, hematological diseases, cancer, reproduction disorders, neurological diseases, metabolic diseases, cardiovascular diseases or gastroenterological diseases.

An antagonist of MGAT-X1 may be produced using methods which are generally known in the art. In particular, purified MGAT-X1 may be used to produce antibodies or to screen libraries of pharmaceutical agents to identify those which specifically bind MGAT-X1. Antibodies to MGAT-X1 may also be generated using methods that are well known in the art. Such antibodies may include, but are not limited to, polyclonal, monoclonal, chimeric, single chain antibodies, Fab fragments, and fragments produced by a Fab expression library. Neutralizing antibodies like those which inhibit dimer formation are especially preferred for therapeutic use.

In another embodiment of the invention, the polynucleotides encoding MGAT-X1, or any fragment or complement thereof, may be used for therapeutic purposes. In one aspect, the complement of the polynucleotide encoding MGAT-X1 may be used in situations in which it would be desirable to block the transcription of the mRNA. In particular, cells may be transformed with sequences complementary to polynucleotides encoding MGAT-X1. Thus, complementary molecules or fragments may be used to modulate MGAT-X1 activity, or to achieve regulation of gene function. Such technology is now well known in the art, and sense or antisense oligonucleotides or larger fragments can be designed from various locations along the coding or control regions of sequences encoding MGAT-X1.

Expression vectors derived from retroviruses, adenoviruses, or herpes or vaccinia viruses, or from various bacterial plasmids, may be used for delivery of nucleotide sequences to the targeted organ, tissue, or cell population. Methods which are well known to those skilled in the art can be used to construct vectors which will express nucleic acid sequence complementary to the polynucleotides of the gene encoding MGAT-X1. checklit: These techniques are described, for example, in [Scott and Smith (1990) Science 249:386-390].

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical composition containing MGAT-X1 in conjunction with a pharmaceutically acceptable carrier, for any of the therapeutic effects discussed above. Such pharmaceutical compositions may consist of MGAT-X1, antibodies to MGAT-X1, and mimetics, agonists, antagonists, or inhibitors of MGAT-X1. The compositions may be administered alone or in combination with at least one other agent, such as a stabilizing compound, which may be administered in any sterile, biocompatible pharmaceutical carrier including, but not limited to, saline, buffered saline, dextrose, and water. The compositions may be administered to a patient alone, or in combination with other agents, drugs or hormones.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL™ (BASF; Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, a pharmaceutically acceptable polyol like glycerol, propylene glycol, liquid polyetheylene glycol, and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin. Sterile injectable solutions can be prepared by incorporating the active compound (e.g., a polypeptide or antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed.

Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from a pressurized container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration. For pharmaceutical compositions which include an antagonist of MGAT-X1 activity, a compound which reduces expression of MGAT-X1, or a compound which reduces expression or activity of a protein in the MGAT-X1 signaling pathway or any combination thereof, the instructions for administration will specify use of the composition for dermatological diseases, urological diseases, muscle-skeleton disorders, hematological diseases, cancer, reproduction disorders, neurological diseases, metabolic diseases, cardiovascular diseases or gastroenterological diseases. For pharmaceutical compositions which include an agonist of MGAT-X1 activity, a compound which increases expression of MGAT-X1, or a compound which increases expression or activity of a protein in the MGAT-X1 signaling pathway or any combination thereof, the instructions for administration will specify use of the composition for dermatological diseases, urological diseases, muscle-skeleton disorders, hematological diseases, cancer, reproduction disorders, neurological diseases, metabolic diseases, cardiovascular diseases or gastroenterological diseases.

Diagnostics

In another embodiment, antibodies which specifically bind MGAT-X1 may be used for the diagnosis of disorders characterized by the expression of MGAT-X1, or in assays to monitor patients being treated with MGAT-X1 or agonists, antagonists, and inhibitors of MGAT-X1. Antibodies useful for diagnostic purposes may be prepared in the same manner as those described above for therapeutics. Diagnostic assays for MGAT-X1 include methods which utilize the antibody and a label to detect MGAT-X1 in human body fluids or in extracts of cells or tissues. The antibodies may be used with or without modification, and may be labeled by covalent or non-covalent joining with a reporter molecule. A wide variety of reporter molecules, several of which are described above, are known in the art and may be used.

A variety of protocols for measuring MGAT-X1, including ELISAs, RIAs, and FACS, are known in the art and provide a basis for diagnosing altered or abnormal levels of MGAT-X1 expression. Normal or standard values for MGAT-X1 expression are established by combining body fluids or cell extracts taken from normal mammalian subjects, preferably human, with antibody to MGAT-X1 under conditions suitable for complex formation The amount of standard complex formation may be quantified by various methods, preferably by photometric means. Quantities of MGAT-X1 expressed in subject samples from biopsied tissues are compared with the standard values. Deviation between standard and subject values establishes the parameters for diagnosing disease.

In another embodiment of the invention, the polynucleotides encoding MGAT-X1 may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of MGAT-X1 may be correlated with disease. The diagnostic assay may be used to distinguish between absence, presence, and excess expression of MGAT-X1, and to monitor regulation of MGAT-X1 levels during therapeutic intervention.

Polynucleotide sequences encoding MGAT-X1 may be used for the diagnosis of a dermatological diseases, urological diseases, muscle-skeleton disorders, hematological diseases, cancer, reproduction disorders, neurological diseases, metabolic diseases, cardiovascular diseases or gastroenterological diseases associated with expression of MGAT-X1. The polynucleotide sequences encoding MGAT-X1 may be used in Southern-, Northern-, or dot-blot analysis, or other membrane-based technologies; in PCR technologies; in dipstick, pin, and ELISA assays; and in microarrays utilizing fluids or tissues from patient biopsies to detect altered MGAT-X1 expression. Such qualitative or quantitative methods are well known in the art.

In a particular aspect, the nucleotide sequences encoding MGAT-X1 may be useful in assays that detect the presence of associated disorders, particularly those mentioned above. The nucleotide sequences encoding MGAT-X1 may be labeled by standard methods and added to a fluid or tissue sample from a patient under conditions suitable for the formation of hybridization complexes. After a suitable incubation period, the sample is washed and the signal is quantitated and compared with a standard value. If the amount of signal in the patient sample is significantly altered from that of a comparable control sample, the nucleotide sequences have hybridized with nucleotide sequences in the sample, and the presence of altered levels of nucleotide sequences encoding MGAT-X1 in the sample indicates the presence of the associated disorder. Such assays may also be used to evaluate the efficacy of a particular therapeutic treatment regimen in animal studies, in clinical trials, or in monitoring the treatment of an individual patient.

In order to provide a basis for the diagnosis dermatological diseases, urological diseases, muscle-skeleton disorders, hematological diseases, cancer, reproduction disorders, neurological diseases, metabolic diseases, cardiovascular diseases or gastroenterological diseases associated with expression of MGAT-X1, a normal or standard profile for expression is established. This may be accomplished by combining body fluids or cell extracts taken from normal subjects, either animal or human, with a sequence, or a fragment thereof, encoding MGAT-X1, under conditions suitable for hybridization or amplification. Standard hybridization may be quantified by comparing the values obtained from normal subjects with values from an experiment in which a known amount of a substantially purified polynucleotide is used. Standard values obtained from normal samples may be compared with values obtained from samples from patients who are symptomatic for a disorder. Deviation from standard values is used to establish the presence of a disorder.

Another technique for drug screening which may be used provides for high throughput screening of compounds having suitable binding affinity to the protein of interest as described in published PCT application WO84/03564. In this method, large numbers of different small test compounds are synthesized on a solid substrate, such as plastic pins or some other surface. The test compounds are reacted with MGAT-X1, or fragments thereof, and washed. Bound MGAT-X1 is then detected by methods well known in the art. Purified MGAT-X1 can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding MGAT-X1 specifically compete with a test compound for binding MGAT-X1. In this manner, antibodies can be used to detect the presence of any peptide which shares one or more antigenic determinants with MGAT-X1.

Transferase are ubiquitous in the mammalian host and are responsible for many biological functions, including many pathologies. Accordingly, it is desirable to find compounds and drugs which stimulate the activity of transferases on the one hand and which can inhibit the function of a transferase on the other hand. In particular, compounds which activate the transferases of the present invention are useful in treating various cardiovascular ailments such as caused by the lack of pulmonary blood flow or hypertension. In addition these compounds may also be used in treating various physiological disorders relating to abnormal control of fluid and electrolyte homeostasis and in diseases associated with abnormal angiotensin-induced aldosterone secretion.

Determination of a Therapeutically Effective Dose

The determination of a therapeutically effective dose is well within the capability of those skilled in the art. A therapeutically effective dose refers to that amount of active ingredient which increases or decreases MGAT-X1 activity relative to MGAT-X1 activity which occurs in the absence of the therapeutically effective dose. For any compound, the therapeutically effective dose can be estimated initially either in cell culture assays or in animal models, usually mice, rabbits, dogs, or pigs. The animal model also can be used to determine the appropriate concentration range and route of administration. Such information can then be used to determine useful doses and routes for administration in humans.

Therapeutic efficacy and toxicity, e.g., $ED_{50}$ (the dose therapeutically effective in 50% of the population) and $LD_{50}$ (the dose lethal to 50% of the population), can be determined by standard pharmaceutical procedures in cell cultures or experimental animals. The dose ratio of toxic to therapeutic effects is the therapeutic index, and it can be expressed as the ratio, $LD_{50}/ED_{50}$. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the $ED_{50}$ with little or no toxicity. The dosage varies within this range depending upon the dosage form employed, sensitivity of the patient, and the route of administration. The exact dosage will be determined by the practitioner, in light of factors related to the subject that requires treatment. Dosage and administration are adjusted to provide sufficient levels of the active ingredient or to maintain the desired effect. Factors which can be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions can be administered every 3 to 4 days, every week, or once every two weeks depending on the half-life and clearance rate of the particular formulation.

Normal dosage amounts can vary from 0.1 micrograms to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc. If the reagent is a single-chain antibody, polynucleotides encoding the antibody can be constructed and introduced into a cell either ex vivo or in vivo using well-established techniques including, but not limited to, transferrin-polycation-mediated DNA transfer, transfection with naked or encapsulated nucleic acids, liposome-mediated cellular fusion, intracellular transportation of DNA-coated latex beads, protoplast fusion, viral infection, electroporation, "gene gun," and DEAE- or calcium phosphate-mediated transfection.

If the expression product is mRNA, the reagent is preferably an antisense oligonucleotide or a ribozyme. Polynucleotides which express antisense oligonucleotides or ribozymes can be introduced into cells by a variety of methods, as described above. Preferably, a reagent reduces expression of MGAT-X1 gene or the activity of MGAT-X1 by at least about 10, preferably about 50, more preferably about 75, 90, or 100% relative to the absence of the reagent. The effectiveness of the mechanism chosen to decrease the level of expression of MGAT-X1 gene or the activity of MGAT-X1 can be assessed using methods well known in the art, such as hybridization of nucleotide probes to MGAT-X1-specific mRNA, quantitative RT-PCR, immunologic detection of MGAT-X1, or measurement of MGAT-X1 activity.

In any of the embodiments described above, any of the pharmaceutical compositions of the invention can be administered in combination with other appropriate therapeutic agents. Selection of the appropriate agents for use in combination therapy can be made by one of ordinary skill in the art, according to conventional pharmaceutical principles. The combination of therapeutic agents can act synergistically to effect the treatment or prevention of the various disorders described above. Using this approach, one may be able to achieve therapeutic efficacy with lower dosages of each agent, thus reducing the potential for adverse side effects. Any of the therapeutic methods described above can be applied to any subject in need of such therapy, including, for example, mammals such as dogs, cats, cows, horses, rabbits, monkeys, and most preferably, humans.

Nucleic acid molecules of the invention are those nucleic acid molecules which are contained in a group of nucleic acid molecules consisting of (i) nucleic acid molecules encoding a polypeptide comprising the amino acid sequence of SEQ ID NO:2, (ii) nucleic acid molecules comprising the sequence of SEQ ID NO:1, (iii) nucleic acid molecules having the sequence of SEQ ID NO:1, (iv) nucleic acid molecules the complementary strand of which hybridizes under stringent conditions to a nucleic acid molecule of (i), (ii), or (iii); and (v) nucleic acid molecules the sequence of which differs from the sequence of a nucleic acid molecule of (iii) due to the degeneracy of the genetic code, wherein the polypeptide encoded by said nucleic acid molecule has MGAT-X1 activity.

Polypeptides of the invention are those polypeptides which are contained in a group of polypeptides consisting of (i) polypeptides having the sequence of SEQ ID NO:2, polypeptides comprising the sequence of SEQ ID NO:2, polypeptides encoded by nucleic acid molecules of the invention and (iv) polypeptides which show at least 99%, 98%, 95%, 90%, or 80% homology with a polypeptide of (i), (ii), or wherein said purified polypeptide has MGAT-X1 activity.

It is an objective of the invention to provide a vector comprising the nucleic acid molecule of the invention.

Another object of the invention is a host cell containing a vector of the invention.

Another object of the invention is a method of producing a MGAT-X1 comprising the steps of (i) culturing a host cell of the invention under suitable conditions and (ii) recovering the MGAT-X1 from the culture medium.

Another object of the invention is a method for the detection of a polynucleotide encoding a MGAT-X1 in a sample comprising the steps of (i) hybridizing a polynucleotide of the invention to nucleic acid material of the sample, thereby forming a hybridization complex; and (ii) detecting said hybridization complex.

Another object of the invention is a method for the detection of a polynucleotide encoding a MGAT-X1 in a sample comprising the steps of (i) hybridizing a poly-nucleotide of the invention to nucleic acid material of the sample, thereby forming a hybridization complex; and (ii) detecting said hybridization complex, wherein, before hybridization, the nucleic acid material of the sample is amplified.

Another object of the invention is a method for the detection of a polynucleotide of the invention or a polypeptide of the invention comprising the steps of (i) contacting a sample with a reagent which specifically interacts with a polynucleotide of the invention or a polypeptide of the invention, and (ii) detecting said interaction.

Another object of the invention are diagnostic kits for conducting any of the methods above.

Regulators of a given protein, within the meaning of the invention, are understood as being compounds which alter either directly or indirectly the activity of the given protein either in vivo or in vitro. Alteration of the activity can be, e.g., but not limited to, by allosteric effects or by affecting the expression of the given protein.

Other objects of the invention are methods for screening for regulators of the activity of a MGAT-X1 comprising the steps of (i) contacting a test compound with a polypeptide of the invention, (ii) detect binding of said test compound to said polypeptide of the invention, wherein test compounds that bind under (ii) are identified as potential regulators of the MGAT-X1 activity.

Other objects of the invention are methods of the above, wherein the step of contacting is in or at the surface of a cell.

Other objects of the invention are methods of the above, wherein the step of contacting is in or at the surface of a cell wherein the cell is in vitro.

Other objects of the invention are methods of the above, wherein the step of contacting is in a cell-free system.

Other objects of the invention are methods of the above, wherein the polypeptide of the invention is coupled to a detectable label.

Other objects of the invention are methods of the above, wherein the compound is coupled to a detectable label.

Other objects of the invention are methods of the above, wherein the test compound displaces a ligand which is first bound to the polypeptide.

Other objects of the invention are methods of the above, wherein the polypeptide of the invention is attached to a solid support.

Other objects of the invention are methods of the above, wherein the compound is attached a solid support.

Another object of the invention is a method of screening for regulators of the activity of a MGAT-X1 comprising the steps of (i) measuring the activity of a polypeptide of the invention at a certain concentration of a test compound or in the absence of said test compound, (ii) measuring the activity of said polypeptide at a different concentrations of said test compound, wherein said test compound is identified as a regulator of the activity of a MGAT-X1 when there is a significant difference between the activities measured in (i) and (ii).

Another object of the invention is a method of screening for regulators of the activity of a MGAT-X1 comprising the steps of (i) measuring the activity of a polypeptide of the invention at a certain concentration of a test compound, (ii) measuring the activity of a polypeptide of the invention at the presence of a compound known to be a regulator of MGAT-X1.

Another object of the invention is a method of screening for regulators of the activity of a MGAT-X1 comprising the aforementioned methods, wherein the activities are measured in a cell.

Another object of the invention is a method of screening for regulators of the activity of a MGAT-X1 comprising the aforementioned methods, wherein the cell is in vitro.

Another object of the invention is a method of screening for regulators of the activity of a MGAT-X1 comprising the aforementioned methods, wherein the activities are measured in a cell-free system.

Another object of the invention is a method of screening for regulators of MGAT-X1 comprising the steps of (i) contacting a test compound with a nucleic acid molecule of the invention, (ii) detect binding of said test compound to said nucleic acid molecule, wherein said test compound is identified as a potential regulator of MGAT-X1 when it binds to said nucleic acid molecule.

Another object of the invention is a method of screening for regulators of MGAT-X1 comprising the steps of (i) contacting a test compound with a nucleic acid molecule of the invention, wherein the nucleic acid molecule is an RNA (ii) detect binding of said test compound to said RNA molecule, wherein said test compound is identified as a potential regulator of MGAT-X1 when it binds to said RNA molecule.

Another object of the invention is a method of screening for regulators of MGAT-X1-comprising the steps of contacting a test compound with a nucleic acid molecule of the invention, detect binding of said test compound to said nucleic acid molecule, wherein said test compound is identified as a potential regulator of MGAT-X1 when it binds to said nucleic acid molecule, wherein the contacting step is (i) in or at the surface of a cell or (ii) in a cell-free system or wherein (iii) the polypeptide or nucleic acid molecule is coupled to a detectable label or wherein (iv) the test compound is coupled to a detectable label.

Another object of the invention is a method of regulating the activity of a MGAT-X1 wherein MGAT-X1 is contacted with a regulator of MGAT-X1.

Another object of the invention is a method of diagnosing a MGAT-X1 related disease in a diseased mammal comprising the steps of (i) measuring the amount of a nucleic acid molecule of the invention in a sample taken from said diseased mammal, (ii) comparing the result of (i) to the amount of said nucleic acid molecule in one or several healthy mammals, wherein a MGAT-X1 related disease is diagnosed in the diseased mammal when the amount of said nucleic acid molecule in the diseased mammal is significantly different from the amount of said nucleic acid molecule in the healthy mammal/mammals Other objects of the invention are pharmaceutical compositions comprising (i) a nucleic acid molecule of the invention, (ii) a vector of the invention, or (iii) a polypeptide of the invention.

Another object of the invention are pharmaceutical compositions comprising a regulator of the invention.

Another object of the invention are pharmaceutical compositions comprising a regulator identified by methods of the invention for the treatment of dermatological diseases, urological diseases, muscle-skeleton disorders, hematological diseases, cancer, reproduction disorders, neurological diseases, metabolic diseases, cardiovascular diseases or gastroenterological diseases in a mammal.

Another object of the invention regards the use of regulators of a MGAT-X1 as identified by any of the aforementioned methods for the preparation of pharmaceutical compositions useful for the treatment of dermatological diseases, urological diseases, muscle-skeleton disorders, hematological diseases, cancer, reproduction disorders, neurological diseases, metabolic diseases, cardiovascular diseases or gastroenterological diseases in a mammal.

Another object of the invention are methods for the preparation of pharmaceutical compositions useful for the treatment of dermatological diseases, urological diseases, muscle-skeleton disorders, hematological diseases, cancer, reproduction disorders, neurological diseases, metabolic diseases, cardiovascular diseases or gastroenterological diseases in a mammal comprising the steps of (i) identifying a regulator of MGAT-X1 by any of the aforementioned methods, (ii) determining of whether said regulator ameliorates the symptoms of dermatological diseases, urological diseases, muscle-skeleton disorders, hematological diseases, cancer, reproduction disorders, neurological diseases, metabolic diseases, cardiovascular diseases or gastroenterological diseases in a mammal, (iii) combining of said regulator with an acceptable pharmaceutical carrier.

Another object of the invention is the use of a regulator of MGAT-X1 as identified by any of the aforementioned methods for (i) the treatment of dermatological diseases, urological diseases, muscle-skeleton disorders, hematological diseases, cancer, reproduction disorders, neurological diseases, metabolic diseases, cardiovascular diseases or gastroenterological diseases in a mammal, or (ii) use of a regulator of MGAT-X1 for the regulation of MGAT-X1 activity in a mammal having a dermatological disease, urological disease, muscle-skeleton disorder, hematological disease, cancer, reproduction disorder, neurological disease, metabolic disease, cardiovascular disease or gastroenterological disease.

Another object of the invention is the use of any of the aforementioned pharmaceutical compositions wherein the regulator of MGAT-X1 is either a small molecule, an RNA molecule, or an antisense oligonucleotide, or a polypeptide, an antibody, or a ribozyme. Small molecules, within the meaning of the invention, are organic molecules of a molecular weight of less than one thousand five hundred grams per mol.

The expression of human MGAT_X1 in cardiovascular and metabolical related tissues (as described above) suggests a particular—but not limited to—utilization MGAT_X1 for diagnosis and modulation of metabolic diseases and cardiovascular diseases. Furthermore the above described expression suggest a—but not limited to—utilization MGAT_X1 to dermatological diseases, urological diseases, muscle-skeleton disorders, hematological diseases, cancer, reproduction disorders, neurological diseases or gastroenterological diseases.

The examples below are provided to illustrate the subject invention. These examples are provided by way of illustration and are not included for the purpose of limiting the invention.

EXAMPLES

Example 1

Search for Homologous Sequences in Public Sequence Data Bases

The degree of homology can readily be calculated by known methods. Preferred methods to determine homology are designed to give the largest match between the sequences tested. Methods to determine homology are codified in publicly available computer programs such as BestFit, BLASTP, BLASTN, and FASTA. The BLAST programs are publicly available from NCBI and other sources in the internet.

For MGAT-X1 the following hits to known sequences were identified by using the BLAST algorithm [Altschul et al. (1997)] and the following set of parameters: matrix=BLOSUM62 and low complexity filter. The following databases were searched: NCBI (non-redundant database) and DERWENT patent database (Geneseq). The following hits were found:

>gb|AC128661.3| Mus musculus chromosome 7 clone RP24-567N23, complete sequence
Length = 421625747, Score = 1602 bits (833), Expect = 0.0, Identities = 833/833 (100%)
>gb|BC039181.1| Homo sapiens, Similar to diacylglycerol O-acyltransferase 2, clone IMAGE: 4746146, mRNA
Length = 1152, Score = 1594 bits (829), Expect = 0.0, Identities = 831/832 (99%)
>NA2002: AAD46546 Aad46546 Human diacylglycerol acyltransferase (DGAT) 2alpha homologue, DC3 cDNA. 1/2003
Length = 1240, Score = 1075 bits (559), Expect = 0.0, Identities = 559/559 (100%)
>ref|XM_228568.1| Rattus norvegicus similar to bA351K23.5 (novel protein) [Homo sapiens] (LOC302423), mRNA
Length = 966, Score = 990 bits (515), Expect = 0.0, Identities = 779/911 (85%)
>ref|XM_141972.1| Mus musculus similar to diacylglycerol O-acyltransferase homolog 2; GS1999 full [Homo sapiens] (LOC245533), mRNA
Length = 972, Score = 913 bits (475), Expect = 0.0, Identities = 695/805 (86%)
>emb|AL357752.19| Human DNA sequence from clone RP13-26D14 on chromosome Xq13.2-21.1, complete sequence
Length = 178868, Score = 498 bits (259), Expect = e−138, Identities = 259/259 (100%)
>NA2002: AAD46545 Aad46545 Mouse diacylglycerol acyltransferase (DGAT) 2alpha homologue, DC3 cDNA. 1/2003
Length = 435, Score = 448 bits (233), Expect = e−123, Identities = 364/430 (84%)
>NA2000: AAZ60386 Aaz60386 A diacylglycerol acyl transferase related expressed sequence tag. 5/2000
Length = 375, Score = 335 bits (174), Expect = 3e−89, Identities = 305/371 (82%)
>dbj|BD218492.1| Diacylglycerol acyl transferase proteins
Length = 375, Score = 335 bits (174), Expect = 3e−89, Identities = 305/371 (82%)
>emb|AL671299.18| Mouse DNA sequence from clone RP23-281K21 on chromosome X, complete sequence
Length = 214997, Score = 304 bits (158), Expect = 6e−80, Identities = 192/209 (91%)
>gb|AC091784.8| Genomic sequence for Mus musculus, clone RP23-213D23, complete sequence
Length = 215410, Score = 304 bits (158), Expect = 6e−80, Identities = 192/209 (91%)
>ref|XM_228583.1| Rattus norvegicus similar to bA351K23.5 (novel protein) [Homo sapiens] (LOC302425), mRNA
Length = 903, Score = 123 bits (64), Expect = 2e−25, Identities = 122/151 (80%)
>NA2002: AAD46547 Aad46547 Human diacylglycerol acyltransferase (DGAT)2alpha homologue, DC4 cDNA. 1/2003
Length = 1872, Score = 116 bits (60), Expect = 3e−23, Identities = 114/141 (80%)
>NA2001A: ABA18912 Aba18912 Human nervous system related polynucleotide SEQ ID NO 11243. 1/2O02
Length = 3527, Score = 116 bits (60), Expect = 3e−23, Identities = 114/141 (80%)

Example 2

Expression Profiling

Total cellular RNA was isolated from cells by one of two standard methods: 1) guanidine isothiocyanate/Cesium chloride density gradient centrifugation [Kellogg et al. (1990)]; or with the Tri-Reagent protocol according to the manufacturer's specifications (Molecular Research Center, Inc., Cincinatti, Ohio). Total RNA prepared by the Tri-reagent protocol was treated with DNAse I to remove genomic DNA contamination.

For relative quantitation of the mRNA distribution of the human MGAT-X1, total RNA from each cell or tissue source was first reverse transcribed. 85 µg of total RNA was reverse transcribed using 1 µmole random hexamer primers, 0.5 mM each of dATP, dCTP, dGTP and dTTP (Qiagen, Hilden, Germany), 3000 U RnaseQut (Invitrogen, Groningen, Netherlands) in a final volume of 680 µl. The first strand synthesis buffer and Omniscript reverse transcriptase (2 u/µl) were from (Qiagen, Hilden, Germany). The reaction was incubated at 37° C. for 90 minutes and cooled on ice. The volume was adjusted to 6800 µl with water, yielding a final concentration of 12.5 ng/µl of starting RNA.

For relative quantitation of the distribution of the human MGAT-X1 mRNA in cells and tissues the Applied Biosystems 7900HT Sequence Detection system was used according to the manufacturer's specifications and protocols. PCR reactions were set up to quantitate the human MGAT-X1 and the housekeeping genes HPRT (hypoxanthine phosphoribosyltransferase), GAPDH (glyceraldehyde-3-phosphate dehydrogenase), β-actin, and others. Forward and reverse primers and probes for the human MGAT-X1 were designed using the Perkin Elmer ABI Primer Express™ software and were synthesized by TibMolBiol (Berlin, Germany). The human MGAT-X1 forward primer sequence was: Primer1 (SEQ ID NO: 3). The human MGAT-X1 reverse primer sequence was Primer2 (SEQ ID NO: 5). Probe1 (SEQ ID NO: 4), labelled with FAM (carboxyfluorescein succinimidyl ester) as the reporter dye and TAMRA (carboxytetramethylrhodamine) as the quencher, is used as a probe for the human UST3 like protein 1. The following reagents were prepared in a total of 25 µl: 1× TaqMan buffer A, 5.5 mM $MgCl_2$, 200 nM of dATP, dCTP, dGTP, and dUTP, 0.025 U/µl AmpliTaq Gold™, 0.01 U/µl AmpErase and Probe1 (SEQ ID NO: 4), human MGAT-X1 forward and reverse primers each at 200 nM, 200 nM, human MGAT-X1FAM/TAMRA-labelled probe, and 5 µl of template cDNA. Thermal cycling parameters were 2 min at 50° C., followed by 10 min at 95° C., followed by 40 cycles of melting at 95° C. for 15 sec and annealing/extending at 60° C. for 1 min.

Calculation of Corrected CT Values

The CT (threshold cycle) value is calculated as described in the "Quantitative determination of nucleic acids" section. The CF-value (factor for threshold cycle correction) is calculated as follows:

1. PCR reactions were set up to quantitate the housekeeping genes (HKG) for each cDNA sample.

2. $CT_{HKG}$-values (threshold cycle for housekeeping gene) were calculated as described in the "Quantitative determination of nucleic acids" section.
3. $CT_{HKG}$-mean values (CT mean value of all HKG tested on one cDNAs) of all HKG for each cDNA are calculated (n=number of HKG):

$$CT_{HKG\text{-}n}\text{-mean value}=(CT_{HKG1}\text{-value}+CT_{HKG2}\text{-value}+\ldots+CT_{HKG\text{-}n}\text{-value})/n$$

4. $CT_{pannel}$ mean value (CT mean value of all HKG in all tested cDNAs)=$(CT_{HKG1}$-mean value+$CT_{HKG2}$-mean value+ . . . +$CT_{HKG\text{-}y}$-mean value)/y (y=number of cDNAs)
5. $CF_{cDNA\text{-}n}$ (correction factor for cDNA n)=$CT_{pannel}$-mean value−$CT_{HKG\text{-}n}$-mean value
6. $CT_{cDNA\text{-}n}$ (CT value of the tested gene for the cDNA n)+$CF_{cDNA\text{-}n}$ (correction factor for cDNA n)= $CT_{cor\text{-}cDNA\text{-}n}$(corrected CT value for a gene on cDNA n)

Calculation of Relative Expression

Definition: highest $CT_{cor\text{-}cDNA\text{-}n}\neq 40$ is defined as $CT_{cor\text{-}cDNA}$ [high]

Relative Expression=$2^{(CTcor\text{-}cDNA[high]-CTcor\text{-}cDNA\text{-}n)}$

Expression Profile

The results of the mRNA-quantification (expression profiling) is shown in Table 1.

TABLE 1

Relative expression of MGAT-X1 in various human tissues.

| Tissue | Relative Expression |
|---|---|
| fetal heart | 1 |
| heart | 1 |
| heart | 484 |
| pericardium | 101 |
| heart atrium (right) | 17 |
| heart atrium (right) | 1 |
| heart atrium (left) | 24 |
| heart atrium (left) | 1 |
| heart ventricle (left) | 1 |
| heart ventricle (right) | 1 |
| heart apex | 17 |
| Purkinje fibers | 20 |
| interventricular septum | 20 |
| fetal aorta | 96 |
| aorta | 30 |
| aorta | 3 |
| aorta | 1 |
| aorta valve | 106 |
| artery | 96 |
| coronary artery | 3 |
| coronary artery | 32 |
| coronary artery | 1 |
| pulmonary artery | 40 |
| carotid artery | 11 |
| mesenteric artery | 24 |
| arteria radialis | 1 |
| vein | 149 |
| pulmonic valve | 1585 |
| vein (saphena magna) | 56 |
| (caval) vein | 11 |
| coronary artery endothel cells | 137 |
| coronary artery smooth muscle | 3 |
| aortic smooth muscle cells | 2 |
| pulmonary artery smooth | 7 |
| aortic endothel cells | 28 |
| HUVEC cells | 5 |
| pulmonary artery endothel cells | 2 |
| iliac artery endothel cells | 12 |
| skin | 1771 |
| adrenal gland | 9 |
| thyroid | 30 |
| thyroid tumor | 27 |
| pancreas | 1 |
| pancreas liver cirrhosis | 9 |

TABLE 1-continued

Relative expression of MGAT-X1 in various human tissues.

| Tissue | Relative Expression |
|---|---|
| esophagus | 7 |
| esophagus tumor | 4 |
| stomach | 21 |
| stomach tumor | 17 |
| colon | 20 |
| colon tumor | 101 |
| small intestine | 21 |
| ileum | 198 |
| ileum tumor | 24 |
| ileum chronic inflammation | 80 |
| rectum | 247 |
| rectum tumor | 1 |
| fetal liver | 19 |
| liver | 19 |
| liver | 1 |
| liver liver cirrhosis | 63 |
| liver lupus disease | 1 |
| liver tumor | 676 |
| HEP G2 cells | 67 |
| leukocytes (peripheral blood) | 6 |
| Jurkat (T-cells) | 53 |
| Raji (B-cells) | 1 |
| bone marrow | 2 |
| erythrocytes | 1209 |
| lymphnode | 16 |
| thymus | 28 |
| thrombocytes | 446 |
| bone marrow stromal cells | 29 |
| bone marrow CD71+ cells | 1136 |
| bone marrow CD33+ cells | 765 |
| bone marrow CD34+ cells | 600 |
| bone marrow CD15+ cells | 534 |
| cord blood CD71+ cells | 671 |
| cord blood CD34+ cells | 471 |
| neutrophils cord blood | 405 |
| T-cells peripheral blood CD4+ | 867 |
| T-cells peripheral blood CD8+ | 6081 |
| monocytes peripheral blood | 1121 |
| B-cells peripheral blood | 8422 |
| neutrophils peripheral blood | 138 |
| spleen | 25 |
| spleen liver cirrhosis | 6 |
| skeletal muscle | 19 |
| cartilage | 333 |
| bone connective tissue | 133 |
| adipose | 4153 |
| brain | 37 |
| cerebellum | 8 |
| cerebral cortex | 124 |
| frontal lobe | 103 |
| occipital lobe | 74 |
| parietal lobe | 33 |
| temporal lobe | 55 |
| substantia nigra | 111 |
| caudatum | 221 |
| corpus callosum | 138 |
| nucleus accumbens | 128 |
| putamen | 49 |
| hippocampus | 111 |
| thalamus | 11 |
| posteroventral thalamus | 388 |
| dorsalmedial thalamus | 471 |
| hypothalamus | 234 |
| dorsal root ganglia | 36 |
| spinal cord | 38 |
| spinal cord (ventral horn) | 491 |
| spinal cord (dorsal horn) | 568 |
| glial tumor H4 cells | 20 |
| neural progenitor cells | 304 |
| astrocytes | 63 |
| retina | 534 |
| fetal lung | 32 |
| fetal lung fibroblast IMR-90 | 4 |
| fetal lung fibroblast MRC-5 | 3 |
| lung | 3 |
| lung | 6 |

TABLE 1-continued

Relative expression of MGAT-X1 in various human tissues.

| Tissue | Relative Expression |
|---|---|
| lung | 1 |
| lung right upper lobe | 32 |
| lung right mid lobe | 16 |
| lung right lower lobe | 24 |
| lung lupus disease | 41 |
| lung tumor | 97 |
| lung COPD | 36 |
| trachea | 16 |
| primary bronchia | 1 |
| secondary bronchia | 191 |
| bronchial epithelial cells | 37 |
| bronchial smooth muscle cells | 14 |
| small airway epithelial cells | 49 |
| cervix | 28 |
| testis | 76 |
| HeLa cells (cervix tumor) | 1 |
| placenta | 18 |
| uterus | 119 |
| uterus tumor | 14 |
| ovary | 27 |
| ovary tumor | 57 |
| breast | 31 |
| breast tumor | 377 |
| mammary gland | 17 |
| prostata | 6 |
| prostata | 27 |
| prostata | 19 |
| prostate BPH | 73 |
| prostate tumor | 362 |
| bladder | 15 |
| bladder | 1 |
| bladder | 8 |
| ureter | 31 |
| penis | 343 |
| corpus cavernosum | 1235 |
| fetal kidney | 288 |
| kidney | 16 |
| kidney | 1 |
| kidney | 4 |
| kidney tumor | 23 |
| renal epithelial cells | 140 |
| HEK 293 cells | 142 |

Example 3

Antisense Analysis

Knowledge of the correct, complete cDNA sequence coding for MGAT-X1 enables its use as a tool for antisense technology in the investigation of gene function. Oligonucleotides, cDNA or genomic fragments comprising the antisense strand of a polynucleotide coding for MGAT-X1 are used either in vitro or in vivo to inhibit translation of the mRNA. Such technology is now well known in the art, and antisense molecules can be designed at various locations along the nucleotide sequences. By treatment of cells or whole test animals with such antisense sequences, the gene of interest is effectively turned off. Frequently, the function of the gene is ascertained by observing behavior at the intracellular, cellular, tissue or organismal level (e.g., lethality, loss of differentiated function, changes in morphology, etc.).

In addition to using sequences constructed to interrupt transcription of a particular open reading frame, modifications of gene expression is obtained by designing antisense sequences to intron regions, promoter/enhancer elements, or even to trans-acting regulatory genes.

Example 4

Expression of MGAT-X1

Expression of MGAT-X1 is accomplished by subcloning the cDNAs into appropriate expression vectors and transfecting the vectors into expression hosts such as, e.g., E. coli. In a particular case, the vector is engineered such that it contains a promoter for β-galactosidase, upstream of the cloning site, followed by sequence containing the amino-terminal Methionine and the subsequent seven residues of β-galactosidase. Immediately following these eight residues is an engineered bacteriophage promoter useful for artificial priming and transcription and for providing a number of unique endonuclease restriction sites for cloning.

Induction of the isolated, transfected bacterial strain with Isopropyl-β-D-thiogalactopyranoside (IPTG) using standard methods produces a fusion protein corresponding to the first seven residues of β-galactosidase, about 15 residues of "linker", and the peptide encoded within the cDNA. Since cDNA clone inserts are generated by an essentially random process, there is probability of 33% that the included cDNA will lie in the correct reading frame for proper translation. If the cDNA is not in the proper reading frame, it is obtained by deletion or insertion of the appropriate number of bases using well known methods including in vitro mutagenesis, digestion with exonuclease III or mung bean nuclease, or the inclusion of an oligonucleotide linker of appropriate length.

The MGAT-X1 cDNA is shuttled into other vectors known to be useful for expression of proteins in specific hosts. Oligonucleotide primers containing cloning sites as well as a segment of DNA (about 25 bases) sufficient to hybridize to stretches at both ends of the target cDNA is synthesized chemically by standard methods. These primers are then used to amplify the desired gene segment by PCR. The resulting gene segment is digested with appropriate restriction enzymes under standard conditions and isolated by gel electrophoresis. Alternately, similar gene segments are produced by digestion of the cDNA with appropriate restriction enzymes. Using appropriate primers, segments of coding sequence from more than one gene are ligated together and cloned in appropriate vectors. It is possible to optimize expression by construction of such chimeric sequences.

Suitable expression hosts for such chimeric molecules include, but are not limited to, mammalian cells such as Chinese Hamster Ovary (CHO) and human 293 cells, insect cells such as Sf9 cells, yeast cells such as Saccharomyces cerevisiae and bacterial cells such as E. coli. For each of these cell systems, a useful expression vector also includes an origin of replication to allow propagation in bacteria, and a selectable marker such as the β-lactamase antibiotic resistance gene to allow plasmid selection in bacteria. In addition, the vector may include a second selectable marker such as the neomycin phosphotransferase gene to allow selection in transfected eukaryotic host cells. Vectors for use in eukaryotic expression hosts require RNA processing elements such as 3' polyadenylation sequences if such are not part of the cDNA of interest.

Additionally, the vector contains promoters or enhancers which increase gene expression. Such promoters are host specific and include MMTV, SV40, and metallothionine promoters for CHO cells; trp, lac, tac and T7 promoters for bacterial hosts; and alpha factor, alcohol oxidase and PGH promoters for yeast. Transcription enhancers, such as the rous sarcoma virus enhancer, are used in mammalian host cells. Once homogeneous cultures of recombinant cells are obtained through standard culture methods, large quantities of recombinantly produced MGAT-X1 are recovered from the conditioned medium and analyzed using chromatographic methods known in the art. For example, MGAT-X1 can be cloned into the expression vector pcDNA3, as exemplified herein. This product can be used to transform, for example, HEK293 or COS by methodology standard in the art. Specifically, for example, using Lipofectamine (Gibco BRL catalog no. 18324-020) mediated gene transfer.

Example 5

Isolation of Recombinant MGAT-X1

MGAT-X1 is expressed as a chimeric protein with one or more additional polypeptide domains added to facilitate protein purification. Such purification facilitating domains include, but are not limited to, metal chelating peptides such as histidine-tryptophan modules that allow purification on immobilized metals [Appa Rao (1997)] and the domain utilized in the FLAGS extension/affinity purification system (Immunex Corp., Seattle, Wash.). The inclusion of a cleavable linker sequence such as Factor Xa or enterokinase (Invitrogen, Groningen, The Netherlands) between the purification domain and the MGAT-X1 sequence is useful to facilitate expression of MGAT-X1.

Example 6

Production of MGAT-X1 Specific Antibodies

Two approaches are utilized to raise antibodies to MGAT-X1, and each approach is useful for generating either polyclonal or monoclonal antibodies. In one approach, denatured protein from reverse phase HPLC separation is obtained in quantities up to 75 mg. This denatured protein is used to immunize mice or rabbits using standard protocols; about 100 μg are adequate for immunization of a mouse, while up to 1 mg might be used to immunize a rabbit. For identifying mouse hybridomas, the denatured protein is radioiodinated and used to screen potential murine B-cell hybridomas for those which produce antibody. This procedure requires only small quantities of protein, such that 20 mg is sufficient for labeling and screening of several thousand clones.

In the second approach, the amino acid sequence of an appropriate MGAT-X1 domain, as deduced from translation of the cDNA, is analyzed to determine regions of high antigenicity. Oligopeptides comprising appropriate hydrophilic regions are synthesized and used in suitable immunization protocols to raise antibodies. The optimal amino acid sequences for immunization are usually at the C-terminus, the N-terminus and those intervening, hydrophilic regions of the polypeptide which are likely to be exposed to the external environment when the protein is in its natural conformation.

Typically, selected peptides, about 15 residues in length, are synthesized using an Applied Biosystems Peptide Synthesizer Model 431A using fmoc-chemistry and coupled to keyhole limpet hemocyanin (KLH; Sigma, St. Louis, Mo.) by reaction with M-maleimidobenzoyl-N-hydroxysuccinimide ester, MBS. If necessary, a cysteine is introduced at the N-terminus of the peptide to permit coupling to KLH. Rabbits are immunized with the peptide-KLH complex in complete Freund's adjuvant. The resulting antisera are tested for antipeptide activity by binding the peptide to plastic, blocking with 1% bovine serum albumin, reacting with antisera, washing and reacting with labeled (radioactive or fluorescent), affinity purified, specific goat anti-rabbit IgG.

Hybridomas are prepared and screened using standard techniques. Hybridomas of interest are detected by screening with labeled MGAT-X1 to identify those fusions producing the monoclonal antibody with the desired specificity. In a typical protocol, wells of plates (FAST; Becton-Dickinson, Palo Alto, Calif.) are coated during incubation with affinity purified, specific rabbit anti-mouse (or suitable antispecies 1 g) antibodies at 10 mg/ml. The coated wells are blocked with 1% bovine serum albumin, (BSA), washed and incubated with supernatants from hybridomas. After washing the wells are incubated with labeled MGAT-X1 at 1 mg/ml. Supernatants with specific antibodies bind more labeled MGAT-X1 than is detectable in the background. Then clones producing specific antibodies are expanded and subjected to two cycles of cloning at limiting dilution. Cloned hybridomas are injected into pristane-treated mice to produce ascites, and monoclonal antibody is purified from mouse ascitic fluid by affinity chromatography on Protein A. Monoclonal antibodies with affinities of at least $10^8$ $M^{-1}$, preferably $10^9$ to $10^{10}$ $M^{-1}$ or stronger, are typically made by standard procedures.

Example 7

Diagnostic Test Using MGAT-X1 Specific Antibodies

Particular MGAT-X1 antibodies are useful for investigating signal transduction and the diagnosis of infectious or hereditary conditions which are characterized by differences in the amount or distribution of MGAT-X1 or downstream products of an active signaling cascade.

Diagnostic tests for MGAT-X1 include methods utilizing antibody and a label to detect MGAT-X1 in human body fluids, membranes, cells, tissues or extracts of such. The polypeptides and antibodies of the present invention are used with or without modification. Frequently, the polypeptides and antibodies are labeled by joining them, either covalently or noncovalently, with a substance which provides for a detectable signal. A wide variety of labels and conjugation techniques are known and have been reported extensively in both the scientific and patent literature. Suitable labels include radionuclides, enzymes, substrates, cofactors, inhibitors, fluorescent agents, chemiluminescent agents, chromogenic agents, magnetic particles and the like.

A variety of protocols for measuring soluble or membrane-bound MGAT-X1, using either polyclonal or monoclonal antibodies specific for the protein, are known in the art. Examples include enzyme-linked immunosorbent assay (ELISA), radioimmunoassay (RIA) and fluorescent activated cell sorting (FACS). A two-site monoclonal-based immunoassay utilizing monoclonal antibodies reactive to two non-interfering epitopes on MGAT-X1 is preferred, but a competitive binding assay may be employed.

Example 8

Purification of Native MGAT-X1 Using Specific Antibodies

Native or recombinant MGAT-X1 is purified by immunoaffinity chromatography using antibodies specific for MGAT-X1. In general, an immunoaffinity column is constructed by covalently coupling the anti-TRH antibody to an activated chromatographic resin.

Polyclonal immunoglobulins are prepared from immune sera either by precipitation with ammonium sulfate or by purification on immobilized Protein A (Pharmacia LKB Biotechnology, Piscataway N.J.). Likewise, monoclonal antibodies are prepared from mouse ascites fluid by ammonium sulfate precipitation or chromatography on immobilized Protein A. Partially purified immunoglobulin is covalently attached to a chromatographic resin such as CnBr-activated Sepharose (Pharmacia LKB Biotechnology). The antibody is coupled to the resin, the resin is blocked, and the derivative resin is washed according to the manufacturer's instructions.

Such immunoaffinity columns are utilized in the purification of MGAT-X1 by preparing a fraction from cells containing MGAT-X1 in a soluble form. This preparation is derived by solubilization of whole cells or of a subcellular fraction obtained via differential centrifugation (with or without addition of detergent) or by other methods well known in the art. Alternatively, soluble MGAT-X1 containing a signal sequence is secreted in useful quantity into the medium in which the cells are grown.

A soluble MGAT-X1-containing preparation is passed over the immunoaffinity column, and the column is washed under conditions that allow the preferential absorbance of MGAT-X1 (e.g., high ionic strength buffers in the presence of detergent). Then, the column is eluted under conditions that disrupt antibody/protein binding (e.g., a buffer of pH 2-3 or a high concentration of a chaotrope such as urea or thiocyanate ion), and MGAT-X1 is collected.

Example 9

Drug Screening

Test compounds can be screened for the ability to bind to diacylglycerol acyltransferase polypeptides or polynucleotides or to affect diacylglycerol acyltransferase activity or diacylglycerol acyltransferase gene expression using high throughput screening. Using high throughput screening, many discrete compounds can be tested in parallel so that large numbers of test compounds can be quickly screened. The most widely established techniques utilize 96-well microtiter plates. The wells of the microtiter plates typically require assay volumes that range from 50 to 500 microliter. In addition to the plates, many instruments, materials, pipettors, robotics, plate washers, and plate readers are commercially available to fit the 96-well format.

Alternatively, "free format assays," or assays that have no physical barrier between samples, can be used. For example, an assay using pigment cells (melanocytes) in a simple homogeneous assay for combinatorial peptide libraries is described by Jayawickreme et al., *Proc. Natl. Acad. Sci. U.S.A.* 19, 1614-18 (1994). The cells are placed under agarose in petri dishes, then beads that carry combinatorial compounds are placed on the surface of the agarose. The combinatorial compounds are partially released the compounds from the beads. Active compounds can be visualized as dark pigment areas because, as the compounds diffuse locally into the gel matrix, the active compounds cause the cells to change colors.

Another example of a free format assay is described by Chelsky, "Strategies for Screening Combinatorial Libraries: Novel and Traditional Approaches," reported at the First Annual Conference of The Society for Biomolecular Screening in Philadelphia, Pa. (Nov. 7-10, 1995). Chelsky placed a simple homogenous enzyme assay for carbonic anhydrase inside an agarose gel such that the enzyme in the gel would cause a color change throughout the gel. Thereafter, beads carrying combinatorial compounds via a photolinker were placed inside the gel and the compounds were partially released by UV-light. Compounds that inhibited the enzyme were observed as local zones of inhibition having less color change.

Yet another example is described by Salmon et al., *Molecular Diversity* 2, 57-63 (1996). In this example, combinatorial libraries were screened for compounds that had cytotoxic effects on cancer cells growing in agar.

Another high throughput screening method is described in Beutel et al., U.S. Pat. No. 5,976,813. In this method, test samples are placed in a porous matrix. One or more assay components are then placed within, on top of, or at the bottom of a matrix such as a gel, a plastic sheet, a filter, or other form of easily manipulated solid support. When samples are introduced to the porous matrix they diffuse sufficiently slowly, such that the assays can be performed without the test samples running together.

Example 10

Rational Drug Design

The goal of rational drug design is to produce structural analogs of biologically active polypeptides of interest or of small molecules with which they interact, agonists, antagonists, or inhibitors. Any of these examples are used to fashion drugs which are more active or stable forms of the polypeptide or which enhance or interfere with the function of a polypeptide in vivo.

In one approach, the three-dimensional structure of a protein of interest, or of a protein-inhibitor complex, is determined by x-ray crystallography, by computer modeling or, most typically, by a combination of the two approaches. Both the shape and charges of the polypeptide must be ascertained to elucidate the structure and to determine active site(s) of the molecule. Less often, useful information regarding the structure of a polypeptide is gained by modeling based on the structure of homologous proteins. In both cases, relevant structural information is used to design efficient inhibitors. Useful examples of rational drug design include molecules which have improved activity or stability or which act as inhibitors, agonists, or antagonists of native peptides.

It is also possible to isolate a target-specific antibody, selected by functional assay, as described above, and then to solve its crystal structure. This approach, in principle, yields a pharmacore upon which subsequent drug design is based. It is possible to bypass protein crystallography altogether by generating anti-idiotypic antibodies (anti-ids) to a functional, pharmacologically active antibody. As a mirror image of a mirror image, the binding site of the anti-ids is expected to be an analog of the original transferase. The anti-id is then used to identify and isolate peptides from banks of chemically or biologically produced peptides. The isolated peptides then act as the pharmacore.

By virtue of the present invention, sufficient amount of polypeptide are made available to perform such analytical studies as X-ray crystallography. In addition, knowledge of the MGAT-X1 amino acid sequence provided herein provides guidance to those employing computer modeling techniques in place of or in addition to x-ray crystallography.

Example 11

Use and Administration of Antibodies, Inhibitors, or Antagonists

Antibodies, inhibitors, or antagonists of MGAT-X1 or other treatments and compounds that are limiters of signal transduction (LSTs), provide different effects when administered therapeutically. LSTs are formulated in a nontoxic, inert, pharmaceutically acceptable aqueous carrier medium preferably at a pH of about 5 to 8, more preferably 6 to 8, although pH may vary according to the characteristics of the antibody, inhibitor, or antagonist being formulated and the condition to be treated. Characteristics of LSTs include solubility of the molecule, its half-life and antigenicity/immunogenicity. These and other characteristics aid in defining an effective carrier. Native human proteins are preferred as LSTs, but organic or synthetic molecules resulting from drug screens are equally effective in particular situations.

LSTs are delivered by known routes of administration including but not limited to topical creams and gels; transmucosal spray and aerosol; transdermal patch and bandage; injectable, intravenous and lavage formulations; and orally administered liquids and pills particularly formulated to resist stomach acid and enzymes. The particular formulation, exact dosage, and route of administration is determined by the attending physician and varies according to each specific situation.

Such determinations are made by considering multiple variables such as the condition to be treated, the LST to be administered, and the pharmacokinetic profile of a particular LST. Additional factors which are taken into account include severity of the disease state, patient's age, weight, gender and diet, time and frequency of LST administration, possible combination with other drugs, reaction sensitivities, and tolerance/response to therapy. Long acting LST formulations might be administered every 3 to 4 days, every week, or once every two weeks depending on half-life and clearance rate of the particular LST.

Normal dosage amounts vary from 0.1 to $10^5$ μg, up to a total dose of about 1 g, depending upon the route of administration. Guidance as to particular dosages and methods of delivery is provided in the literature; see U.S. Pat. Nos. 4,657,760; 5,206,344; or 5,225,212. Those skilled in the art employ different formulations for different LSTs. Administration to cells such as nerve cells necessitates delivery in a manner different from that to other cells such as vascular endothelial cells.

It is contemplated that abnormal signal transduction, trauma, or diseases which trigger MGAT-X1 activity are treatable with LSTs. These conditions or diseases are specifically diagnosed by the tests discussed above, and such testing should be performed in suspected cases of viral, bacterial or fungal infections, allergic responses, mechanical injury associated with trauma, hereditary diseases, lymphoma or carcinoma, or other conditions which activate the genes of lymphoid or neuronal tissues.

Example 12

Production of Non-Human Transgenic Animals

Animal model systems which elucidate the physiological and behavioral roles of the MGAT-X1 transferase are produced by creating nonhuman transgenic animals in which the activity of the MGAT-X1 transferase is either increased or decreased, or the amino acid sequence of the expressed MGAT-X1 transferase is altered, by a variety of techniques. Examples of these techniques include, but are not limited to: 1) Insertion of normal or mutant versions of DNA encoding a MGAT-X1 transferase, by microinjection, electroporation, retroviral transfection or other means well known to those skilled in the art, into appropriately fertilized embryos in order to produce a transgenic animal or 2) homologous recombination of mutant or normal, human or animal versions of these genes with the native gene locus in transgenic animals to alter the regulation of expression or the structure of these MGAT-X1 transferase sequences. The technique of homologous recombination is well known in the art. It replaces the native gene with the inserted gene and hence is useful for producing an animal that cannot express native MGAT-X1 transferases but does express, for example, an inserted mutant MGAT-X1 transferase, which has replaced the native MGAT-X1 transferase in the animal's genome by recombination, resulting in underexpression of the transferase. Microinjection adds genes to the genome, but does not remove them, and the technique is useful for producing an animal which expresses its own and added MGAT-X1 transferase, resulting in overexpression of the MGAT-X1 transferase.

One means available for producing a transgenic animal, with a mouse as an example, is as follows: Female mice are mated, and the resulting fertilized eggs are dissected out of their oviducts. The eggs are stored in an appropriate medium such as cesiumchloride M2 medium. DNA or cDNA encoding MGAT-X1 is purified from a vector by methods well known to the one skilled in the art. Inducible promoters may be fused with the coding region of the DNA to provide an experimental means to regulate expression of the transgene. Alternatively or in addition, tissue specific regulatory elements may be fused with the coding region to permit tissue-specific expression of the transgene. The DNA, in an appropriately buffered solution, is put into a microinjection needle (which may be made from capillary tubing using a piper puller) and the egg to be injected is put in a depression slide. The needle is inserted into the pronucleus of the egg, and the DNA solution is injected. The injected egg is then transferred into the oviduct of a pseudopregnant mouse which is a mouse stimulated by the appropriate hormones in order to maintain false pregnancy, where it proceeds to the uterus, implants, and develops to term. As noted above, microinjection is not the only method for inserting DNA into the egg but is used here only for exemplary purposes.

Example 13

Binding Assay

For binding assays, the test compound is preferably a small molecule which binds to a acylglycerol acyltransferase polypeptide, thereby reducing the normal biological activity of the acylglycerol acyltransferase polypeptide. Examples of such small molecules include, but are not limited to, small peptides or peptide-like molecules. In binding assays, either the test compound or the acylglycerol acyltransferase polypeptide can comprise a detectable label, such as a fluorescent, radioisotopic, chemiluminescent, or enzymatic label, such as horseradish peroxidase, alkaline phosphatase, or luciferase. Detection of a test compound which is bound to the acylglycerol acyltransferase polypeptide can then be accomplished, for example, by direct counting of radioemmission, by scintillation counting, or by determining conversion of an appropriate substrate to a detectable product.

Alternatively, binding of a test compound to a acylglycerol acyltransferase polypeptide can be determined without labeling either of the interactants. For example, a microphysiometer can be used to detect binding of a test compound with a acylglycerol acyltransferase polypeptide. A microphysiometer (e.g., Cytosensor™) is an analytical instrument that measures the rate at which a cell acidifies its environment using a light-addressable potentiometric sensor (LAPS). Changes in this acidification rate can be used as an indicator of the interaction between a test compound and a acylglycerol acyltransferase polypeptide (McConnell et al., *Science* 257, 1906-1912, 1992).

Determining the ability of a test compound to bind to a acylglycerol acyltransferase polypeptide also can be accomplished using a technology such as real-time Bimolecular Interaction Analysis (BIA) (Sjolander & Urbaniczky, *Anal. Chem.* 63, 2338-2345, 1991, and Szabo et al., *Curr. Opin. Struct. Biol.* 5, 699-705, 1995). BIA is a technology for studying biospecific interactions in real time, without labeling any of the interactants (e.g., BIAcore™). Changes in the optical phenomenon surface plasmon resonance (SPR) can be used as an indication of real-time reactions between biological molecules.

In yet another aspect of the invention, a acylglycerol acyltransferase polypeptide can be used as a "bait protein" in a two-hybrid assay or three-hybrid assay (see, e.g., U.S. Pat. No. 5,283,317; Zervos et al., *Cell* 72, 223-232, 1993; Madura et al., *J. Biol. Chem.* 268, 12046-12054, 1993; Bartel et al., *Biotechniques* 14, 920-924, 1993; Iwabuchi et al., *Oncogene* 8, 1693-1696, 1993; and Brent WO94/10300), to identify other proteins which bind to or interact with the acylglycerol acyltransferase polypeptide and modulate its activity.

The two-hybrid system is based on the modular nature of most transcription factors, which consist of separable DNA-binding and activation domains. Briefly, the assay utilizes two different DNA constructs. For example, in one construct, polynucleotide encoding a acylglycerol acyltransferase polypeptide can be fused to a polynucleotide encoding the DNA binding domain of a known transcription factor (e.g., GAL-4). In the other construct a DNA sequence that encodes an unidentified protein ("prey" or "sample") can be fused to a polynucleotide that codes for the activation domain of the known transcription factor. If the "bait" and the "prey" proteins are able to interact in vivo to form an protein-dependent complex, the DNA-binding and activation domains of the transcription factor are brought into close proximity. This proximity allows transcription of a reporter gene (e.g., LacZ), which is operably linked to a transcriptional regulatory site responsive to the transcription factor. Expression of the reporter gene can be detected, and cell colonies containing the functional transcription factor can be isolated and used to obtain the DNA sequence encoding the protein which interacts with the acylglycerol acyltransferase polypeptide.

It may be desirable to immobilize either the acylglycerol acyltransferase polypeptide (or polynucleotide) or the test compound to facilitate separation of bound from unbound forms of one or both of the interactants, as well as to accommodate automation of the assay. Thus, either the acylglycerol acyltransferase polypeptide (or polynucleotide) or the test compound can be bound to a solid support. Suitable solid supports include, but are not limited to, glass or plastic slides, tissue culture plates, microtiter wells, tubes, silicon chips, or particles such as beads (including, but not limited to, latex, polystyrene, or glass beads). Any method known in the art can be used to attach the acylglycerol acyltransferase polypeptide (or polynucleotide) or test compound to a solid support, including use of covalent and non-covalent linkages, passive absorption, or pairs of binding moieties attached respectively to the polypeptide (or polynucleotide) or test compound and the solid support. Test compounds are preferably bound to the solid support in an array, so that the location of individual test compounds can be tracked. Binding of a test compound to a acylglycerol acyltransferase polypeptide (or polynucleotide) can be accomplished in any vessel suitable for containing the reactants. Examples of such vessels include microtiter plates, test tubes, and microcentrifuge tubes.

In one embodiment, the acylglycerol acyltransferase polypeptide is a fusion protein comprising a domain that allows the acylglycerol acyltransferase polypeptide to be bound to a solid support. For example, glutathione-S-transferase fusion proteins can be adsorbed onto glutathione sepharose beads (Sigma Chemical, St. Louis, Mo.) or glutathione derivatized microtiter plates, which are then combined with the test compound or the test compound and the non-adsorbed acylglycerol acyltransferase polypeptide; the mixture is then incubated under conditions conducive to complex formation (e.g., at physiological conditions for salt and pH). Following incubation, the beads or microliter plate wells are washed to remove any unbound components. Binding of the interactants can be determined either directly or indirectly, as described above. Alternatively, the complexes can be dissociated from the solid support before binding is determined.

Other techniques for immobilizing proteins or polynucleotides on a solid support also can be used in the screening assays of the invention. For example, either a acylglycerol acyltransferase polypeptide (or polynucleotide) or a test compound can be immobilized utilizing conjugation of biotin and streptavidin. Biotinylated acylglycerol acyltransferase polypeptides (or polynucleotides) or test compounds can be prepared from biotin-NHS (N-hydroxysuccinimide) using techniques well known in the art (e.g., biotinylation kit, Pierce Chemicals, Rockford, Ill.) and immobilized in the wells of streptavidin-coated 96 well plates (Pierce Chemical). Alternatively, antibodies which specifically bind to a acylglycerol acyltransferase polypeptide, polynucleotide, or a test compound, but which do not interfere with a desired binding site, such as the active site of the acylglycerol acyltransferase polypeptide, can be derivatized to the wells of the plate. Unbound target or protein can be trapped in the wells by antibody conjugation.

Methods for detecting such complexes, in addition to those described above for the GST-immobilized complexes, include immunodetection of complexes using antibodies which specifically bind to the acylglycerol acyltransferase polypeptide or test compound, enzyme-linked assays which rely on detecting an activity of the acylglycerol acyltransferase polypeptide, and SDS gel electrophoresis under non-reducing conditions.

Screening for test compounds which bind to a acylglycerol acyltransferase polypeptide or polynucleotide also can be carried out in an intact cell. Any cell which comprises a acylglycerol acyltransferase polypeptide or polynucleotide can be used in a cell-based assay system. A acylglycerol acyltransferase polynucleotide can be naturally occurring in the cell or can be introduced using techniques such as those described above. Binding of the test compound to a acylglycerol acyltransferase polypeptide or polynucleotide is determined as described above.

Purified acylglycerol acyltransferase polypeptides comprising a glutathione-S-transferase protein and absorbed onto glutathione-derivatized wells of 96-well microtiter plates are contacted with test compounds from a small molecule library at pH 7.0 in a physiological buffer solution. acylglycerol acyltransferase polypeptides comprise an amino acid sequence shown in any one or more of SEQ ID NO:6 to 10. The test compounds comprise a fluorescent tag. The samples are incubated for 5 minutes to one hour. Control samples are incubated in the absence of a test compound.

The buffer solution containing the test compounds is washed from the wells. Binding of a test compound to a acylglycerol acyltransferase polypeptide is detected by fluorescence measurements of the contents of the wells. A test compound which increases the fluorescence in a well by at least 15% relative to fluorescence of a well in which a test compound is not incubated is identified as a compound which binds to an ADO-ribosylation factor-related polypeptide.

Example 14

Functional Activity

Functional assays can be carried out as described in the specific examples, after contacting either a purified acylglycerol acyltransferase polypeptide or an intact cell with a test compound. A test compound which decreases a functional activity of a human acylglycerol acyltransferase polypeptide by at least about 10, preferably about 50, more preferably about 75, 90, or 100% is identified as a potential agent for decreasing acylglycerol acyltransferase protein activity. A test compound which increases a functional activity by at least about 10, preferably about 50, more preferably about 75, 90, or 100% is identified as a potential agent for increasing acylglycerol acyltransferase protein activity.

Example 15

Effect of Test Compound on Anoinic Transport

Transport of $^3$H-labeled substrate in the presence or absence of a test compound can be measured as described in Hsiang et al. (1999, supra). Briefly, 293c18 cells are transfected with human OATP2-like expression constructs using LipofectAMINE Plus (Life Technologies, Inc.) according to the manufacturer's instructions. The medium is removed, and the cells are washed once in serum-free DMEM. $^3$H-labeled substrate, either alone or in the presence of a test compound, is added in the same medium and incubated at room temperature for 5-10 minutes. The cells are quickly washed once with ice-cold DMEM containing 5% bovine serum albumin, then washed three times with ice-cold DMEM. Cells are lysed in 0.1 N NaOH. Radiolabel incorporation is determined by liquid scintillation counting.

Example 16

Partial Purification

References describing at least partial purification of acylglycerol acyltransferase from naturally occurring sources include: Kamisaka et al., "Purification and Characterization of Diacylglycerol Acyltransferase from the Lipid Body Fraction of Oleaginous Fungus," J. Biochem (Tokyo) 1997 (6) 1107-1114 [Kamisaki et al., (1997)]; Little et al., "Solubilization and Characterization of Diacylglycerol Acyltransferase from Microspore-Derived Cultures of Oilseed Rape," Biochem J. (Dec. 15, 1994) 304 (Pt 3): 951-958 [Little et al., (1994)]; Andersson et al., "Purification of Diacylglycerol: acyltransferase from Rat Liver to Near Homogeneity," J. Lipid Res. (March 1994) 35: 535-545 [Anderson et al., (1994)]; Polokoff & Bell, "Solubilization, Partial Purification and Characterization of Rat Liver Microsomal Diacylglycerol Acyltransferase," Biochim. Biophys. Acta (1980) 618: 129-142 [Polokoff et al., (1980)].

Example 17

Acylglycerol Acyltransferase Assay

Acylglycerol acyltransferase Assay [Bhat et al., (1998)]. MGAT was partially purified from livers of 8-day-old Sprague-Dawley rats obtained from pregnant dams (Zivic-Miller) (7). After the hydroxylapatite chromatography step, the solubilized and highly purified enzyme preparation is free of phospholipids. Aliquots were stored at −70 C. MGAT was assayed in mixed micelles. Briefly, dried lipids were solubilized in 0.2% Triton X-100 and added to the reaction mixture. Concentrations of each lipid and of the hydrophobic MGAT substrate 2-monoC18:1-sn-glycerol are expressed as mole percent, calculated by the equation: 100×{[added lipid]/([total lipid]+[Triton X-100])}. MGAT activity was assayed in a 200 L volume containing 100 mM Tris-HCl (pH 7.0), 0.5 mg/mL BSA, 0.22% Triton X-100 (3 mM micelle concentration), 150 M 2-MO, 25 M [$^3$H]palmitoyl-CoA (115 Ci/mol), 0.25-0.5 g of hydroxylapatite-purified protein, and the indicated concentrations of specific lipids. Concentrations of palmitoyl-CoA, which is water-soluble, are reported as molar concentrations, because we cannot be certain about the amount that partitions into the micelles, particularly in the presence of BSA. Concentrations of palmitoyl-CoA higher than 60 M were not used because inhibition was observed. After a 5 min incubation at 23 C, the products were extracted and analyzed. When necessary, a portion of the heptane extract was chromatographed with carrier lipids on 10 cm silica gel G plates in heptane/isopropyl ether/acetic acid (60:40:4; v/v), and the triacylglycerol and diradylglycerol areas were scraped and counted. All assays contained optimal amounts of substrates and measured initial rates. Another assay for acylglycerol acyltransferase is described in U.S. Pat. No. 6,607,893.

REFERENCES

U.S. Pat. No. 4,522,811
U.S. Pat. No. 4,683,195
U.S. Pat. No. 4,800,195
U.S. Pat. No. 4,965,188
U.S. Pat. No. 5,223,409
U.S. Pat. No. 5,283,317
U.S. Pat. No. 5,403,484
U.S. Pat. No. 5,565,332
U.S. Pat. No. 5,571,698
U.S. Pat. No. 5,641,673
U.S. Pat. No. 6,607,893
WO 84/03564
WO 92/01810
WO 93/03151
WO 94/13804
WO 01/04283
WO 01/04297
WO 01/46258
Agrawal et al., *Trends Biotechnol.* 10, 152-158, 1992
Anderson et al., (1994), *J. Lipid Res.* 35: 535-545
Altschul S F, Madden T L, Schaffer A A, Zhang J, Zhang Z, Miller W, Lipman D J; Nucleic Acids Res 1997 Sep. 1; 25(17): 3389-402
Appa Rao K B, Garg L C, Panda A K, Totey S M; Protein Expr Purif 1997 November; 11(2): 201-8
Barnes, P. J. Mechanisms in COPD. Differences from asthma. Chest 2000, 117:10S14S
Bartel et al., *BioTechniques* 14, 920-924, 1993
Bhat et al., (1998), *Biochemistry;* 37(17):5916-22.
Becker-Andre, M., Meth. Mol. Cell. Biol. 2:189-201 (1991)
Botstein D, W. R., Skolnick M, Davis R W., Am J Hum Genet. 32: 314-31, 1980.
Buhman et al., *J. Biol. Chem.;* 277; 25474-25479
Burton, *Proc. Natl. Acad. Sci.* 88, 11120-23, 1991
Carrell et al. (1994) Angew. Chem. Int. Ed. Engl. 33:2059

Caruthers et al., *Nucl. Acids Res. Symp. Ser.* 215-223, 1980
Cases et al., (2001), *J. Biol. Chem.;* 276 (42); 38870-38876
Cao et al., (2003), *J. Biol. Chem.;* 278 (28); 25657-25663
Cao et al., (2003); *J. Biol. Chem.;* 278 (16); 13860-13866
Cawkwell L, B. S., Lewis F A, Dixon M F, Taylor G R, Quirke P, Br J. Cancer. 67: 1262-7, 1993.
Cech, *Science* 236, 1532-1539; 1987
Cech, *Ann. Rev. Biochem.* 59, 543-568; 1990
Cech, *Curr. Opin. Struct. Biol.* 2, 605-609; 1992
Chen et al., (2001), *J. Clin. Invest.;* 111 (11); 1715-1722
Cho et al. (1993) Science 261:1303
Colbere-Garapin et al., *J. Mol. Biol.* 150, 1-14, 1981
Cole et al., *Mol. Cell. Biol.* 62, 109-120, 1984)
Coruzzi et al., *EMBO J.* 3, 1671-1680, 1984
Cote et al., *Proc. Natl. Acad. Sci.* 80, 2026-2030; 1983
Couture & Stinchcomb, *Trends Genet.* 12, 510-515, 1996
Cull et al. (1992) Proc. Natl. Acad. Sci. USA 89:1865-1869
Cwirla et al. (1990) Proc. Natl. Acad. Sci. USA 87:6378-6382
Devlin (1990) Science 249:404-406
DeWitt et al. (1993) Proc. Natl. Acad. Sci. USA 90:6909
Engelhard et al., *Proc. Nat. Acad. Sci.* 91, 3224-3227, 1994
Erb et al. (1994) Proc. Natl. Acad. Sci. USA 91:11422
Felici (1991) J. Mol. Biol. 222:301-310
Fodor (1993) Nature 364:555-556
Gallop et al. (1994) J. Med. Chem. 37:1233
Gee et al., in Huber & Carr, MOLECULAR AND IMMUNOLOGIC APPROACHES, Futura Publishing Co., Mt. Kisco, N.Y., 1994
Gergen and Weiss, Am Rev Respir Dis 146:823-824, 1992
Gibson, U. E. M., Heid, C. A. and Williams, P. M., Genome Research. 6: 995-1001, 1996.
Hampton et al., SEROLOGICAL METHODS: A LABORATORY MANUAL, APS Press, St. Paul, Minn., 1990
Hartman & Mulligan, *Proc. Natl. Acad. Sci.* 85, 8047-51, 1988
Haseloff et al. *Nature* 334, 585-591, 1988
Heid, C. A., Stevens, J., Livak, K. J., and Williams, P. M., Genome Research, 6: 986-994, 1996.
Holland, P. M., Abramson, R. D., Watson, R. and Gelfand; D. H., PNAS. 88: 7276-7280, 1991.
Horn et al. *Nucl. Acids Res. Symp. Ser.* 225-232, 1980
Houghten (1992) Bio/Techniques 13:412-421
Iwabuchi et al., *Oncogene* 8, 1693-1696, 1993
Jeffreys A J, W. V., Thein S L, Nature. 316: 76-9, 1985.
Johnson et al., *Endoc. Rev.* 10, 317-331, 1989
Kamisaki et al., (1997) J. Biochem (Tokyo) (6) 1107-1114
Kellogg, D. E., et al., Anal. Biochem. 189:202-208 (1990)
Kohler et al., *Nature* 256, 495-497, 1985
Kozbor et al., *J. Immunol. Methods* 81, 31-42, 1985
Kroll et al., *DNA Cell Biol.* 12, 441-453, 1993
Lardizabal et al. (2001), *J. Biol. Chem.;* 276 (42); 38862-38869
Lam (1991) Nature 354:82-84
Lam (1997) Anticancer Drug Des. 12:145
Lam K S. Application of combinatorial library methods in cancer research and drug discovery. Anticancer Drug Des 1997 April; 12(3):145-67
Little et al., (1994), *Biochem J.* 304 (Pt 3): 951-958
Livak, K. J., Flood, S. J., Marmaro, J., Giusti, W. and Deetz, K., PCR Methods and Applications 357-362, 1995.
Logan & Shenk, *Proc. Natl. Acad. Sci.* 81, 3655-3659, 1984
Lowy et al., *Cell* 22, 817-23, 1980
Maddox et al., *J. Exp. Med.* 158, 1211-1216, 1983
Madura et al., *J. Biol. Chem.* 268, 12046-12054, 1993
Maniatis et al., Molecular Cloning: A Laboratory Manual, 1982, Cold Spring Harbor Laboratory, Cold Spring Harbor Press
McConnell et al., *Science* 257, 1906-1912, 1992
Merrifield, *J. Am. Chem. Soc.* 85, 2149-2154, 1963
Morrison et al., *Proc. Natl. Acad. Sci.* 81, 6851-6855, 1984
Murray, 1992, supra
Nagarenko, I. A., et al. Nucleic Acids Research 25:16-21 (1997)
Neuberger et al., *Nature* 312, 604-608, 1984
Nicholls et al., 1993, *J. Immunol. Meth.* 165, 81-91)
Piatak, M. J., et al., BioTechniques 14:70-81 (1993)
Piatak, M. J., et al., Science 259:1749-1754 (1993))
Porath et al., *Prot. Exp. Purif.* 3, 263-281, 1992
Polokof et al., (1980), *Biochim. Biophys. Acta* 618: 129-142
Roberge et al., *Science* 269, 202-204, 1995
Sambrook, J., Fritsch, E. F., and Maniatis, T. (1989) Molecular Cloning: A Laboratory Manual, 2nd ed., Cold Spring Harbor Laboratory Press, NY.
Scott and Smith (1990) Science 249:386-390
Sharp, P. A., et al., Methods Enzymol. 65:750-768, 1980
Sjolander & Urbaniczky, *Anal. Chem.* 63, 2338-2345, 1991
Southern, E. M., J. Mol. Biol., 98:503-517, 1975
Smith et al., (2000), *Nature Genet.* 25; 87-90
Szabo et al., *Curr. Opin. Struct. Biol.* 5, 699-705, 1995
Takamatsu *EMBO J.* 6, 307-311, 1987
Takeda et al., *Nature* 314, 452-454, 1985
Thomas, P. S., Proc. Nat. Acad. Sci., 77:5201-5205, 1980)
Uhlmann et al., *Chem. Rev.* 90, 543-584, 1990
Uhlmann et al., *Tetrahedron. Lett.* 215, 3539-3542, 1987
Verhaar et al., 1995, *Int. J. Cancer* 61, 497-501
Weber et al., Genomics. 7: 524-30, 1990.
Wigler et al., *Cell* 11, 223-32, 1977
Wigler et al., *Proc. Natl. Acad. Sci.* 77, 3567-70, 1980
Yen et al., (2003), *J. Biol. Chem.;* 278 (20); 18632-18537
Zervos et al., *Cell* 72, 223-232, 1993
Zuckermann et al. (1994). J. Med. Chem. 37:2678

The invention claimed is:

1. A purified polypeptide comprising the amino acid sequence SEQ ID NO:2.

2. A composition comprising:
   (1) a polypeptide comprising the amino acid sequence SEQ ID NO:2; and
   (2) a pharmaceutically acceptable carrier.

* * * * *